US009090699B2

(12) United States Patent
Lindsey

(10) Patent No.: US 9,090,699 B2
(45) Date of Patent: Jul. 28, 2015

(54) MIG-7 AS A SPECIFIC ANTICANCER TARGET

(75) Inventor: J. Suzanne Lindsey, Seattle, WA (US)

(73) Assignee: J. Suzanne Lindsey, Jackson, OH (US)

( * ) Notice: Subject to any disclaimer, the term of this patent is extended or adjusted under 35 U.S.C. 154(b) by 1801 days.

(21) Appl. No.: 12/299,160

(22) PCT Filed: May 2, 2007

(86) PCT No.: PCT/US2007/068078
§ 371 (c)(1),
(2), (4) Date: Mar. 2, 2009

(87) PCT Pub. No.: WO2007/131071
PCT Pub. Date: Nov. 15, 2007

(65) Prior Publication Data
US 2009/0203125 A1 Aug. 13, 2009

Related U.S. Application Data

(60) Provisional application No. 60/796,805, filed on May 2, 2006.

(51) Int. Cl.
A61K 38/00 (2006.01)
C07K 7/00 (2006.01)
C07K 14/00 (2006.01)
C07K 16/32 (2006.01)
G01N 33/574 (2006.01)

(52) U.S. Cl.
CPC .......... *C07K 16/32* (2013.01); *G01N 33/57484* (2013.01); *G01N 33/57492* (2013.01)

(58) Field of Classification Search
CPC .......... C07K 14/00; C07K 7/00; A61K 38/00
USPC .......... 530/350, 326; 424/184.1, 277.1, 185.1
See application file for complete search history.

(56) References Cited

U.S. PATENT DOCUMENTS 6,017,748 A 1/2000 Stratagene

FOREIGN PATENT DOCUMENTS

EP WO03066808 A2 8/2003

OTHER PUBLICATIONS

Sharmin S, Sakata K, Kashiwagi K, Ueda S, Iwasaki S, Shirahata A and Igarashi K. Polyamine Cytotoxicity in the Presence of Bovine Serum Amine Oxidase (2001). Biochemical and Biophysical Research Communications, 282, 288-235. Elsevier Science. Amsterdam, Netherlands.
van der Schaft DWJ, Hillen F, Pauwels P, Kirschmann DA, Castermans K, oude Egbrink MGA, Tran MGB, Sciot R, Hauben E, Hogendoorn PCW, Delattre O, Maxwell PH, Hendrix MJC and Griffioen AW. Tumor cell plasticity in Ewing sarcoma, an alternative circulatory system stimulated by hypoxia. (2005). Cancer Research, 65, 11520-11528. American Association for Cancer Research. Philadelphia, PA. US.
Yoshida M, Kashiwagi K, Kawai G, Ishihama A and Igarashi K. Polyamines enhance synthesis of the RNA polymerase sigma 38 subunit by suppression of an amber termination codon in the open reading frame. (2002). Journal of Bioglogical Chemistry, 277, 37139-37146. American Society for Biochemistry and Molecular Biology. Bethesda, MD. US.
Fisher SJ, Cui TY, Zhang L, Hartman L, Grahl K, Zhang GY, et al. Adhesive and degradative properties of human placental cytotrophoblast cells in vitro. Journal of Cell Biology Aug. 1, 1989 ; 109(2):891-902. Rockefeller University Press. New York City, NY. US.
Librach CL, Werb Z, Fitzgerald ML, Chiu K, Corwin NM, Esteves RA, et al. 92-kD type IV collagenase mediates invasion of human cytotrophoblasts. Journal of Cell Biology Apr. 1, 1991 ;113(2):437-49. Rockefeller University Press. New York City, NY. US.
Soundararajan R, Rao AJ. Trophoblast 'pseudo-tumorigenesis': Significance and contributory factors. Reproductive Biology and Endocrinology 2004;2(1):15. BioMed Central LTD. London, United Kingdom.
Zhou Y, Fisher SJ, Janatpour M, Genbacev O, Dejana E, Wheelock M, et al. Human cytotrophoblasts adopt a vascular phenotype as they differentiate. Journal of Clinical Investigation 1997;99(9):2139-51. American Society for Clinical Investigation. Ann Arbor, MI. US.
Janatpour MJ, McMaster MT, Genbacev O, Zhou Y, Dong J, Cross JC, et al. Id-2 regulates critical aspects of human cytotrophoblast differentiation, invasion and migration. Development Feb. 1, 2000 ; 127(3):549-58. The Company of Biologists Ltd. Cambridge, United Kingdom.
Walker-Daniels J, Hess AR, Hendrix MJC, Kinch MS. Differential regulation of EphA2 in normal and malignant cells. American Journal of Pathology 2003;162(4):1037-42. American Association of Pathologists and Bacteriologists. Hagerstown, MD. US.
Hess AR, Seftor EA, Seftor REB, Hendrix MJC. Phosphoinositide 3-Kinase Regulates Membrane Type 1-Matrix Metalloproteinase (MMP) and MMP-2 Activity during Melanoma Cell Vasculogenic Mimicry. Cancer Research Aug. 15, 2003;63(16):4757-62. American Association for Cancer Research. Philadelphia, PA. US.

(Continued)

*Primary Examiner* — Yan Xiao

(57) ABSTRACT

Aspects of the present invention provide novel Mig-7 encoding nucleic acids and Mig-7 polypeptides, recombinant DNA expression systems and host cells containing same, as well as methods of inhibiting expression of the subject nucleic acid molecules, inhibiting production of the encoded proteins or polypeptides, inhibiting metastasis of a carcinoma cell in a subject (including in humans), inhibiting migration/invasion of and mimicking of normal cells by carcinoma cells in a subject, detecting the presence of a cancer cell (e.g., a migrating/invading cancer cell or carcinoma cell mimic, and tumor neovascularization) in a sample of a subject's tissue or body fluids, and inhibiting the migration/invasion of or endothelial cell mimicking by a placental cell into the blood stream or vessels of a female mammal. Particular aspects relate to novel anti-Mig-7 antibodies, diagnostic and/or prognostic methods, and therapeutic methods comprising use of the inventive nucleic acids, polypeptides and antibodies or derivatives thereof.

3 Claims, 28 Drawing Sheets

(56) References Cited

OTHER PUBLICATIONS

Childs AC et al. Polyamine-dependent gene expression. 2003. Cellular and Molecular Life Sciences 60;1394-1406. Birkhäuser Verlag, Basel, Switzerland. polyamine relationship to Z-DNA formation p. 1397; entire document for polyamine effects on expression.
Ausubel,Frederick M.; Brent,Roger; Kingston,Robert E. Current protocols in molecular biology. Selected Topics from Classical Bacterial Genetics 2006 Unit 1.4 John Wiley & Sons. Hoboken, NJ. US. See 1.4.10 Recombination effects on cloned DNA inserts.
Ausubel,Frederick M.; Brent,Roger; Kingston,Robert E. Current protocols in molecular biology. Constructing Recombinant DNA Molecules by the Polymerase Chain Reaction 2006 Unit 3.17 John Wiley & Sons. Hoboken, NJ. US. See entire unit.
Shinde D, Lai Y, Sun F, and Arnheim N. Taq DNA polymerase slippage mutation rates measured by PCR and quasi-likelihood analysis: (CA/GT)n and (A/T)n microsatellites. 2003. Nucleic Acids Research 31(3); 974-980. Oxford University Press. Oxford, United Kingdom.
Pejawar-Gaddya S. and Finn OJ. Cancer vaccines: Accomplishments and challenges. 2008. Critical Reviews in Oncology/Hematology 67(2); 93-102. Elsevier Science. Amsterdam, Netherlands.
Crouch S, Spidel CS, Lindsey JS. HGF and ligation of $\alpha v \beta 5$ integrin induce a novel, cancer cell-specific gene expression required for cell scattering. Experimental Cell Research 2004;292(2):274-87. Academic Press. US.
Phillips TM, Lindsey JS. Carcinoma Cell-specific Mig-7: A new potential marker for circulating and migrating cancer cells. Oncology Reports 2005;13:37-44. National Hellenic Research Foundation. Athens, Greece.
Petty, A.P. Garman, K.L. and Winn, V.D., Spidel, C.M. and Lindsey, J.S. (2007) Overexpression of carcinoma and embryonic cytotrophoblast cell-specific Mig-7 induces invasion and vessel-like structure formation. American Journal of Pathology 170(5) 1763-1780. American Association of Pathologists and Bacteriologists. Hagerstown, MD. US.
Petty, A.P., Dick, C.L. and Lindsey, J.S. (2008) Translation of an atypical human cDNA requires fidelity of a purine-pyrimidine repeat region and recoding. Gene 414:49-59. Elsevier Science. Amsterdam, Netherlands.
Petty, A.P., Wright, S.E., Rewers-Felkins, K.A., Yenderrozos, M.A., Vorderstrasse, B.A., and Lindsey, J.S. (2009) Targeting Mig-7 inhibits carcinoma cell invasion, primary tumor growth, and stimulates monocyte oncolytic activity. Molecular Cancer Therapeutics 8(8):2412-2423. American Association for Cancer Research. Philadelphia, PA. US.
Anonymous. Stratagene Catalog 2003-2004. p. 74. Agilent Technologies. US. In lieu of the catalog stated in the extended European search report dated Aug. 18, 2009, the product manual and patent (see item under patents) for Stop Unwanted Rearrangement *E. coli* (SURE) cells are submitted.
Hendrix MJC, Seftor EA, Kirschmann DA, Quaranta V, Seftor REB. Remodeling of the Microenvironment by Aggressive Melanoma Tumor Cells. Annals of NY Academy of Science May 1, 2003 ; 995(1 ):151-61. Wiley-Blackwell Publishing. Hoboken, NJ. US.
Brooks PC, Klemke RL, Schon S, Lewis JM, Schwartz MA, Cheresh DA. Insulin-like growth factor receptor cooperates with integrin alpha v beta 5 to promote tumor cell dissemination in vivo. Journal of Clinical Investigation 1997;99 (6):1390-8. American Society for Clinical Investigation. Ann Arbor, MI. US.
Klemke RL, Yebra M, Bayna EM, Cheresh DA. Receptor tyrosine kinase signaling required for integrin alpha v beta 5-directed cell motility but not adhesion on vitronectin. Journal of Cell Biology 1994;127(3):859-66. Rockefeller University Press. New York City, NY. US.
Folberg R, Hendrix MJC, Maniotis AJ. Vasculogenic mimicry and tumor angiogenesis. American Journal of Pathology 2000;156(2):361-81. American Association of Pathologists and Bacteriologists. Hagerstown, MD. US.
Wright SE, Kilinski L, TaNb S, Lowe KE, Burnside JS, Wu JY, et al. Cytotoxic T Lymphocytes from humans with adenocarcinomas stimulated by native MUC1 Mucin and a Mucin peptide mutated at a glycosylation site. Journal of Immunotherapy 2000;23(1):2-10. Society for Biological Therapy, Ovid Technologies (Wolters Kluwer)-Lippincott Williams & Wilkins. Milwaukee, Wisconsin. US.
Hendrix MJC, Seftor EA, Seftor REB. Comparison of tumor cell invasion assays: human amnion versus reconstituted basement membrane barriers. Invasion & Metastasis 1989;9:278-97. Karger Publishers. Basel, Switzerland. See abstract.
Roehm NW, Rodgers GH, Hatfield SM, Glasebrook AL. An improved colorimetric assay for cell proliferation and viability utilizing the tetrazolium salt XTT. Journal of Immunological Methods 1991;142(2):257-65. Elsevier Science. Amsterdam, Netherlands. See abstract.
Müller A, Homey B, Soto H, Ge N, Catron D, Buchanan ME, et al. Involvement of chemokine receptors in breast cancer metastasis. Nature 2001;410:50-6. Nature Publishing Group, a division of Macmillan Publishing. London, United Kingdom.
Ahmad KA, Wang G, Slaton J, Unger G, Ahmed K. Targeting CK2 for cancer therapy. Anti-cancer Drugs 2006;16 (10):1037-43. Lippincott Williams & Wilkins. Philadelphia, PA. US.
Curcio LD, Bouffard DY, Scanlon KJ. Oligonucleotides as modulators of cancer gene expression. Pharmacology Therapeutics 1997;74:317-32. Elsevier Science. Amsterdam, Netherlands.
Elez R, Piiper A, Kronenberger B, Kock M, Brendel M, Hermann E, et al. Tumor regression by combination antisense therapy against Plk1 and Bcl-2. Oncogene 2003;22(1 ):69-80. Nature Publishing Group, a division of Macmillan Publishing. London, United Kingdom.
Wang H, Hang J, Shi Z, Li M, Yu D, Kandimalla ER, et al. Antisense oligonucleotide targeted to Rlalpha subunit of cAMP-dependent protein kinase (GEM231 ) enhances therapeutic effectiveness of cancer chemotherapeutic agent irinotecan in nude mice bearing human cancer xenografts: in vivo synergistic activity, pharmacokinetics and host toxicity. International Journal of Oncology 2002;21 (1):73-80. Demetrios A. Spandidos Publisher, Athens, Greece. See abstract.
Zelweger T, Miyake H, Cooper S, Chi K, Conklin BS, Monia BP, et al. Antitumor activity of antisense clusterin oligonucleotides is improved in vitro and in vivo by incorporation of 2'-O-(2-methoxy)ethyl chemistry. Journal of Pharmacology & Experimental Therapeutics 2001;298(3):934-40. American Society for Pharmacology and Experimental Therapeutics. Bethesda, MD. US.
Tuma RS. Trastuzumab Faces Trials, Clinical and Otherwise. Journal of the National Cancer Institute Mar. 1, 2006;98 (5):296-8. Oxford University Press. Oxford, United Kingdom.
Bonta IL, Ben Efraim S. Interactions between inflammatory mediators in expression of antitumor cytostatic activity of macrophages. Immunology Letters 1990;25(4):295-301. Elsevier Science. Amsterdam, Netherlands.
Hildesheim A, de Gonzalez AB. Etiology and Prevention of Cervical Adenocarcinomas. Journal of the National Cancer Institute Mar. 1, 2006 ;98(5):292-3. Oxford University Press. Oxford, United Kingdom.
Condeelis J, Singer RH, Segall JE. The Great Escape: When Cancer Cells Hijack the Genes for Chemotaxis and Motility. Annual Review of Cell and Developmental Biology 2005;21 (1 ):695-718. Annual Reviews. Palo Alto, CA. US.
Altschul SF, Madden TL, Schaffer AA, Zhang J, Zhang Z, Miller W and Lipman DJ. Gapped BLAST and PSI-BLAST: a new generation of protein database search programs (1997). Nucleic Acids Research, 25, 3389-3402. Oxford University Press. Oxford, United Kingdom.
Atkins JF and Gesteland R. The 22nd Amino Acid (2002). Science, 296, 1409-1410. American Association for the Advancement of Science. Washington D.C. US.
Childs AC, Mehta DJ and Gerner EW. Polyamine-dependent gene expression. (2003). Cellular and Molecular Life Sciences, 60, 1394-1406. Birkhäuser. Basel, Switzerland.
Claverie J-M. Fewer Genes, More Noncoding RNA (2005). Science, 309, 1529-1530. American Association for the Advancement of Science. Washington D.C. US.
Fuchs RPP, Freund AM and Bichara M. Methods and Consequences of DNA damage processing. Alan R. Liss, Inc.: New York, NY. US.

(56) References Cited

OTHER PUBLICATIONS

Original citation from text. Fuchs et al Mechanisms of Dinucleotide Repeat Instability in *Escherichia coli*. 2000. Genetics 154: 533-542.

Gerner, E.W., Meyskens, F.L., Polyamines and cancer: old molecules,new understanding. 2004. Nature Reviews, Cancer 4, 781-792. Nature Publishing Group, a division of Macmillan Publishing. London, United Kingdom.

Gesteland, R.F., Weiss, R.B., Atkins, J.F., 1992. Recoding: reprogrammed genetic decoding. Science 257, 1640-1641. American Association for the Advancement of Science. Washington D.C. US.

Giedroc, D.P., Theimer, C.A., Nixon, P.L., Structure, stability and function of RNA pseudoknots involved in stimulating ribosomal frameshifting. 2000. Journal of Molecular Biology 298, 167-185. Elsevier Science. Amsterdam, Netherlands.

Givant-Horwitz V, Davidson B and Reich R. Laminin-induced signaling in tumor cells (2005). Cancer Letters, 223, 1-10. Elsevier Science. Amsterdam, Netherlands.

Han K and Byun Y. PSEUDOVIEWER2: visualization of RNA pseudoknots of any type. (2003). Nucleic Acids Research, 31 , 3432-3440. Oxford University Press. Oxford, United Kingdom.

Harrell L, Melcher U and Atkins JF. Predominance of six different hexanucelotide recording signals 3' of read-through stop condons. (2002). Nucleic Acids Research, 30, 2011-2017. Oxford University Press. Oxford, United Kingdom.

Hess AR, Postovit L-M, Margaryan NV, Seftor EA, Schneider GB, Seftor REB, Nickoloff BJ and Hexdrix MJC. Focal Adhesion Kinase Promotes the Aggresive Melanoma Phenotype (2005). Cancer Research, 65, 9851-9860. American Association for Cancer Research. Philadelphia, PA. US.

Howard, M.T., Agrawal, G., Anderson, C.B., Khatri S., Flangigan, K.M., Atkins, J.F., Recoding elements located adjacent to a subset of eukaryal selenocysteine-specifying UGA codons. 2005. EMBO Journal. 24, 1596-1607. European Molecular Biology Organization, Nature Publishing Group, a division of Macmillan Publishing. London, United Kingdom.

Howard MT, Shirts BH, Zhou J, Carlson CL, Matsufuji S, Gesteland RF, Weeks RS and Atkins JF. Cell culture analysis of the regulatory frameshift event required for the expression of mammalian antizymes (2001). Genes to Cells, 6, 931-941. Wiley-Blackwell Publishing. Hoboken, NJ. US.

Hryniewicz MM and Vonder Haar RA. Polyamines enhance readthrough of the UGA termination codon in a mammalian messenger RNA. (1983). Molecular and General Genetics, 190, 336-343. Springer-Verlag. New York City, NY. US. see abstract.

Ivanov IP, Gesteland RF and Atkins JF. Antizyme expression: a subversion of triplet decoding, which is remarkably conserved by evolution, is a sensor for an autoregulartory circuit (2000). Nucleic Acids Research, 28, 3185-3196. Oxford University Press. Oxford, United Kingdom.

Kozak M. Constraints on reinitiation of translation in mammals. (2001). Nucleic Acids Research, 29, 5226-5232. Oxford University Press. Oxford, United Kingdom.

Kozak, M., The scanning model for translation: an update. 1989. Journal of Cell Biology,108, 229-241. Rockefeller University Press. New York City, NY. US.

Kuchino, Y., Beier, H., Akitta, N., Nishimura, S., Natural UAG suppressor glutamine tRNA is elevated in mouse cells infected with Moloney murine leukemia virus. 1987. Proceedings of the National Academy of Sciences. 84, 2668-2672. National Academy of Sciences. Washington, D.C. US.

Lucia-Ortega L, De los Rios V, Martinez-Ruiz A, O Oñaderra aderra M, Lacadena J and Gavilanes JG. Anomalous electrophoretic behavior of a very acidic protein: Ribonuclease U2 (2005). Electrophoresis, 26, 3407-3413. Wiley-Blackwell Publishing. Hoboken, NJ. US.

Manktelow E, Shigemoto K and Brierley I. Characterization of the frameshift signal of Edr, a mammalian example of programmed −1 ribosomal frameshifting. (2005). Nuecleic Acids Research, 33, 1553-1563. Oxford University Press. Oxford, United Kingdom.

Mix, H., Lobanov, A.V., Gladyshev, V.N., SECIS elements in the coding regions of selenoprotein transcripts are functional in higher eukaryotes. 2007. Nucleic Acids Research 35, 414-423. Oxford University Press. Oxford, United Kingdom.

Moon, S., Byun, Y., Kim, H.-J., Jeong, S., Han, K., 2004. Predicting genes expressed via −1 and +1 frameshifts. Nucleic Acids Research 32, 4884-4892. Oxford University Press. Oxford, United Kingdom.

Meyskens FL, Jr. and Gerner EW. Development of Difluoromethylornithine (DFMO) as a Chemoprevention Agent (1999). Clinical Cancer Research, 5, 945-951. American Association for Cancer Research. Philadelphia, PA. US.

Petros LM, Howard MT, Gesteland RF and Atkins JF. Polyamine sensing during antizyme mRNA programmed frameshifting. (2005). Biochemical and Biophysical Research Communications, 338, 1478-1489. Elsevier Science. Amsterdam, Netherlands.

Seftor REB, Seftor EA, Koshikawa N, Meltzer PS, Gardner LMG, Bilban M, Stetler-Stevenson WG, Quanranta V and Hendrix MJC. Cooperative interactions of laminin 5 g2 chain, matrix metalloproteinase-2, and membrane type-1 matrix/metalloproteinase are required for mimicry of embryonic vasculogenesis by agressive melanoma. (2001). Cancer Research, 61, 6322-6327. American Association for Cancer Research. Philadelphia, PA. US.

Shah AA, Giddings MC, Parvaz JB, Gesteland RF, Atkins JF and Ivanov IP. Computational identification of putative programmed translational frameshift sites. (2002). Bioinformatics, 18, 1046-1053. Oxford University Press. Oxford, United Kingdom.

FIGURE 1A
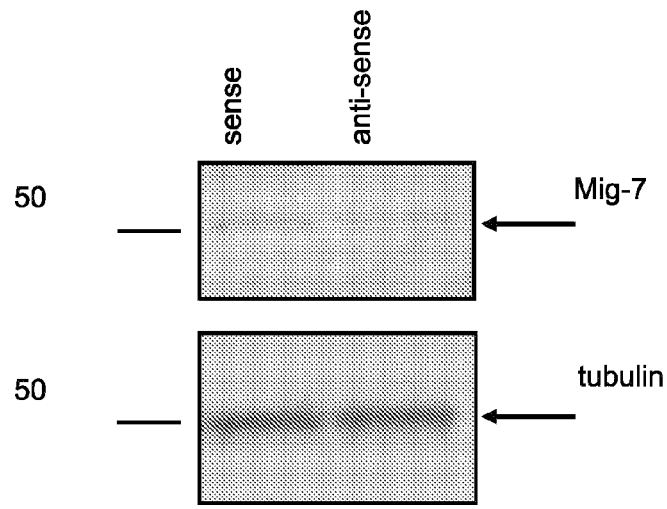
FIGURE 1B
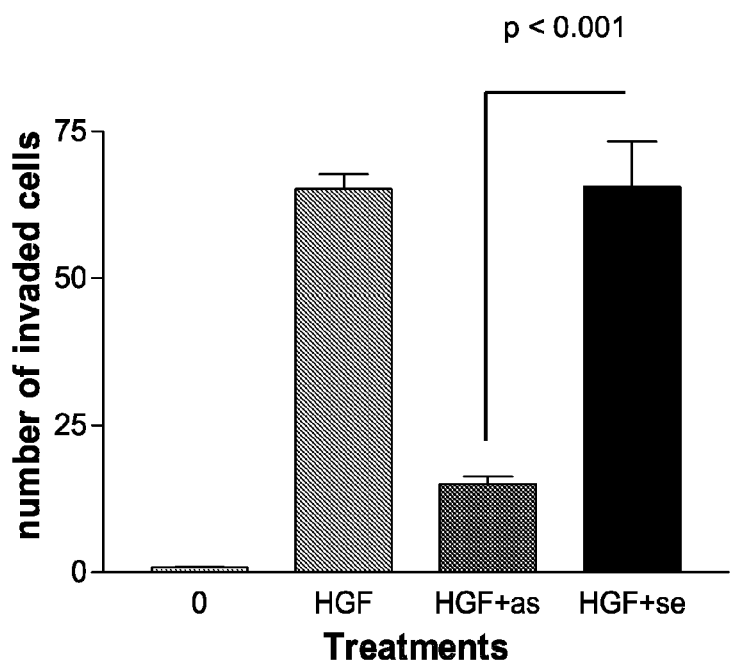
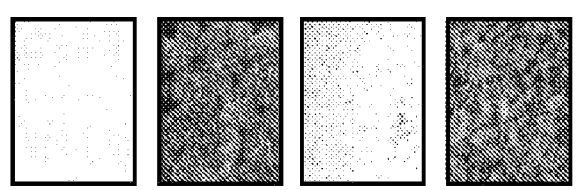

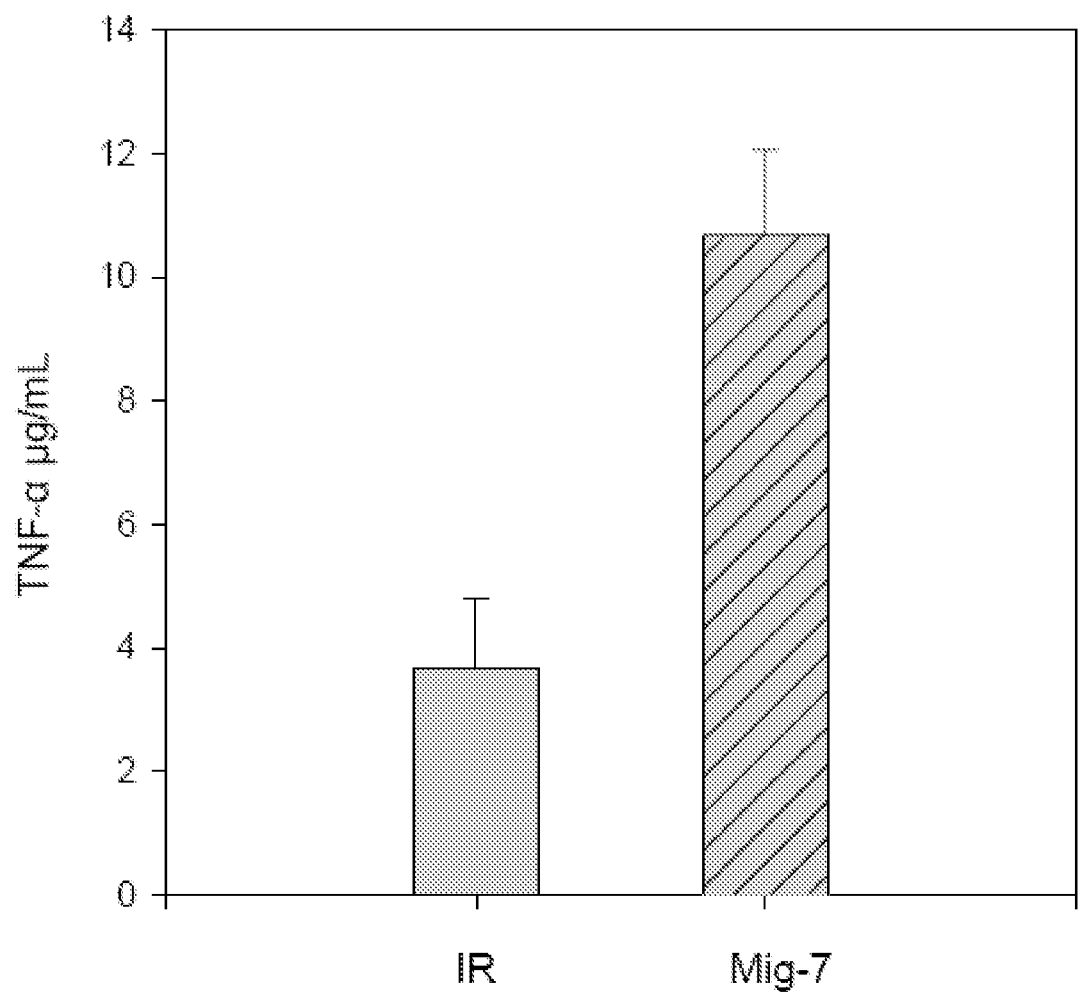

FIGURE 4A

```
nggaattngtttacgactcactacagggcgaattgggcctctagatgctgctcgagcggccgccagtgtg
atggatatctgcagaattcggcttgaacactgcgtttgctggctttgatgaaattaagccacattaaagt
acccataagcccataatgcaaaagaaccccaaaaccagcccagcagccaaccatggcagcaagtagatgc
tctggtctttagatagtcagaaatgacacttctgggctctcaggcagtcagtgggttgagctccccatta
aagtcccccctgccaagtctggaatagtcctagtcccgtgtgtgtgtgtgtgtgtgtgtgtgtgtgtgt    27gt
gtgtgtgtgtgtgtgtgtaccgcgtgcatatgcgcgcatgcagtgcagggtctgcatacctaaagca
gatgaaattctgcagaatggctgcctcctanacaaagtcaanaaganagaacgaggagccnantccncac
actggcgggcgttactantggatcnaacncggtacanctgaagcn (SEQ ID NO.:9)

tancgcnaatgctnanttaggtnacactatagaatactcaagctatgcatcaagcttggtaccgagctcg
gatccactagtaacggccgccagtgtgctggaattcggcttgaacactgcgtttgctggctttgatgaaa
ttaagtcacattaaagtacccataagcccataatgcaaaagaaccccaaaaccagcccagcagccaacca
tggcagcaagtagatgctctggtctttagatagtcagaaatgacacttctgggctctcaggcagtcagtg
ggttgagctccccattaaagtcccctgccaagtctggaatagtcctagtcccgtgtgtgtgtgtgtg     28gt
tgtgtgtgtgtgtgtgtgtgtgtgtgtgtgtgtgtaccgcgtgcatatgcgcgcatgcagtgcagg
gtctgcatacctaaagcagatgaaattctgcanaatggctgcctcactanacaaagtcnanaananagaa
cgaggaaccgaattctgcanatatccacacactgggggcgctcgaacagctn (SEQ ID NO.:10)

ngnnaattngttttnacngactcactgatagggcgaattgggcctctagtangcatgctcgagcggccg
ccagtgtgatggatatctgcagaattcggcttcctcggtctgtcttcttgactttgtctagtgaggcagc
cattctgcagaatttcatctgctttaggtatgcagaccctgcactgcatgcgcgcatatgcacgcgggta
cacacacacacacacacacacacacacacacacacacacacacacacacacacgggactaggactatt
ccagacttggcaggggggactttaatggggagctcaacccactgactgcctgagagcccagaagtgtcatt   27gt
tctgactatctaaagaccagagcatctacttgctgccatggttggctgctggctggttttggggttctt
ttgcattatgggcttatgggtactttaatgtgacttaatttcatcaaagccagcaaacgcagtgttcaag
ccgaattccancacactggcgggcgttactaatggatcgaactcggtacaagctta (SEQ ID
NO.:11)

ggggttnctnatttagtgtccacactnatagaatactcaagctatgcatcaagcttggtnaccnganctc
ggatccactagtaacggccgccagtgtgctggaattcggctcctcggtctgtcttcttgactttgtctag
tgaggcagccattctgcagaatttcatctgctttaggtatgcagaccctgcactgcatgcgcgcatatgc
acgcgggtacacacacacacacacacacacacacacacacacacacacacacacacacacgggactag
gactattccagacttggcaggggggactttaatggggagctcaacccactgactgcctgagagcccagaag   26gt
tgtcatttctgactatctaaagaccagagcatctacttgctgccatggttggctgctggctggttttgg
ggttcttttgcattatgggcttatgggtactttaatgtggcttaatttcatcaaagccacaaacgcagtg
ttcaagccgaattctgcanatatccatcacactggcgggcgctcaaactn (SEQ ID NO.:12)

ttcgcnatgctnanttaggtnacctnatagnaatactcaagctatgcatcaagcttggtaccgagctcgg
atccactagtaacggccgccagtgtgctggaattcggcttcctcggtctgtcttcttgactttgtctagt
gaggcagccattctgcagaatttcatctgctttaggtatgcagaccctgcactgcatgcgcgcatatgca
cgcgggtacacacacacacacacacacacacacacacacacacacacacacacacacacacacgggac
taggactattccagacttggcaggggggactttaatggggagctcaacccactgactgcctgagagcccag   28gt
aagtgtcatttctgactatctaaagaccagagcatctacttgctgccatggttggctgctgggctggttt
tggggttcttttgcattatgggcttatgggtactttaatgtgacttaatttcatcaaagccacaaaccag
tgttcaagccnaattctgcaaatatccacacactggcgggcgctcnaacatn (SEQ ID NO.:13)

tannnnnnnnggaatttgtcctacgactcactcgagggcgaattgggcantctatatgctgctcgagcgg
ccgccagtgtgatggatatctgcagaattcggcttgaacactgcgtttgctggctttgatgaaattaagt
cacattaaagtacccataagcccataatgcaaaagaaccccaaaaccagcccagcagccaaccatggcag
caagtagatgctctggtctttagatagtcagaaatgacacttctgggctctcaggcagtcagtgggttga
gctccccattaaagtcccctgccaagtctggaatagtcctagtcccgtgtgtgtgtgtgtgtgtgtgtg     27gt
tgtgtgtgtgtgtgtgtgtgtgtgtgtgtacccgcgtgcatangcgcgcatgcagtgctnggtctgca
tacctaaaacaaatnanatctgcagaatgggctgcctcnctanacnnntcaaaaanacgangaaggaaac
cnaattccncnccnggcggncgttantantggatccagcncggtaccngctgaagcn (SEQ ID
NO.:14)
```

FIGURE 4B

```
tancgcaattgctnanttagngtccacactnatagaatactcaagctatgcatcaagcttggtaccgagc
tcggatccactagtaacggccgccagtgtgctggaattcggcttgaacactgcgtttgctggctttgatg
aaattaagtcacattaaagtacccataagcccataatgcaaaagaaccccaaaaccagcccagcagccaa
ccatggcagcaagtagatgctctggtctttagatagtcagaaatgacacttctgggctctcaggcagtca
gtgggttgagctccccattaaagtcccctgccaagtctggaatagtcctagtcccgtgtgtgtgtgt       28gt
gtgtgtgtgtgtgtgtgtgtgtgtgtgtgtgtgtgtgtgtacccgcgtgcatatgcgcgcatgcagtg
cagggtctgcatacctaaagcanatgaaattctgcagaatggctgcctcactanacaaagtcaanaanac
agaacgaggaagcgaattccgcaaatatccaccactggngggcgctcnagcatgcn (SEQ ID
NO.:15)

ggaatngttttacgactcactgcgagggcgaattgggcactctagatgctgctcgagcggccgccagtgt
gatggatatctgcanaattcggcttgaacactgcgtttgctggctttgatgaaattaagtcacattaaag
tacccataagcccataatgcaaaagaaccccaaaaccagcagccagcagccaaccatggcagcaagtagatg
ctctggtctttagatagtcagaaatgacacttctgggctctcaggcagtcagtgggttgagctccccatt      29gt
aaagtcccctgccaagtctggaatagtcctagtcccgtgtgtgtgtgtgtgtgtgtgtgtgtgtgtg
tgtgtgtgtgtgtgtgtgtgtacccgcgtgcatatgcgcgcatgcagtgcgggtctgcataccta
aagcagatgaaatctgcagaanggctgctcactanacanagtcaagaananngacgaggaagccgaattc
cccncctgggggcgttactantggatcgagctcggtacancttga (SEQ ID NO.:16)

ttncngcnattgctnattnagggtncacactnatagaatactcaagctatgcatcaagcttgggnaccga
gctcggatccactagtaacggccgccagtgtgctggaattcggcttgaacactgcgtttgctggctttga
tgaaattaagtcacattaaagtacccataagcccataatgcaaaagaaccccaaaaccagcccagcagcc
aaccatggcagcaagtagatgctctggtctttagatagtcagaaatgacacttctgggctctcaggcagt     27gt
cagtgggttgagctccccattaaagtcccctgccaagtctggaatagtcctagtcccgtgtgtgtgtgt
gtgtgtgtgtgtgtgtgtgtgtgtgtgtgtgtgtgtgtacncgcgtgnanatgcgcgcatggnntg
cngggtctgcatacaanagcananaaaatctgcagaatggntgcncnctnanaagtctaaaaacaaacna
ggagccnaaatctgcaaaatccncncnggnggcgccaanatannctn (SEQ ID NO.:17)

nnnnggaattngttntacgactcacttatagggcgaattgggcctctagatgcatgctcgagcggccgcc
agtgtgatggatatctgcagaattcggcttcctcggtctgtcttcttgactttgtctagtgaggcagcca
ttctgcagaatttcatctgctttaggtatgcagaccctgcactgcatgcgcgcatatgcacgcgggtaca
cacacacacacacacacacacacacacacacacacacacacacgggacnacgacaattcca               26gt
canntggacnggggacnttaatggggagntcaacccactgantgcctganagnccncaantgtcttttc
tgactatctaaagacnanancatctacttgctnccatggttggctgctgggcngggttttggggtnctct
tgcattatgggcnnatgggtatttnatgtgacntaatntcncnaaccncctnacgcagtgttcancccga
attccagcanactgggggcgtnaatantggatcnaactcggtacaancttgatcantn (SEQ ID
NO.:18)

tnncngcnattgctnatntagngtggacactnatagaatactcaagctatgcatcaagcttggntaccga
gctcggatccactagtaacggccgccagtgtgctggaattcggcttcctcggtctgtcttcttgactttg
tctagtgaggcagccattctgcagaatttcatctgctttaggtatgcagaccctgcactgcatgcgcgca
tatgcacgcgggtacacacacacacacacacacacacacacacacacacacacacacacacacacaca     28gt
cgggactaggactattccagacttggcagggggactttaatggggagctcaacccactgactgcctgaga
gcccagaagtgtcatttctgactatctaaagaccagagcatctacttgctgccatggttggctgctgggc
tggttttggggttcttttgcattatgggcttatgggtactttaatgtgacttaatttcatcaaagccaca
acgcagtgttcaagccnaatctgcaaatatccatcacactggcggcgctcnaacatcn (SEQ ID
NO.:19)

gggggggttttacgactcactgccgagggcgaattgggcactctatatgcatgctcgagcggccgccag
tgtgatggatatctgcagaattcggcttcctcggtctgtcttcttgactttgtctagtgaggcagccatt
ctgcagaatttcatctgctttaggtatgcagaccctgcactgcatgcgcgcatatgcacgcgggtacaca
cacacacacacacacacacacacacacacacacacacacacacgggactaggactattccag            27gt
acttggcagggggactttaatggggagctcaacccactgactgcctgagagcccagaagtgtcatttctg
actatctaaagaccagagcatctacttgctgccatggttggctgctgggctggttttggggttcttttgc
attatgggcttatgggtactttaatgtgacttaatttcatcaaagccagcaaacgcagtgttcaagccga
attccagcacactggcgggcgttactaatggatcgaactcngtancaagcttgatc (SEQ ID
NO.:20)
```

FIGURE 4C nncnntgctnanntaggtcacactatagaatactcaagctatgcatcaagcttggtaccgagctcggatc
cactagtaacggccgccagtgtgctggaattcggcttcctcggtctgtcttcttgactttgtctagtgag
gcagccattctgcagaatttcatctgctttaggtatgcagaccctgcactgcatgcgcgcatatgcacgc
gggtacacacacacacacacacacacacacacacacacacacacacacgggactaggactantccaga    22gt
cttggcagggggactttaatggggagctcaacccactgactgcctgagagcccanaagtgtcatttctga
ctatctaaanaccanagcatctacttgctgccatggttggctgctgggctggttttggggttcttttgcn
ttatgggcttatgggtactttaatgtgacttaatttcatcaaagccancaaaccagtgttcaanccgaat
tctgcagatatccacanactggcggcgctccancatgctctanagg (SEQ ID NO.:21)

gnaattngtttacgactcactacagggcgaattgggcctctagatgctgctcgagcggccgccagtgtga
tggatatctgcagaattcggcttgaacactgcgtttgctggctttgatgaaattaagtcacattaaagta
cccataagcccataatgcaaaagaaccccaaaaccagcccagcagccaaccatggcagcaagtagatgct
ctggtctttagatagtcagaaatgacacttctgggctctcaggcagtcagtgggttgagctcccattaa    23gt
agtcccctgccaagtctggaatagtcctagtcccgtgtgtgtgtgtgtgtgtgtgtgtgtgtgtgtgtg
tgtgtgtgtgtacccgcgtgcatatgcgcgcatgcagtgcngggtctgcatacctaaagcanatgaaatt
ctgcagaaatggctgcctcactanacnncgtcaanaanacagaccgangaagccgaattccnncccactg
ggcggncgttactagtggatccaancccggtacaancttgaangcan (SEQ ID NO.:22)

tannngcnatgctnanttaggtgaactnatagaatactcaagctatgcatcaagcttggtaccgagctcg
ganccactagtaacggccgccagtgtgctggaattcggcttcctcggtctgtcttcttgactttgtctag
tgaggcagccatnctgcagaatttcatctgctttaggtatgcagaccctgcactgcatgcgcgcatatgc
acgcgggtacacacacacacacacacacacacacacacacacacacacacacacacacacacncagganaan    27gt
gactattncanacttggnnggggggactttaatggggagctcaacccactgactgnctganagcacatang
tgtcnttnctgactatctaaagaccagancatctacttgctgccatggttggctgctgggctggtntngg
ggttcttttgcattatgggcttatnggtactttaangtgacttantttcatcaaagccaacanacgctnt
gtcaaaccgaatctacanatatccatcacactggcnggcgcncaa (SEQ ID NO.:23)

nnnggaatttgttttacgactcactgcgagggcgaattgggcctctagatgcatgctcgagcggccgcca
gtgtgatggatatctgcagaattcggcttgaacactgcgttgctggctttgatgaaattaagtcacatta
aagtacccataagcccataatgcaaaagaaccccaaaaccagcccagcagccaaccatggcagcaagtag
atgctctggtctttagatagtcagaaatgacacttctgggctctcaggcagtcagtgggttgagctcccc    29gt
attaaagtcccctgccaagtctggaatagtcctantcccgtgtgtgtgtgtgtgtgtgtgtgtgtgtgt
gtgtgtgtgtgtgtgtgtgtacccgcgtgcatatgcgcgcatgcagtgcngggtctgcatac
ctaaagcanatnaaattctgcanaatggctgcctcactanacaaagtcaaaaaaaaagacgnngaanccn
aattccncccctggcgggcgttactantggatccaactcggtncancttgangcnn (SEQ ID
NO.:24)

FIGURE 5A

```
gnaattngtttacgactcactacagggcgaattgggcctctagatgctgctcgagcggccgccagtgtga
tggatatctgcagaattcggcttgaacactgcgtttgctggctttgatgaaattaagtcacattaaagta
cccataagcccataatgcaaaagaaccccaaaaccagcccagcagccaaccatggcagcaagtagatgct
ctggtctttagatagtcagaaatgacacttctgggctctcaggcagtcagtgggttgagctccccattaa    23gt
agtcccccctgccaagtctggaatagtcctagtcccgtgtgtgtgtgtgtgtgtgtgtgtgtgtgtgtg
tgtgtgtgtgtacccgcgtgcatatgcgcgcatgcagtgcngggtctgcatacctaaagcanatgaaatt
ctgcagaaatggctgcctcactanacnncgtcaanaanacagaccgangaagccgaattccnncccactg
ggcggncgttactagtggatccaancccggtacaancttgaangcan    (SEQ ID NO:22)
```

```
nnnggaatttgttttacgactcactgcgagggcgaattgggcctctagatgcatgctcgagcggccgcca
gtgtgatggatatctgcagaattcggcttgaacactgcgttgctggctttgatgaaattaagtcacatta
aagtacccataagcccataatgcaaaagaaccccaaaaccagcccagcagccaaccatggcagcaagtag
atgctctggtctttagatagtcagaaatgacacttctgggctctcaggcagtcagtgggttgagctcccc
attaaagtcccccctgccaagtctggaatagtcctantcccgtgtgtgtgtgtgtgtgtgtgtgtgtgtgt
gtgtgtgtgtgtgtgtgtgtgtacccgcgtgcatatgcgcgcatgcagtgcngggtctgcatac    29gt
ctaaagcanatnaaattctgcanaatggctgcctcactanacaaagtcaaaaaaaaagacgnngaanccn
aattccnccccctggcgggcgttactantggatccaactcggtncancttgangcnn    (SEQ ID NO:24)
```

FIGURE 5B

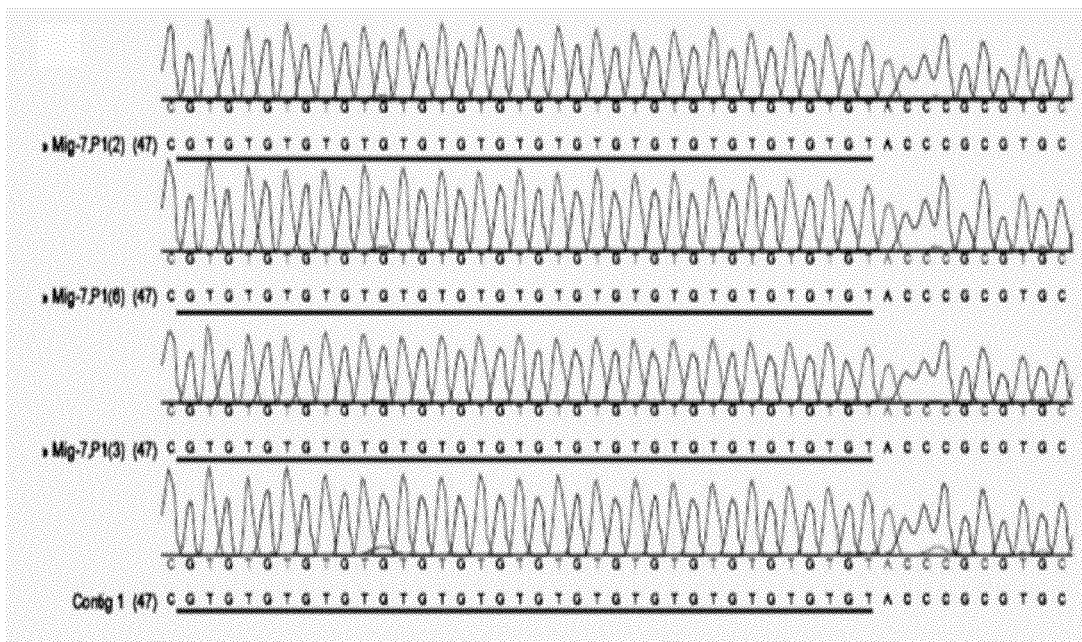

FIGURE 7B

FIGURE 8A atggcagcaagtagatgctctggtctttagatagtcagaaatgacacttctgggctctcaggcagtcagtggttgagctccc
cattaaagtcccccctgccaagtctggaatagtcctagtcccgtgtgtgtgtgtgtgtgtgtgtgtgtgtgtacccgcgtgc
atatgcgcgcatgcagtgcagggtctgcatacctaaagcagatgaaattctgcagaatggctgcctcgctagacaaagtca
agaagacagaccgaggagagagaggttgatgtgtctccactaccaagagacaggcttctctaagccagcgagacatcc
catccaacaatatgaaactggccacatttccttgagatgtcaacgttgaaagtgtagctgcatctttattcttcactgttatgaag
ttgggtgcaacacagcttgagtggaatacaaaaacaccgcttggaaacacatgatctggatttgaatcgcagctgtatcatt
cacctgctatagactctgagcaagacctctctgaggttatttcttcacagtaggtagagacaagacttacttcaaaggttcttaa
agttgaacctgagtcaatgaatgcaaaagtgttcacatttaaactgtaattttaaagcacaatacaagtaaatagcattaatat
cattagagagattaacttagcactgtgcgtcacatgattcatcacggcggatcccgggtg    SEQ ID NO: 43

FIGURE 8B

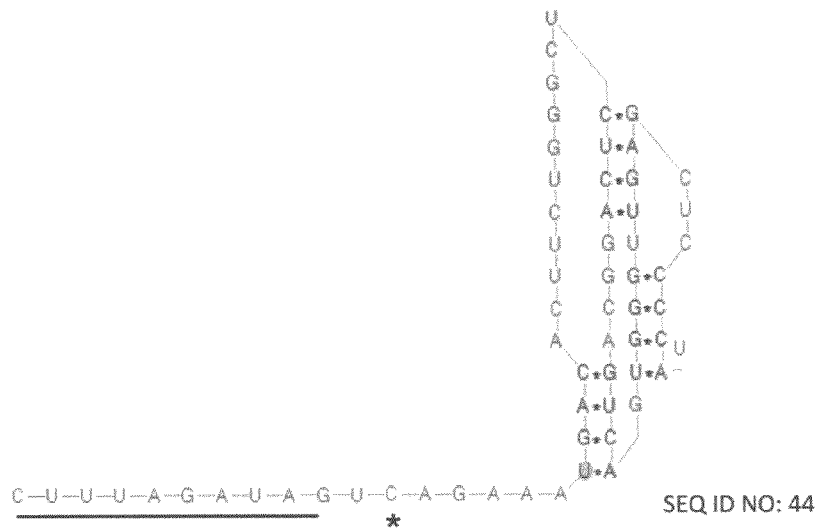

SEQ ID NO: 44

FIGURE 8C

```
              M  A  A  S  R  C  S  G  L  *        S  E
    cagccaaccatggcagcaagtagatgctctggtctttagatagtcagaa  61
      M  T  L  L  G  S  Q  A  V  S  G  L  S  S  P  L  K  S  P  C
 62 atgacacttctgggctctcaggcagtcagtgggttgagctccccattaaagtcccccctgc 121
      Q  V  W  N  S  P  S  P  V  C  V  C  V  C  V  C
122 caagtctggaatagtccagtcccgtgtgtgtgtgtgtgtgtgtgtgtgtgt 181
      T  R  V  H  M  R  A  C  S  A  G  S  A  Y  L  K  Q  M  K  F
182 acccgcgtgcatatgcgcgcatgcagtgcagggtctgcatacctaaagcagatgaaattc 241
      C  R  M  A  A  S  L  D  K  V  K  K  T  D  R  G  E  R  G  *
242 tgcagaatggctgcctcgctagacaaagtcaagaagacagaccgaggagagagaggttga 301
      C  V  S  T  T  K  R  Q  A  S  L  S  Q  R  D  I  P  S  N  N
302 tgtgtctccactaccaagagacaggcttctctaagccagcgagacatcccatccaacaat 361
      M  K  L  A  T  F  P  *  D  V  N  V  E  S  V  A  A  S  L  F
362 atgaaactggccacatttccttgagatgtcaacgttgaaagtgtagctgcatctttattc 421
      F  T  V  M  K  L  G  A  T  Q  L  E  W  N  T  K  T  P  L  G
422 ttcactgttatgaagttgggtgcaacacagcttgagtggaatacaaaaacaccgcttgga 481
      N  T  *  S  G  F  E  S  Q  L  Y  H  S  P  A  I  D  S  E  Q
482 aacacatgatctggatttgaatcgcagctgtatcattcacctgctatagactctgagcaa 541
      D  L  S  E  V  I  S  S  Q  *  V  E  T  R  L  T  S  K  V  L
542 gacctctctgaggttatttcttcacagtaggtagagacaagacttacttcaaaggttctt 601
      K  V  E  P  E  S  M  N  A  K  V  F  T  F  K  L  *     *
602 aaagttgaacctgagtcaatgaatgcaaaagtgttcacatttaaactgtaattttaaa    661
```

SEQ ID NOs: 45 and 46

FIGURE 8D

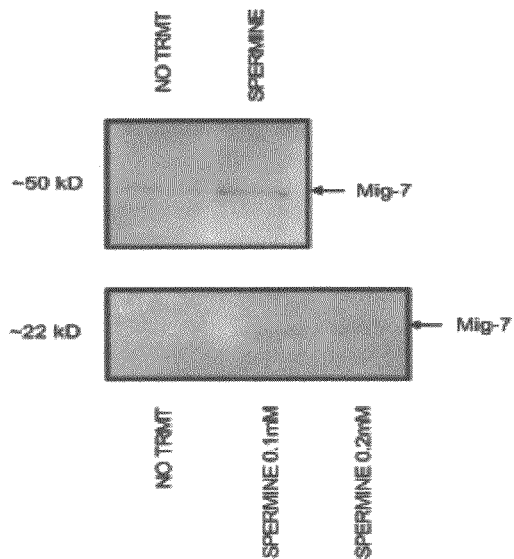

FIGURE 9A

```
      M  A  A  S  R  C  S  G  L  *  I  V  R  N  D  T  S  G  L
  1   accatggcagcaagtagatgctctggtctttagatagtcagaaatgacacttctgggctc   60
      S  G  S  Q  W  V  E  L  P  I  K  V  P  L  P  S  L  E  *  S
 61   tcaggcagtcagtgggttgagctccccattaaagtcccctgccaagtctggaatagtcc   120
      *  S  R  V  C  V  C  V  C  V  C  V  C  V  Y  P  R  A  Y  A
121   tagtcccgtgtgtgtgtgtgtgtgtgtgtgtgtgtgtgtacccgcgtgcatatgcg   180
      R  M  Q  C  R  V  C  I  P  K  A  D  E  I  L  Q  N  G  C  L
181   cgcatgcagtgcagggtctgcatacctaaagcagatgaaattctgcagaatggctgcctc   240
      A  R  Q  S  Q  E  D  R  P  R  R  E  R  L  M  C  L  H  Y  Q
241   gctagacaaagtcaagaagacagaccgaggagagagaggttgatgtgtctccactaccaa   300
      E  T  G  F  S  K  P  A  R  H  P  I  Q  Q  Y  E  T  G  H  I
301   gagacaggcttctctaagccagcgagacatcccatccaacaatatgaaactggccacatt   360
      S  L  R  C  Q  R  *  K  C  S  C  I  F  I  L  H  C  Y  E  V
361   tccttgagatgtcaacgttgaaagtgtagctgcatctttattcttcactgttatgaagtt   420
      G  C  N  T  A  *  V  E  Y  K  N  T  A  W  K  H  M  I  W  I
421   gggtgcaacacagcttgagtggaatacaaaaacaccgcttggaaacacatgatctggatt   480
      *  I  A  A  V  S  F  T  C  Y  R  L  *  A  R  P  L  *  G  Y
481   tgaatcgcagctgtatcattcacctgctatagactctgagcaagacctctctgaggttat   540
      F  F  T  V  G  R  D  K  T  Y  F  K  G  S  *  S  *  T  *  V
541   ttcttcacagtaggtagagacaagacttacttcaaaggttcttaaagttgaacctgagtc   600
      N  E  C  K  S  V  H  I  *  T  V  I  L  K  H  N  T  S  K  *
601   aatgaatgcaaaagtgttcacatttaaactgtaattttaaagcacaatacaagtaaatag   660
      H  *  Y  H  *  R  D  *  L  S  T  V  R  H  M  I  H  H  G  H
661   cattaatatcattagagagattaacttagcactgtgcgtcacatgattcatcacggccat   720
      L  *  D  I  K  *  R  G  E  A  C  S  N  K  K  Y  C  H  S  Y
721   ctgtgagatatcaaatagagaggtgaagcctgcagtaataaaaaatactgccatagctat   780
```

(SEQ ID NO:32)
(SEQ ID NO:35)

Figure 9B

```
         P  W  Q  Q  V  D  A  L  V  F  R  *  S  E  M  T  L  L  G  S
1    ccatggcagcaagtagatgctctggtctttagatagtcagaaatgacacttctgggctct   60
         Q  A  V  S  G  L  S  S  P  L  K  S  P  C  Q  V  W  N  S  P
61   caggcagtcagtgggttgagctccccattaaagtcccctgccaagtctggaatagtcct   120
         S  P  V  C  V  C  V  C  V  C  V  C  T  R  V  H  M  R
121  agtcccgtgtgtgtgtgtgtgtgtgtgtgtgtgtgtacccgcgtgcatatgcgc        180
         A  C  S  A  G  S  A  Y  L  K  Q  M  K  F  C  R  M  A  A  S
181  gcatgcagtgcagggtctgcatacctaaagcagatgaaattctgcagaatggctgcctcg  240
         L  D  K  V  K  K  T  D  R  G  E  R  G  *  C  V  S  T  T  K
241  ctagacaaagtcaagaagacagaccgaggagagagaggttgatgtgtctccactaccaag   300
         R  Q  A  S  L  S  Q  R  D  I  P  S  N  N  M  K  L  A  T  F
301  agacaggcttctctaagccagcgagacatcccatccaacaatatgaaactggccacattt   360
         P  *  D  V  N  V  E  S  V  A  A  S  L  F  F  T  V  M  K  L
361  ccttgagatgtcaacgttgaaagtgtagctgcatctttattcttcactgttatgaagttg   420
         G  A  T  Q  L  E  W  N  T  K  T  P  L  G  N  T  *  S  G  F
421  ggtgcaacacagcttgagtggaatacaaaaacaccgcttggaaacacatgatctggattt   480
         E  S  Q  L  Y  H  S  P  A  I  D  S  E  Q  D  L  S  E  V  I
481  gaatcgcagctgtatcattcacctgctatagactctgagcaagacctctctgaggttatt   540
         S  S  Q  *  V  E  T  R  L  T  S  K  V  L  K  V  E  P  E  S
541  tcttcacagtaggtagagacaagacttacttcaaaggttcttaaagttgaacctgagtca   600
         M  N  A  K  V  F  T  F  K  L  *  F  *  S  T  I  Q  V  N  S
601  atgaatgcaaaagtgttcacatttaaactgtaatttttaaagcacaatacaagtaaatagc  660
         I  N  I  I  R  E  I  N  L  A  L  C  V  T  *  F  I  T  A  I
661  attaatatcattagagagattaacttagcactgtgcgtcacatgattcatcacggccatc   720
         C  E  I  S  N  R  E  V  K  P  A  V  I  K  N  T  A  I  A
721  tgtgagatatcaaatagagaggtgaagcctgcagtaataaaaaatactgccatagctat    779
```

(SEQ ID NO:33)
(SEQ ID NO:36)

Figure 9C

```
            H  G  S  K  *  M  L  W  S  L  D  S  Q  K  *  H  F  W  A  L
  1   catggcagcaagtagatgctctggtctttagatagtcagaaatgacacttctgggctctc   60
            R  Q  S  V  G  *  A  P  H  *  S  P  P  A  K  S  G  I  V  L
 61   aggcagtcagtgggttgagctccccattaaagtcccnctgccaagtctggaatagtccta  120
            V  P  C  V  C  V  C  V  C  V  C  V  P  A  C  I  C  A
121   gtcccgtgtgtgtgtgtgtgtgtgtgtgtgtgtgtacccgcgtgcatatgcgcg       180
            H  A  V  Q  G  L  H  T  *  S  R  *  N  S  A  E  W  L  P  R
181   catgcagtgcagggtctgcatacctaaagcagatgaaattctgcagaatggctgcctcgc  240
            *  T  K  S  R  R  Q  T  E  E  R  E  V  D  V  S  P  L  P  R
241   tagacaaagtcaagaagacagaccgaggagagagaggttgatgtgtctccactaccaaga  300
            D  R  L  L  *  A  S  E  T  S  H  P  T  I  *  N  W  P  H  F
301   gacaggcttctctaagccagcgagacatcccatccaacaatatgaaactggccacatttc  360
            L  E  M  S  T  L  K  V  *  L  H  L  Y  S  S  L  L  *  S  W
361   cttgagatgtcaacgttgaaagtgtagctgcatctttattcttcactgttatgaagttgg  420
            V  Q  H  S  L  S  G  I  Q  K  H  R  L  E  T  H  D  L  D  L
421   gtgcaacacagcttgagtggaatacaaaaacaccgcttggaaacacatgatctggatttg  480
            N  R  S  C  I  I  H  L  L  *  T  L  S  K  T  S  L  R  L  F
481   aatcgcagctgtatcattcacctgctatagactctgagcaagacctctctgaggttattt  540
            L  H  S  R  *  R  Q  D  L  L  Q  R  F  L  K  L  N  L  S  Q
541   cttcacagtaggtagagacaagacttacttcaaaggttcttaaagttgaacctgagtcaa  600
            *  M  Q  K  C  S  H  L  N  C  N  F  K  A  Q  Y  K  *  I  A
601   tgaatgcaaaagtgttcacatttaaactgtaatttttaaagcacaatacaagtaaatagca  660
            L  I  S  L  E  R  L  T  *  H  C  A  S  H  D  S  S  R  P  S
661   ttaatatcattagagagattaacttagcactgtgcgtcacatgattcatcacggccatct  720
            V  R  Y  Q  I  E  R  *  S  L  Q  *  *  K  I  L  P  *  L
721   gtgagatatcaaatagagaggtgaagcctgcagtaataaaaaatactgccatagctat    778
```

(SEQ ID NO:34)
(SEQ ID NO:37)

Black columns = HT29 cells transfected with Mig-7 expression vector
Grey columns = HT29 cells transfected with empty vector

MIG-7 AS A SPECIFIC ANTICANCER TARGET

CROSS-REFERENCE TO RELATED APPLICATIONS

This application claims the benefit of priority to Unites States Provisional Patent Application Ser. Nos. 60/796,805, filed 2 May 2006, which is incorporated herein by reference in its entirety. This application relates to the subject matter of U.S. patent application Ser. No. 502,163 (Pub. No. 20050124800), which is also incorporated herein by reference in its entirety.

STATEMENT REGARDING FEDERALLY-SPONSORED RESEARCH

This work was supported at least in part by NIH grant no. CA93925, and the United States government may therefore have certain rights.

FIELD OF THE INVENTION

Aspects of the present invention relate generally to isolated Mig-7 encoding nucleic acids and Mig-7 polypeptides encoded thereby, which molecules confer on mammalian carcinoma cells an ability to undergo cell migration. Recombinant DNA expression systems and host cells containing the subject nucleic acid molecule, as well as antisense oligonucleotides, are also described. Also disclosed are methods of inhibiting expression of the subject nucleic acid molecule, inhibiting production of the encoded protein or polypeptide, inhibiting metastasis of a carcinoma cell in a subject (including in humans), inhibiting migration/invasion of and mimicking of normal cells by carcinoma cells in a subject, detecting the presence of a cancer cell (e.g., migrating/invading or normal cell mimicking carcinoma cell as well as tumor neovascularization) in a sample of a subject's tissue or body fluids, and inhibiting the migration/invasion of or endothelial cell mimicking by a placental cell into the blood stream or vessels of a female mammal. Particular aspects relate to antibodies specific for the novel Mig-7 polypeptides, along with novel diagnostic and/or prognostic methods, and novel therapeutic methods comprising use of the inventive nucleic acids, polypeptides and antibodies or derivatives thereof.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790097_402USPC_SEQUENCE_LISTING.txt. The text file is 37.9 KB, was created on Mar. 2, 2009 and is being submitted electronically via EFS-Web.

BACKGROUND

Migration Induction Gene 7 ("Mig-7"). The present Applicant previously discovered an example of carcinoma-specific gene expression that is tightly regulated at transcription and translation, and is referred to as Migration Inducting Gene 7 ("Mig-7", as referred to herein) (1;2). Mig-7 is a cysteine-rich protein localized to the cell membrane and cytoplasm whose mRNA and protein synthesis is atypical (1;2). Because of an unusual encoding region (DQ080207), and algorithms currently used to determine expression, Mig-7 or the ESTs to which it is homologous are not currently represented on any microarray even though its expression is restricted to carcinoma cells. Mig-7 expression is a result of receptor tyrosine kinase (RTK) activation in concert with ligation of αvβ5 integrin (αvβ5). Mig-7 antisense olignucleotide (ODN) but not inverted antisense ODN inhibits carcinoma cell scattering (1). Malignant tumors, blood from cancer patients and metastatic sites express Mig-7 regardless of tissue of origin. Notably, Mig-7 has not been detected in 25 different normal tissues (n=6 each tissue) or in blood from normal subjects (1;2).

Aggressive, invasive tumor cells can form vessel-like structures in 3D cultures. Laminin 5 γ2 promigratory fragments promote this vessel-like formation by aggressive melanoma cells in 3D cultures. In vivo, predominantly tumor rather than endothelial cells form vessels in the interior, more hypoxic region of tumors (3). Moreover, RTK-induced cancer cell migration, invasion and dissemination of aggressive carcinoma cells require αvβ5 signaling (4;5), the crosstalk that induces Mig-7, in vivo and in vitro (1). Fetal cytotrophoblasts are similar to cancer cells because they invade the maternal tissues during placenta development under RTK and αvβ5 signaling, evade immune system detection, endovascularly invade and are the only other cell type known to undergo vasculogenic mimicry (6). Surprisingly, Mig-7 cDNA is homologous to ESTs isolated from early invasive stage placenta as well as all cancer types studied while, in contrast, is not found in noninvasive term placenta or in other normal tissues (1;2). Moreover, Mig-7 is expressed by fetal cytotrophoblasts as well as carcinoma cells and plays a role in their common cell behavior of vessel-like structure formation and vascular remodeling. Moreover, as presently disclosed herein, adhesion assays to various components of the extracellular matrix suggests that a mechanism for Mig-7 in vessel formation by tumor cells is due to less adhesion to laminin.

There is a pronounced need in the art for compositions and methods to improved the specificity of cancer treatments to decease non-specific toxic side effects. There is a pronounced need for discovery and targeting of solid cancer-specific gene expression, particularly of broad-spectrum or pan-carcinoma expression, to provide for improved dosing and fewer side effects.

SUMMARY OF THE INVENTION

Because Mig-7 expression is specific to solid cancer cells in the adult and plays a role in aggressive tumor cell behavior, the present Applicant conceived that Mig-7 expression provides for a cancer-specific target allowing for novel diagnostic/prognostic and/or therapeutic compositions and methods that will inhibit the spread of cancer while preventing damage to normal cells.

According to particular aspects, Mig-7 is a pan-solid cancer cell target, and targeting Mig-7 in anticancer therapies provides novel therapies specific to tumor cells while sparing normal cells, and enabling higher effective doses with fewer side-effects.

According to additional aspects, Mig-7 is a pan-carcinoma expression marker for cancer diagnosis and/or prognosis, as well as a pan-carcinoma therapeutic target for cancer therapies.

Particular aspects provide an isolated nucleic acid molecule comprising SEQ ID NO:1, or a nucleic acid sequence that is 99.5% or 99%, homologous thereto.

Additional aspects, provide an isolated nucleic acid molecule comprising SEQ ID NO:1, or a nucleic acid sequence that is 99%, 98%, 97%, 96%, or 95% homologous thereto, wherein there are 18 gt repeats between nucleotides 934 and 971 of SEQ ID NO:1.

Additional embodiments provide an isolated nucleic acid molecule comprising a sequence that encodes a Mig-7 polypeptide comprising an amino acid sequence selected from the group consisting of SEQ ID NOS:38, 39, 40, 41, 42, fragments of of SEQ ID NOS:38 and 39 of about 17 to 85 contiguous residues in length, and fragments of SEQ ID NOS: 40, 41 and 42 of about 8 to 81 contiguous residues in length, and combinations thereof, wherein the polypeptide comprises an amino terminal MAASRCSGL (SEQ ID NO:31) sequence. In particular aspects, the isolated nucleic acid molecule comprises a sequence that encodes a polypeptide comprising an amino acid sequence selected from the group consisting of SEQ ID NO: 40, 41, 42, fragments thereof of about 8 to 81 contiguous residues in length, and combinations thereof, and wherein the polypeptide comprises an amino terminal MAASRCSGL (SEQ ID NO:31) sequence. In certain aspets, the isolated nucleic acid molecule comprises a sequence that encodes a polypeptide comprising an amino acid sequence selected from the group consisting of SEQ ID NO: 40, 41, and fragments thereof of about 16 to 81 contiguous residues in length, and wherein the polypeptide comprises an amino terminal MAASRCSGL (SEQ ID NO:31) sequence. In particular embodiments, the isolated nucleic acid molecule comprises a sequence that encodes a polypeptide comprising an amino acid sequence selected from the group consisting of SEQ ID NO: 40, and fragments thereof of about 26 to 81 contiguous residues in length, and wherein the polypeptide comprises an amino terminal MAASRCSGL (SEQ ID NO:31) sequence. In certain embodiments, the fragments of SEQ ID NOS:38, 39, 40, 41 and 42 correspond to contiguous amino acid sequences positioned between stop codons of the encoding nucleic acid sequence. In certain aspects, the isolated nucleic acid molecule confers on a human cell an ability to undergo cell migration, tissue invasion or metastasis. In certain aspects, the cell is a human carcinoma cell.

Additional embodiments provide a protein or polypeptide comprising an amino acid sequence selected from the group consisting of SEQ ID NO: 38, 39, 40, 41, 42, fragments of SEQ ID NOS:38 and 39 of about 17 to 85 contiguous residues in length, and fragments of SEQ ID NOS: 40, 41 and 42 of about 8 to 81 contiguous residues in length, and combinations thereof, wherein the polypeptide comprises an amino terminal MAASRCSGL (SEQ ID NO:31) sequence. In certain aspects, the polypeptide comprises an amino acid sequence selected from the group consisting of SEQ ID NO: 40, 41, 42, fragments thereof of about 8 to 81 contiguous residues in length, and combinations thereof, and wherein the polypeptide comprises an amino terminal MAASRCSGL (SEQ ID NO:31) sequence. In certain embodiments, the polypeptide comprises an amino acid sequence selected from the group consisting of SEQ ID NO: 40, 41, and fragments thereof of about 16 to 81 contiguous residues in length, and wherein the polypeptide comprises an amino terminal MAASRCSGL (SEQ ID NO:31) sequence. In additional embodiments, the polypeptide comprises an amino acid sequence selected from the group consisting of SEQ ID NO:40, and fragments thereof of about 26 to 81 contiguous residues in length, and wherein the polypeptide comprises an amino terminal MAASRCSGL (SEQ ID NO:31) sequence. In certain aspects, the fragments of SEQ ID NOS: 38, 39, 40, 41 and 42 correspond to contiguous amino acid sequences positioned between stop codons of an encoding nucleic acid sequence.

Further aspects, provide a recombinant DNA expression system comprising an expression vector into which is inserted an isolated nucleic acid molecule according to any one of claims 1-3. In certain aspects, the nucleic acid molecule is heterologous to the expression vector. In particular embodiments, the nucleic acid molecule is inserted into the vector in proper sense orientation and correct reading frame.

Yet additional aspects, provide a host cell incorporating an isolated nucleic acid molecule according to any one of claims 1-3. In certain aspects, the isolated nucleic acid molecule is heterologous to the host cell.

Additional embodiments provide an isolated antibody or antigen-binding portion thereof raised against or specific for a protein or polypeptide according to any one of claims 11-15. In certain aspects, the antibody is monoclonal or polyclonal, or is a single-chain antibody, chimeric antibody, humanized antibody or Fab fragment.

Further embodiments provide a method for detecting the presence of a cancer cell in a sample of a subject's tissue or body fluids, comprising: providing a protein or polypeptide according to any one of claims 11-15 as an antigen; contacting the sample with the antigen; and detecting any reaction that indicates that the cancer cell is present in the sample using a suitable assay. In certain aspects, the assay is selected from the group consisting of an enzyme-linked immunosorbent assay, a radioimmunoassay, a gel diffusion precipitin reaction assay, an immunodiffusion assay, an agglutination assay, a fluorescent immunoassay, a protein A immunoassay, and an immunoelectrophoresis assay.

Additional embodiments provide a method for detecting the presence of cancer cell in a sample of a subject's tissue or body fluids, comprising: providing an antibody or antigen-binding portion thereof according to claim 21; contacting the sample with the antibody or antigen-binding portion thereof; and detecting any reaction that indicates that the cancer cell is present in the sample using a suitable assay. In certain aspects, the assay system is selected from the group consisting of an enzyme-linked immunosorbent assay, a radioimmunoassay, a gel diffusion precipitin reaction assay, an immunodiffusion assay, an agglutination assay, a fluorescent immunoassay, a protein A immunoassay, and an immunoelectrophoresis assay.

Yet further embodiments provide a method for detecting the presence of a cancer cell in a sample of a subject's tissue or body fluids, comprising: providing a nucleotide sequence of the nucleic acid molecule according to any one of claims 1-10 as a probe in a nucleic acid hybridization assay; contacting the sample with the probe; and detecting any reaction which indicates that the cancer cell is present in the sample.

Additional embodiments provide a method for detecting the presence of a cancer cell in a sample of a subject's tissue or body fluids, comprising: providing a nucleotide sequence of the nucleic acid molecule according any one of claims 1-10 as a probe in a gene amplification and detection procedure; contacting the sample with the probe; and detecting any reaction which indicates that the migrating carcinoma cell is present in the sample.

In particular aspects these methods are used for cancer diagnosis and/or prognosis, and including the diagnostic/prognostic use of RT_PCR and other nucleic acid techniques to detect Mig-7 for diagnostic or nondiagostic purposes.

Additional embodiments provide a method for detecting the presence of fetal cytotrophoblast cells in a sample of a subject's tissue or body fluids, comprising: providing an antibody or antigen-binding portion thereof according to claim 21; contacting the sample with the antibody or antigen-binding portion thereof; and detecting any reaction that indicates that the cancer cell is present in the sample using a suitable assay. In certain aspects, the assay system is selected from the group consisting of an enzyme-linked immunosorbent assay, a radioimmunoassay, a gel diffusion precipitin reaction assay, an immunodiffusion assay, an agglutination assay, a fluorescent immunoassay, a protein A immunoassay, and an immunoelectrophoresis assay.

Yet additional embodiments provide a method for detecting the presence of fetal cytotrophoblast cells in a sample of a subject's tissue or body fluids, comprising: providing a nucleotide sequence of the nucleic acid molecule according to any one of claims 1-10 as a probe in a detection assay; contacting the sample with the probe; and detecting any reaction that indicates that fetal cytotrophoblast cells are present in the sample. In certain aspects, the detection assay is selected from the group consisting of a nucleic acid hybridization assay and a gene amplification detection procedure.

Additional embodiments provide a method for treating or preventing cancer or metastasis, comprising administering to a subject having a cancer, a therapeutically effective amount of an anti-Mig-7 antibody or antigen-binding fragment thereof, or a pharmaceutical composition comprising the antibody or antigen-binding fragment thereof, wherein cancer is treated, prevented or precluded from metastasis.

Additional embodiments provide a method for targeting a therapeutic agent to a cell, comprising attaching the therapeutic agent to an anti-Mig-7 antibody or antigen-binding portion thereof, that binds to a Mig-7 expressing target cell. In preferred embodiments, the target cell is a cancer cell or a fetal cytotrophoblast cell.

Additional embodiments provide a pharmaceutical composition for treating cancer, comprising, an anti-Mig-7 antibody or antigen-binding portion thereof, and a pharmaceutically acceptable diluent, carrier or excipient.

Additional embodiments provide an anti-cancer vaccine, comprising at least one Mig-7 protein or polypeptide comprising an amino acid sequence selected from the group consisting of SEQ ID NO: 38, 39, 40, 41, 42, fragments of SEQ ID NOS:38 and 39 of about 17 to 85 contiguous residues in length, and fragments of SEQ ID NOS: 40, 41 and 42 of about 8 to 81 contiguous residues in length, and combinations thereof. In certain aspects, the polypeptide comprises an amino acid sequence selected from the group consisting of SEQ ID NO: 40, 41, 42, fragments thereof of about 8 to 81 contiguous residues in length, and combinations thereof. In particular aspects, the polypeptide comprises an amino acid sequence selected from the group consisting of SEQ ID NO: 40, 41, and fragments thereof of about 16 to 81 contiguous residues in length. In certain aspects, the polypeptide comprises an amino acid sequence selected from the group consisting of SEQ ID NO: 40, and fragments thereof of about 26 to 81 contiguous residues in length. In particular embodiments, at least one of the polypeptides comprises an amino terminal MAASRCSGL (SEQ ID NO:31) sequence.

Additional embodiments provide a method for treating or preventing cancer or metastasis, comprising administering to a subject in need thereof, a therapeutically effective amount of an anti-cancer vaccine according to any one of claims 39-43, wherein cancer is treated, prevented or precluded from metastasis.

Additional embodiments provide a method for cloning and expressing a protein from a presumed non-coding DNA sequence, comprising: obtaining a presumed non-coding DNA sequence comprising a plurality of guanine-thymidine (GT) dinucleotide repeats, and at least one stop codon; cloning the presumed non-coding DNA sequence into a bacterial cloning vector to provide a recombinant vector comprising the presumed non-coding DNA sequence; transfecting the recombinant vector into a SURE™ or TOP10F' *E. coli* strain, or the equivalent thereof; and selecting a stable transfectant for subsequent expression studies to determine whether the presumed non-coding DNA sequence is a coding or non-coding sequence. In certain aspects, the putative coding sequence comprises stop codons in at least two reading frames. In additional aspects, the putative coding sequence comprises stop codons in all three reading frames. In certain embodiments, the number of GT dinucleotide repeats is at least 5, at least 10, at least 15, at least 20, at least 25, or at least 30.

Additional embodiments provide an array comprising a plurality of different Mig-7proteins or polypeptides coupled to a solid phase, wherein the Mig-7 proteins or polypeptides comprising at least one amino acid sequence selected from the group consisting of SEQ ID NO: 38, 39, 40, 41, 42, fragments of SEQ ID NOS:38 and 39 of about 17 to 85 contiguous residues in length, and fragments of SEQ ID NOS: 40, 41 and 42 of about 8 to 81 contiguous residues in length, and combinations thereof. In certain aspects, the Mig-7 proteins or polypeptides comprise at least one amino acid sequence selected from the group consisting of SEQ ID NO: 40, 41, 42, fragments thereof of about 8 to 81 contiguous residues in length, and combinations thereof. In particular aspects, the Mig-7 proteins or polypeptides comprises at least one amino acid sequence selected from the group consisting of SEQ ID NO: 40, 41, and fragments thereof of about 16 to 81 contiguous residues in length. In certain aspects, the Mig-7 proteins or polypeptides comprise at least one amino acid sequence selected from the group consisting of SEQ ID NO: 40, and fragments thereof of about 26 to 81 contiguous residues in length. In certain aspects, at least one of the Mig-7 proteins or polypeptides the polypeptide comprises an amino terminal MAASRCSGL (SEQ ID NO:31) sequence.

Yet additional aspects provide an array comprising a plurality of any of the nucleic acid sequences according to any one of claims 1-3, or comprise a plurality of fragments of these sequences.

Yet further aspects provide A method of ex vivo therapy, comprising: obtaining immune cells ex vivo; stimulating the immune cells with at least one Mig-7 polypeptide; and infusing the stimulated immune cells into a patient for carcinoma cell killing in vivo.

BRIEF DESCRIPTION OF THE DRAWINGS

FIGS. 1A and 1B show, according to exemplary aspects of the present invention, that antisense to Mig-7 inhibits chemoinvasion. A) Immunoblot demonstrating that Mig-7 antisense ODN decreases Mig-7 protein levels in lysates from HEC1A cells treated as described in Materials and Methods as compared to lysates from HEC1A cells treated with Mig-7 sense ODN, B) Mig-7 antisense (as), significantly inhibits HEC1A carcinoma cell SF(HGF) chemoinvasion of Matrigel as compared to SF (HGF) treatment alone or SF (HGF) with sense (se) Mig-7 ODN. Images below each treatment group show a representative invasion of cells for that group. Experiments were performed in triplicate for each treatment and repeated three times.

FIGS. 3A-D show, according to exemplary aspects of the present invention, that Mig-7 peptides enhance human monocyte killing of MCF-7 breast carcinoma cells. (A) Representative RT-PCR demonstrating expression of Mig-7 in MCF-7 cells. (B) Human MC cells stimulated with IL-2 and either no peptide (O), pooled irrelevant peptides (IR), or pooled Mig-7 peptides. (see Table 1). Note that Mig-7 peptides significantly (p value 0.001) enhanced MC killing of MCF7 carcinoma cells. Experiments have been repeated 3 times in replicates of 6 for each treatment group. MC were isolated from two different individuals. (C) Cytotoxic response of human isolated MC after peptide stimulation using indicated ratios of immune cells (MC) to MCF-7 cells. Bars are ±S.E. Experiments were repeated twice with replicates of six for each treatment group. (D) TNF-α production by human isolated MC after indicated peptide stimulation. TNF-α production was measured by ELISA assay as described in Methods and Materials after MC were cultured for 8 days with MUC1 peptide plus irrelevant peptides Mig-7 peptides. Bars are ±S.E. Assays were performed in triplicate.

FIG. 4 shows, according to exemplary aspects of the present invention, 16 sequences (SEQ ID NOS:9-24) corresponding to representative sequences of Mig-7 region containing gt repeats (underlined) ranging from 23 to 29 in length. The sequences were derived not using the genetically engineered *E. coli* (SURE™, Stratagene) that was determined herein to provide for maintaining the integrity of the Mig-7 purine-pyrimidine repeat coding region.

FIGS. 5A and 5B show, according to exemplary aspects of the present invention, that genetically engineered *E. Coli* (SURE.™., Stratagene) are required (suitable) to maintain the integrity of the Mig-7 purine-pyrimidine repeat coding region. FIG. 5A shows representative sequences of Mig-7 region containing gt repeats (underlined) ranging from 23 (SEQ ID NO: 22) to 29 (SEQ ID NO: 24) repeats in length (additional sequences are shown in FIG. 4). FIG. 5B shows Representative sequences of Mig-7 plasmids grown in SURE cells. Note the consistent number (18) of gt repeats (SEQ ID NOs: 35, 36, 37, 43, 45).

Figure 7B:
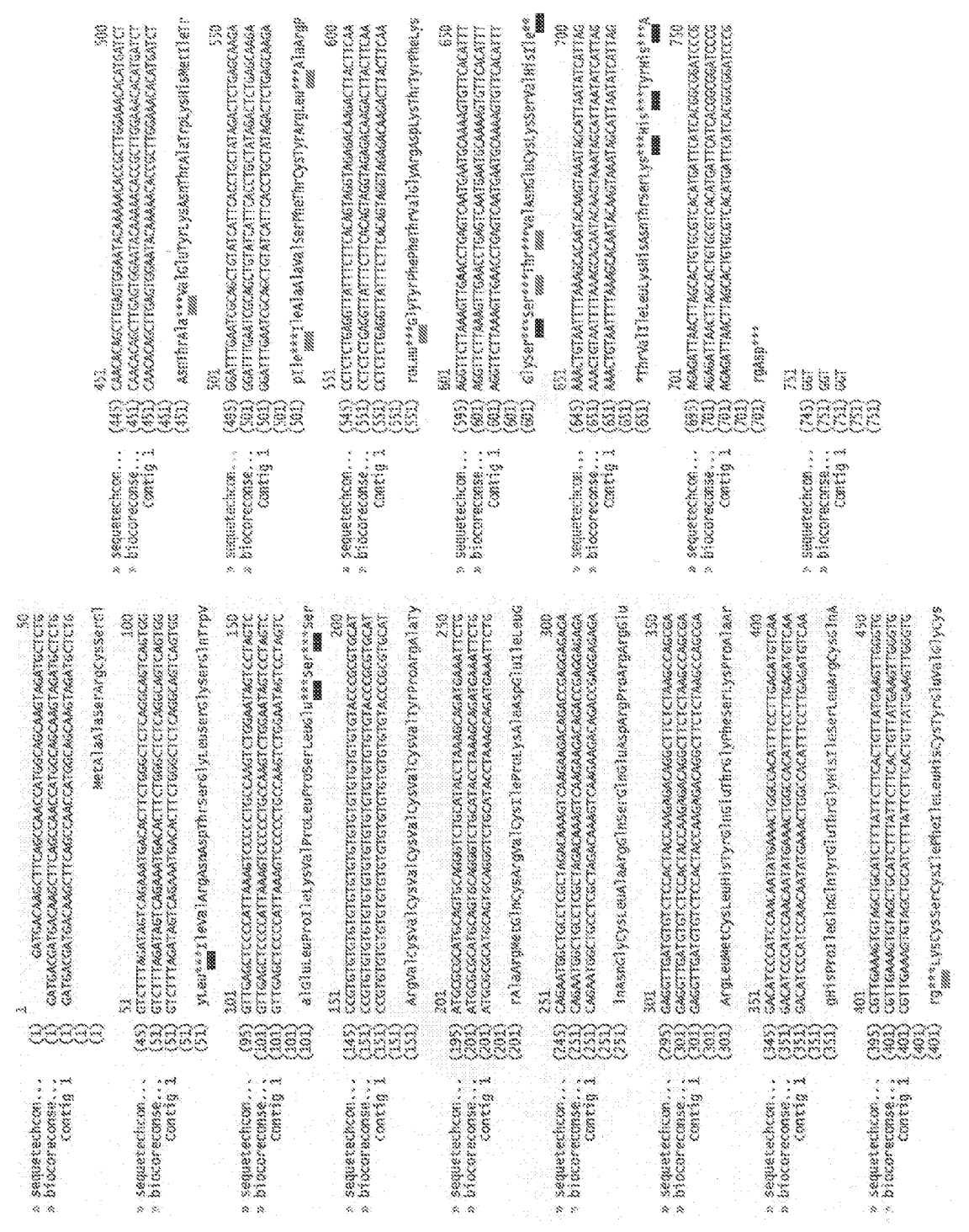

FIGS. 7A and 7B show, according to exemplary aspects of the present invention, that the Mig-7 sequence that produced protein in vivo contains multiple stop codons in reading frame "0". Plasmids were produced and grown as previously described in FIG. 5, then sent to two different sequencing facilities, Texas Tech University Sequencing Core and Sequetech, Inc. Both facilities sequenced at least twice using two different overlapping primer sets in both directions each. (A) Representative sequencing scheme of overlapping and complementary strand sequencing. FIG. 7B (SEQ ID NOs: 32, 45) shows that the consensus sequences from each facility are 100% homologous. Stop codons are indicated with asterisks in the predicted amino acid sequence from reading frame "0". Green highlights are UGA that can also encode for selenocysteine. Red highlights are UAG or UAA stop codons.

FIGS. 8A-8E (SEQ ID NOs: 43, 44, 45, 46) show, according to exemplary aspects of the present invention, that the Mig-7 sequence contains a predicted shift-site and pseudoknot indicating potential frame-shifting, and that Mig-7 protein levels are increased with polyamine treatment consistent with recoding during translation.

FIGS. 9A, 9B and 9C show, according to exemplary aspects of the present invention, and in view of the proposed shift −1 or +1 in reading frame at slippery or "shifty" sites (e.g., a shift of −1 or +1 in the reading frame after the ninth amino acid of Mig-7), three potential reading frames (−1, 0, +1) for the corresponding Mig-7 encoding sequences (SEQ ID NO:35, 36 and 37). FIG. 9A shows the 0-frame, FIG. 9B shows the +1-shifted frame, and FIG. 9C shows the −1-shifted frame.

FIG. 11A shows a representative Western blot analysis of integrin β5 expression by HT29, FG and RL95 cells. HT29 are negative while FG and RL95 are positive for β5. FIG. 11B shows representative Northern blot analysis demonstrated that EGF and IGF-1 induce Mig-7 expression in β5+FG pancreatic carcinoma cells. RL95 cells express β5 and Mig-7[1]. FIG. 11C shows that relative RT-PCR revealed that HT29 cells do not express Mig-7 mRNA. Each experiment was performed 3 times with similar results.

FIG. 13A shows that HT29 cells transfected with 3×CMVFLAG-Mig-7 expression vector express the same sized protein detected by anti-FLAG antibody as does the affinity purified Mig-7 antibody of endogenous Mig-7 in HEC1A cell lysates. Cells were plated on Matrigel for 17, 48 and 72 hours. Empty vector transfected HT29 cells are negative for FLAG Mig-7 as are parental HT29. FIG. 13B shows that HT29 Mig-7 expressing cells are >30% less adherent to a mix of laminins 1, 2, 3, 6, 8 & 10 in a statistically significant manner (p<0.001). FIG. 13C shows that HT29 cells with empty vector form discrete colonies in 3D Matrigel cultures (left panel). In contrast, HT29 cells expressing FLAG Mig-7 invade and form vessel structures (right panel and inset, supplemental data). All experiments were performed at least twice (3D cultures three times) in quadruplicate.

DETAILED DESCRIPTION OF THE INVENTION

Definitions

Figure 2:
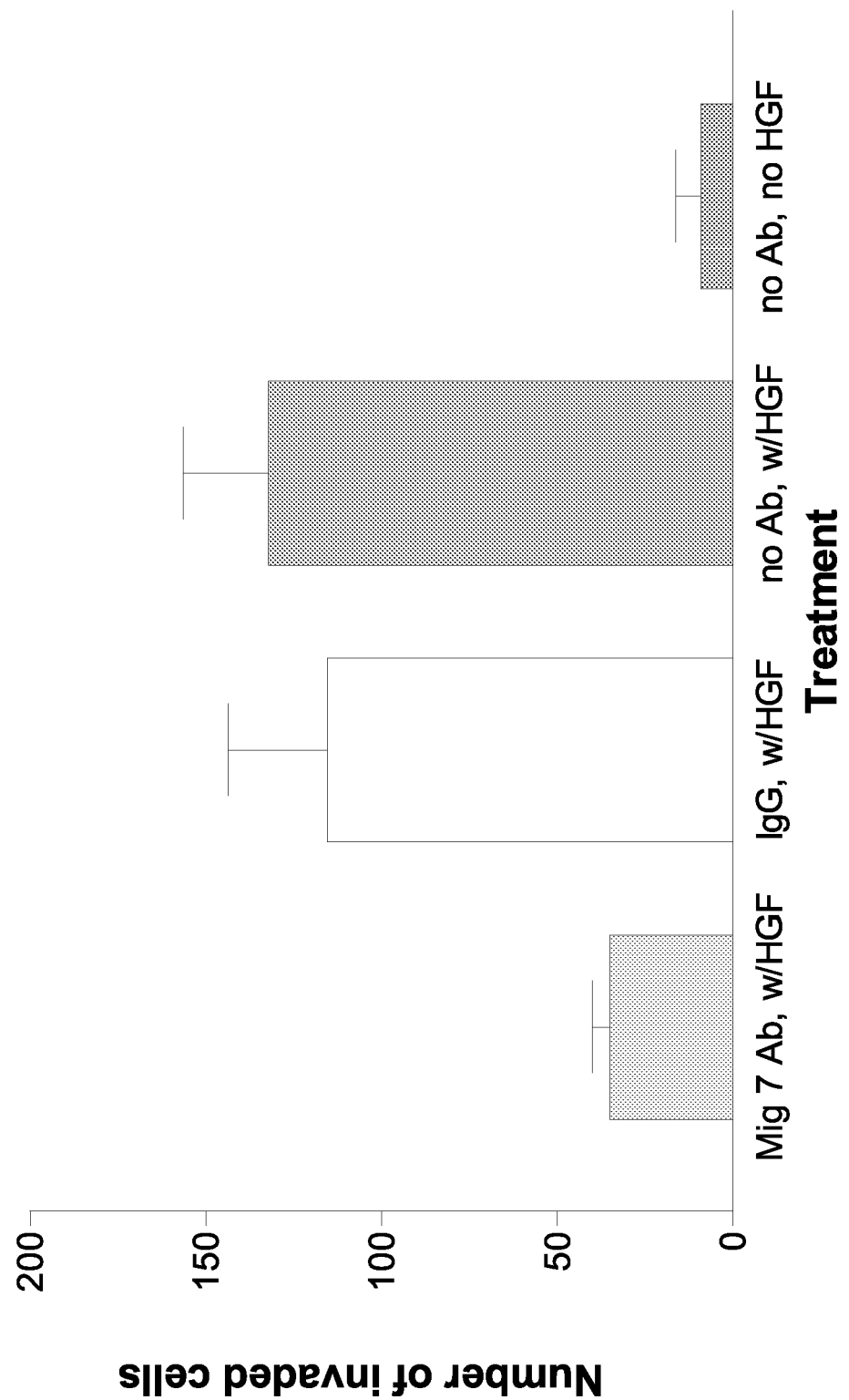
FIG. 2 shows, according to exemplary aspects of the present invention, that antibody specific to Mig-7 inhibits HEC1A endometrial carcinoma chemoinvasion. Mig-7 affinity purified antibody but not IgG isotype antibody significantly decreased chemoinvasion of HEC1A cells into Matrigel. Experiments were performed in triplicate for each treatment and repeated three times.

"Protective immunity" refers to the art-recognized protective immunity by a host, the immunity having been induced within the host by one or more prior vaccinations, or by one or more prior pathogen infections.

"Passive immunity" or "Immediate immunity" refers to the immunity conferred within a host, by passive antibody administration, wherein, passive antibody can theoretically confer protection regardless of the immune status of the host. Passive antibody administration can be used for post-exposure prophylaxis.

The term "epitope" refers herein, as is known in the art, to an antigenic determinant of a protein of polypeptide. An epitope could comprise 3 amino acids in a special conformation which is unique to the epitope. Generally an epitope consists of at least 5 such amino acids. An epitope of a polypeptide or protein antigen can be formed by contiguous or noncontiguous amino acid sequences of the antigen. A single viral protein, for example, may contain many epitopes. Additionally, a polypeptide fragment of a viral protein may contain multiple epitopes. The present invention encompasses epitopes and/or polypeptides recognized by antibodies of the present invention, along with conservative substitutions thereof, which are still recognized by the antibodies. Further truncation of these epitopes may be possible.

"ELISA" refers to enzyme-linked immuno sorbent assays, as widely recognized in the art, and as described herein.

"Immunologic assay," as used herein refers to an art-recognized immunologic assay suitable to detect the formation of antigen:antibody complexes, including, but not limited to antibody capture assays, antigen capture assays, and two-antibody sandwich assays, ELISA, immunodiffusion, immunoelectrophoresis, immunochemical methods, binder-ligand assays, immunohistochemical and immuncytochemical techniques, Western analysis, agglutination and complement assays (see e.g., Basic and Clinical Immunology, 217-262, Sites and Terr, eds., Appleton & Lange, Norwalk, Conn., 1991 which is incorporated herein by reference). Preferred embodiments (e.g., ELISA) of such assays are described herein below. According to the present invention, one or more of such immunoassays can be used to detect and/or quantitate antigens (e.g., Harlow & Lane, Antibodies: A Laboratory Manual; Cold Spring Harbor Laboratory, New York 555-612, 1988, incorporated by reference herein).

The term "treatment" refers to both therapeutic treatment and prophylactic or preventative measures, wherein the object is to prevent or slow (lessen) cancer, pathogens (e.g., viral) infection or associated conditions. Those in need of treatment include those already experiencing a condition or infection, those prone to the condition or infection, and also those in which the potential condition or infection is to be prevented.

"Antibodies," as used herein, refers to the art-recognized definition, and are described in more detail herein below.

"Neutralizing antibodies," as used herein, refers to the art-recognized definition.

"Cognate antigen," as used herein, refers to an antigen that is specifically bound by a cognate antibody, and "cognate antibody" refers to the antibody that specifically binds a cognate antigen.

"Vaccine," as used herein and in the art, refers to any type of biological agent in an administratable form capable of stimulating an immune response in an animal inoculated with the vaccine. For purposes of preferred embodiments of this invention, an inventive vaccine may comprise as the Mig-7 polypeptide agent, one or more immunogenic (antigenic) components of Mig-7, and including polypeptide-based vaccines.

Treating cancer has been hampered due to toxicity and other adverse side effects. As a result, cancer-specific instead of overexpressed targets are needed. Solid cancer cells and fetal trophoblasts express a novel gene called Migration inducting gene-7 (Mig-7) that is recoded from mRNA containing multiple stop codons and therefore not represented on any microarrays. Growth factors (e.g., epidermal, hepatocyte and insulin-like 1 growth factors) that are overexpressed by the tumor microenvironment, induce expression of Mig-7 in $\alpha v \beta 5$ integrin-positive cancer cells. Receptor tyrosine kinase activation and $\alpha v \beta 5$ integrin signaling are known to be required for tumor cell dissemination in vivo. Significantly, Mig-7 expression mediates tumor cell detection of the microenvironment, invasion and vessel-like structure formation in 3D cultures.

Because Mig-7 expression is specific to solid cancer cells in the adult and plays a role in aggressive tumor cell behavior, the present Applicant conceived that Mig-7 expression provides for a cancer-specific target allowing for novel diagnostic/prognostic and/or therapeutic compositions and methods that will inhibit the spread of cancer while preventing damage to normal cells.

According to particular aspects, Mig-7 is a pan-solid cancer cell target, and targeting Mig-7 in anticancer therapies provides novel therapies specific to tumor cells while sparing normal cells, and enabling higher effective doses with fewer side-effects.

According to additional aspects, Mig-7 is a pan-carcinoma expression marker for cancer diagnosis and/or prognosis, as well as a pan-carcinoma therapeutic target for cancer therapies.

Significantly, art-recognized in vitro model systems of invasion and tumor cell killing were employed herein to confirm Mig-7 is a pan-solid cancer cell target, and a pan-carcinoma expression marker for cancer diagnosis and/or prognosis.

Specifically, as disclosed herein (see working Example 1 herein), antisense or antibody specific to Mig-7 significantly reduced chemoinvasion by >60%. Additionally, breast carcinoma cell killing was significantly enhanced by stimulating isolated, human monocyte cells with Mig-7 peptides in vitro.

Example 1 herein shows, inter alia, a demonstration of the efficacy and importance of targeting Mig-7, both in vitro and in vivo. In the context of Example 1, the Applicant points out that targeting mRNA with antisense oligonucleotides or with RNAi thereby inhibiting translation and downstream functions of overexpressed tumor cell proteins has been shown to be a viable therapy to decrease tumor progression (11-15). However, to date, none of these targets are cancer-specific and ultimately in vivo toxicity as well as negative effects on normal cells occur. The present Applicant speculated that targeting Mig-7 would allow higher, more effective doses, and because of its specific expression in cancer cells, Mig-7 antagonists (e.g., antisense or RNAi, etc.) would not affect normal cells.

Additionally, anti-cancer antibody therapies are one of the newest targeting approaches. For example, Herceptin® (Trastuzumab), an antibody therapy, targets HER2, an EGF receptor that is overexpressed in approximately 20% of breast cancer patients. In clinical trials of over 3,000 breast cancer patients positive for overexpression and after a median follow-up of 23 months, 13.7% of women treated with doxorubicin and cyclophosphamide then by docetaxel suffered recurrence or death, compared with 7.2% of women treated with doxorubicin and cyclophosphamide followed by docetaxel and trastuzumab (16). However, due to cardiac toxicity limitations, therapy may include shorter durations or lower doses (16). These types of anti-cancer therapy toxicities on normal cells could be avoided with a cancer cell-specific target such as Mig-7.

The data disclosed in the instant Example 1, indicate that antibody to Mig-7 peptide will be effective to inhibit invasion and metastasis in vivo. In addition, while agents such as Herceptin® (Trastuzumab) target only a fraction of breast cancers, Mig-7 is expressed in at least 96% (n=241) of all solid cancer types (2). Therefore, according to particular aspects of the present invention, Mig-7 antibodies provide for highly selective, pan-cancer therapies, that not only provide for a broad therapeutic scope and efficacy, but also provide for decreased treatment costs. Moreover, Mig-7 antagonists (e.g., antibodies, etc,) can be used alone, or in combination with current anti-growth factor therapies.

As shown in Applicant's Example 1, using Mig-7 as a target decreases chemoinvasion and enhances stimulation of Human peripheral blood monocytes (MC) to produce cells that lyse MCF-7 tumor cells, and to produce TNF-α in vitro. Enhanced killing indicates that Mig-7 is a tumor antigen target of stimulated human MC, and thus provides proof that Mig-7 possesses tumor specific epitopes recognized by human MC. In addition, these experiments show that Mig-7 peptides combined with MUC1 are superior in stimulating MC to kill MCF-7 cells. Furthermore, Mig-7 peptides, but not irrelevant peptides, enhance production of TNF-α, an MC cytokine known to cause tumor cell death (17).

These results additionally indicate that inhibition of Mig-7 expression or function by antisense or by antibody treatments, respectively is suitable to inhibit carcinoma cell invasion in vivo.

In addition, peptides to Mig-7 may serve to enhance immunotherapies. Recently it has been shown that vaccine to human papilloma virus strains that prevent cervical cancer are virtually 100% efficacious (18). According to additional aspects of the present invention, Mig-7-specific peptides provide novel vaccine compositions, and inoculating with such Mig-7-specific peptide-based vaccines provides novel methods for pan-cancer inoculation and treatment. In addition, Mig-7 peptides may be used ex vivo to stimulate immune cells that can then be infused into a patient for carcinoma cell killing in vivo.

Example 2 herein shows that translation of the human carcinoma- and trophoblast-specific Mig-7 requires fidelity of the purine-pyrimidine repeat region and genetic recoding. Applicant demonstrates, surprisingly, that a cancer-specific, "noncoding" mRNA produces protein when using Applicant's combination of techniques. Migration inducing gene-7 (Mig-7) is unique in its induction, translation and detection making it highly cancer cell-specific. In Example 2, the Applicant details novel requirements for Mig-7 cloning and expression as well as relationship of these techniques to tumor progression. These techniques help elucidate the unique, tumor- and fetal/embryonic trophoblast-specific expression for use as a novel biomarker (e.g., diagnostic, and/or prognostic marker) and as a therapeutic target for cancer therapies.

The data of Example 2 indicate that the Mig-7 protein encoding sequence contains stop codons. The data further indicate that Mig-7 mRNA contains predicted slippery and pseudoknot motifs that are known in other sequences to allow frameshifting and read through of stop codons.

As described herein (Example 2), according to particular aspects, protein/polypeptide embodiments of the invention not only encompass a polypeptide according to SEQ ID NO:32 and contiguous portions thereof, but additionally encompasses polypeptides comprising the first nine amino acids MAASRCSGL (SEQ ID NO:31), followed by one or more frame-shifted amino acid sequence selected from SEQ ID NOS:32, 33 and 34.

In preferred aspects, after the ninth amino acid, the +1-reading frame (from MAASRCSGL (SEQ ID NO:31) in the O-frame to SEMTLL . . . or to RSMTLL . . . or to MTLL in the +1-frame) is used, because this frameshift results in fewest downstream stops. This frame also contains a peptide that caused an increase breast carcinoma cell killing by peptide-stimulated monocytes from cancer patients in vitro, and overlapping peptides specific to this frame stimulate human peripheral blood monocyte killing of MCF-7 breast carcinoma cells in vitro in a statistically significant manner (see Example 1 herein). The TAG stop in line 542 can be read through or frame shifted through, with the double-stop located between nucleotide positions 632 and 640 of SEQ ID NO:35 being the likely 'true stop' given the detected 23 kD sized protein in immunoblots. However, because there are shift sites (slippery or "shifty" sites) at those stops as well, the protein may extend beyond the double-stop position shifting onto a different frame and end at a subsequent stop codon located between the double-stop and the polyA additional site beginning at nucleotide position 757 of SEQ ID NO:35. All such proteins are encompassed herein.

Therefore, particular aspects of the invention provide a Mig-7 polypeptide frame-shift or genetically recoded polypeptide encoded by SEQ ID NO:1 and comprising an amino-terminal MAASRCSGL (SEQ ID NO:31) sequence. In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS: 32, 33, 34, 41, 42).

Preferably, the amino-terminal MAASRCSGL (SEQ ID NO:31) sequence is linked to at least one amino acid sequence selected from the group consisting of SEQ ID NOS:32, 33, 34, and contiguous portions thereof In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS:32, 33, 34, 41, 42).

Preferably, the amino-terminal MAASRCSGL (SEQ ID NO:31) sequence is linked to at least one amino acid sequence selected from the group consisting of SEQ ID NOS:33, 34, and contiguous portions thereof. In particular aspects, the polypeptide is from about 203 to about 207 amino acid residues in length (SEQ ID NO:46, 47). In particular aspects, the polypeptide is from about 223 to about 240 amino acid residues in length (SEQ ID NOS:32, 33, 34, 41, 42).

Preferably, the amino-terminal MAASRCSGL (SEQ ID NO:31) sequence is linked to at least one amino acid sequence selected from the group consisting of SEQ ID NOS:40, 41 and contiguous portions thereof as shown in SEQ ID NO:46 from FIG. 8C. In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS:32, 33, 34, 41, 42).

Working Example 3 herein shows that expression of Mig-7 allowed cancer cells to sense a 3D environment, to invade and to form vessel structures. Because carcinoma and cytotrophoblast both engage in vasculogenic mimicry, in this Example the Applicant tested and confirmed the hypothesis that Mig-7 is also expressed by fetal/embryonic cytotrophoblasts and plays a role in their common cell behaviors of invasion and vessel formation. Importantly, 3-D cultures revealed that Mig-7 expression causes invasion and vessel formation. Adhesion assays to various components of the extracellular matrix suggests that a mechanism for Mig-7 in vessel formation by tumor cells is due to less adhesion to laminin. This Example provides further support for the efficacy of targeting Mig-7 in cancer therapies. The facts that Mig-7 is induced by growth factors that regulate PI3K, a signaling pathway required for vasculogenic mimicry, is localized to vessels in metastases, causes vessel-like formation and less adherence to laminin, collectively indicate that Mig-7 expression serves to allow cells to sense their environment, to invade and to cause vasculogenic mimicry. Therefore, according to particular aspects, Mig-7 provides a molecular target for therapies to modulate tumor progression.

Peptide-based Vaccines:

Peptide-based vaccines are well known in the art, and may contain additional antigenic and adjuvant elements. Peptide-based vaccine are advantageous over traditional vaccines for several reasons: they are substantially safer; they have a relatively long shelf-life; they have the ability to target the immune response towards specific epitopes that are not suppressive nor hazardous for the host; and they offer the possibility of preparing multi-component and multi-pathogen vaccines.

The efficacy of inventive peptide-based vaccines are enhanced by adequate presentation of the epitopes to the immune system. Therefore, in preferred aspects, the Mig-7 based polypeptides or epitopes are couple to, or are expressed (e.g, hydrid-gene expression) as part of, a carrier that may also offer an adjuvant function. Additional adjuvants may or may not be included in the immunization.

In particular aspects, immunizations are performed with one or more Mig-7 polypeptides as disclosed herein.

Antibodies. In particular embodiments, Mig-7 polypeptides have utility for developing respective antibodies (e.g., monoclonal antibodies), and compositions comprising such antibodies.

Such antibodies and compositions have utility as novel diagnostic reagents for directly detecting the respective condition (e.g., cancer). The diagnostic assays are rapid, high-throughput and suitable for 'point-of-care' implementations.

Diagnostic assays. Particular aspects of the present invention thus provide a high-throughput method for detecting cancer, comprising: obtaining a test sample from a test subject; and detecting Mig-7 in the sample using an immunologic assay based, at least in part, on use of at least one antibody reagent, or epitope-binding portion thereof, specific for a Mig-7 protein or polypeptide antigen as disclosed herein.

In particular embodiments, the immunologic assay is selected from the group consisting of ELISA, immunoprecipitation, immunocytochemistry, immunoelectrophoresis, immunochemical methods, Western analysis, antigen-capture assays, two-antibody sandwich assays, binder-ligand assays, agglutination assays, complement assays, and combinations thereof. In particular embodiments, the antibody is selected from the group consisting of a single-chain antibody, a monoclonal antibody, a chimeric antibody, a humanized antibody, and a Fab fragment. In particular embodiments, a plurality of antibodies, or eptitope-binding portions thereof, are used, in each case specific for an Mig-7 protein or polypeptide antigen as disclosed herein.

Therapeutic agents. Additionally, because of the nature of the relevant specific binding interactions, antibodies and antibody-containing compositions of the present invention have therapeutic utility for treatment or prevention of cancer. The inventive antibodies and antibody compositions have utility for treating cancer, for alleviating symptoms of cancer, and/or to prevent cancer. Preferably, the antibodies and antibody compositions are directed against Mig-7 epitopes, and can be used to treat or prevent cancer by administration to subjects in need thereof.

Specifically, particular embodiments of the present invention provide an antibody directed against a Mig-7 protein or polypeptide antigen as disclosed herein.

In particular embodiments, the antibody is a monoclonal antibody, or antigen-binding portion thereof. In particular embodiments, the monoclonal antibody, or antigen-binding portion thereof, is a single-chain antibody, chimeric antibody, humanized antibody or Fab fragment.

Additional aspects provide a composition, comprising at least one of the above-described antibodies. Preferably, the composition comprises a Mig-7-specific monoclonal antibody. Preferably, at least one of the antibodies forms specific immunocomplexes with Mig-7 proteins or polypeptides associated with cancer cells.

Yet further aspects provide a pharmaceutical composition, comprising at least one of the above-described antibodies, along with a pharmaceutically acceptable diluent, carrier or excipient. Preferably, the composition is administered to a subject, whereby the composition prevents or inhibits cancer. In particular embodiments, the composition is administered to a subject, whereby the composition ameliorates symptoms of cancer. In particular embodiments, at least one of the antibodies of the composition forms specific immunocomplexes with Mig-7 proteins or polypeptides associated with cancer cells.

Yet further aspect provide a method of treating, or of preventing cancer, comprising administering to a subject in need thereof, a therapeutically effective amount of at least one of the above-described antibodies, or of a pharmaceutical composition comprising at least one of the antibodies. In particular embodiments, the immunoglobulin sequences are, or substantially are, human immunoglobulin sequences.

Arrays. Yet further embodiments provide an array of different Mig-7 proteins or polypeptides epitopes (oligopeptides) immobilized on a solid phase. The term "microarray" refers broadly to both 'polypeptide microarrays' and 'polypeptide chip(s),' and encompasses all art-recognized solid supports, and all art-recognized methods for synthesizing polypeptides on, or affixing polypeptides molecules thereto. The solid-phase surface may comprise, from among a variety of art-recognized materials, silicon, glass, polystyrene, aluminum, steel, iron, copper, nickel, silver, gold or cellulose. However, nitrocellulose as well as plastics such as nylon, which can exist in the form of pellets or also as resin matrices, may also be used.

It is also anticipated that the oligopeptides, or particular sequences thereof, may constitute all or part of an "virtual array" wherein the oligopeptides, or particular sequences thereof, are used, for example, as 'specifiers' as part of, or in combination with a diverse population of unique labeled oligopeptides to analyze a complex mixture of analytes. In such methods, enough labels are generated so that each antibody in the complex mixture (i.e., each analyte) can be uniquely bound by a unique label and thus be detected (e.g., each label may be directly counted, resulting in a digital read-out of each molecular species in the mixture).

Preferred embodiments provide an array comprising a plurality of different Mig-7 proteins or polypeptides coupled to a solid phase.

Preferably, the solid phase comprises a material selected from the group consisting of silicon, cellulose, glass, polystyrene, polyacrylamide, aluminum, steel, iron, copper, nickel, silver, gold and combinations thereof.

Immunologic Assays

According to the present invention, numerous art-recognized competitive and non-competitive protein binding immunoassays are used to detect and/or quantify antigens or antibodies (e.g., Harlow & Lane, Antibodies: A Laboratory Manual; Cold Spring Harbor Laboratory, New York 555-612, 1988). Such immunoassays can be qualitative or and/or quantitative, and include, but are not limited to antibody capture assays, antigen capture assays, and two-antibody sandwich assays, immunodiffusion, immunoelectrophoresis, immunochemical methods, binder-ligand assays, immunohistochemical techniques, agglutination and complement assays (e.g., *Basic and Clinical Immunology*, 217-262, Sites and Terr, eds., Appleton & Lange, Norwalk, Conn., 1991 which is incorporated herein by reference). Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Antibody capture assays comprise immobilizing an antigen on a solid support, and contacting the immobilized antigen with an antibody-containing solution, whereby antigen-specific antibody, if present, binds to the immobilized antigen. The antibodies can be labeled or unlabeled. Antigen attachment to the solid support is typically non-covalent, but might in particular instances be covalent. After washing the support, antibody retained on the solid support is detected, or quantified by measuring the amount thereof. ELISA assays represent preferred embodiments of immunologic antibody capture assays as used herein. Competitive ELISA assays represent a preferred embodiment of antibody capture assay, wherein the antigen is bound to the solid support and two antibodies which bind the antigen are allowed to compete for binding of the antigen. The amount of monoclonal antibody bound is measured, and a determination made as to whether the serum contains the cognate antigen antibodies. Such ELISAs can be used to indicate immunity to known protective epitopes in a vaccinee following vaccination.

Antigen capture assays comprise immobilizing an antibody to a solid support, and contacting the immobilized antibody with an antigen-containing solution, whereby antibody-specific antigen, if present, binds to the immobilized antibody. The antigens can be labeled or unlabeled. Antibody attachment to the solid support is typically non-covalent, but might in particular instances be covalent. After washing the support, antigen retained on the solid support is detected, or quantified by measuring the amount thereof.

Two-antibody sandwich assays (e.g., in the context of an antigen-capture assay) comprise initially immobilizing a first antigen-specific antibody on a solid support, followed by contacting the immobilized antibody with antigen-containing solution, washing the support, and subsequently detecting or quantifying the amount of bound antigen by contacting the immobilized antibody-antigen complexes with a second antigen-specific antibody, and measuring the amount of bound second antibody after washing.

Generally, immunoassays rely on labeled antigens, antibodies, or secondary reagents for detection. These proteins (antigens or antibodies) can be labeled with radioactive compounds, enzymes (e.g. peroxidase), biotin, or fluorochromes, etc. Enzyme-conjugated labels are particularly useful when radioactivity must be avoided, and provides for relatively rapid results. Biotin-coupled reagents are typically detected with labeled streptavidin. Streptavidin binds tightly and quickly to biotin and can be labeled with radioisotopes or enzymes. Fluorochromes, provide a very sensitive method of detection. Antibodies useful in these assays include, but are not limited to, monoclonal antibodies, polyclonal antibodies, affinity-purified polyclonal antibodies, and antigen or epitope-binding fragments of any of these. Labeling of antibodies or fragments thereof can be accomplished using a variety of art-recognized techniques (e.g., Kennedy et al., *Clin. Chim. Acta.*, 70:1-31, 1976; Schurs et al., *Clin. Chim Acta.*, 81:1-40, 1977; both incorporated by reference herein). Coupling techniques include, but are not limited to the glutaraldehyde, periodate method, dimaleimide and other methods.

ELISA. Enzyme-linked immunosorbent assay (ELISA) systems are widely recognized in the art, and are commonly used to detect antibodies in, for example, serum samples. For detection of antibodies in serum, a serum sample, or diluted serum sample, is applied to a surface (e.g. a well of a microtiter plate, preferably 'blocked' to reduce non-specific protein binding) having immobilized antigens (epitope(s)) thereon. Serum antibodies specific for the immobilized epitope(s) bind with high affinity to the immobilized epitope(s) on the plate, and are retained after standard washes, whereas non-specific antibodies do not bind with high affinity, and are removed after standard washes.

Specifically bound antibody is detected, for example, by using enzyme-coupled anti-immunoglobulins and a chromogen (e.g., horseradish peroxidase-conjugated antibodies used in combination with hydrogen peroxide). The enzyme which is bound to the antibody will react with an appropriate substrate, preferably a chromogenic substrate, in such a manner as to produce a chemical moiety which can be detected, for example, by spectrophotometric, fluorimetirc or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

The detection can be accomplished by calorimetric methods that employ a chromogenic substrate for the enzyme. Detection may also be accomplished visually by comparison of the extent of enzymatic reaction with appropriate standards. Detection may also be accomplished using any of a variety of other immunoassays. For example, by radioactively labeling the antibodies or antibody fragments, it is possible to detect antigenic peptides through the use of a radioimmunoassay (RIA). The radioactive isotope can be detected by such means as the use of a gamma counter or a scintillation counter or by autoradiography. It is also possible to label the antibody with a fluorescent compound. When the fluorescently labeled antibody is exposed to light of the proper wavelength, its presence can be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Generation and Production of Antibodies

Polyclonal or monoclonal antibodies to Mig-7 proteins and polypeptides or to epitope-bearing fragments thereof can be made for therapeutic, or diagnostic (e.g., immunoassays) use by any of a number of methods known in the art. By epitope reference is made to an antigenic determinant of a polypeptide. An epitope could comprise 3 amino acids in a spatial conformation which is unique to the epitope (methods of determining the spatial conformation of amino acids are known in the art, and include, for example, x-ray crystallography and 2 dimensional nuclear magnetic resonance). Generally an epitope consists of at least 5 such amino acids. The present invention encompasses epitopes and/or polypeptides recognized by antibodies of the present invention, along with conservative substitutions thereof, which are still recognized by the antibodies.

One approach for preparing antibodies to a protein is the selection and preparation of an amino acid sequence of all or part of the protein, chemically synthesizing the sequence and injecting it into an appropriate animal, usually a rabbit or a mouse.

Oligopeptides can be selected as candidates for the production of an antibody to Mig-7 proteins or polypeptides based upon the oligopeptides lying in hydrophilic regions, which are thus likely to be exposed in the mature protein.

Alternatively, proteins and polypeptides can be selected by other art-recognized methods. Additionally, a combination of selection methods can be used.

Preferred proteins and polypeptides of the present invention are those of Mig-7, proteins and polypeptides and epitope-bearing fragments thereof.

In particular embodiments, the Mig-7 protein or polypeptide comprises at least one epitope of a sequence disclosed herein.

Methods for preparation of the Mig-7 proteins or polypeptides, or of an epitope thereof include, but are not limited to chemical synthesis, recombinant DNA techniques or isolation from biological samples. Chemical synthesis of a peptide can be performed, for example, by the classical Merrifield method of solid phase peptide synthesis (Merrifield, *J. Am. Chem. Soc.* 85:2149, 1963 which is incorporated by reference) or the FMOC strategy on a Rapid Automated Multiple Peptide Synthesis system (E. I. du Pont de Nemours Company, Wilmington, Del.) (Caprino and Han, *J Org Chem* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified Mig-7 proteins or polypeptides usually by ELISA or by bioassay based upon the ability to block the action of Mig-7 proteins or polypeptides. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495-497, 1975; Gulfre and Milstein, *Methods in Enzymology: Immunochemical Techniques* 73:1-46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating cancer and related disease. Thus, another aspect of the present invention provides for a method for preventing or treating cancer and related diseases involving treatment of a subject with specific antibodies to Mig-7 proteins or polypeptides.

Specific antibodies, either polyclonal or monoclonal, to the Mig-7 proteins or polypeptides can be produced by any suitable method known in the art as discussed above. For example, murine or human monoclonal antibodies can be produced by hybridoma technology or, alternatively, the Mig-7 proteins or polypeptides, or an immunologically active fragment thereof, or an anti-idiotypic antibody, or fragment thereof can be administered to an animal to elicit the production of antibodies capable of recognizing and binding to the Mig-7 proteins or polypeptides. Such antibodies can be from any class of antibodies including, but not limited to IgG, IgA, IgM, IgD, and IgE or in the case of avian species, IgY and from any subclass of antibodies.

The present invention further provides for methods to detect the presence of the Mig-7 proteins or polypeptides in a sample obtained from a patient. As discussed above under "Immunologic Assays," any method known in the art for detecting proteins can be used. Such methods include, but are not limited to immunodiffusion, immunoelectrophoresis, immunochemical methods, binder-ligand assays, immunohistochemical techniques, agglutination and complement assays. (for example, see *Basic and Clinical Immunology*, 217-262, Sites and Terr, eds., Appleton & Lange, Norwalk, Conn., 1991 which is incorporated by reference). Preferred are ELISA methods, including reacting antibodies with an epitope or epitopes of the Mig-7 proteins or polypeptides.

As provided herein, the compositions and methods for diagnosis/detection of cancer, or the therapeutic methods of treatment or prevention provided herein, may utilize one or more antibodies used singularly, or in combination with other therapeutics to achieve the desired effects. Antibodies according to the present invention may be isolated from an animal producing the antibody as a result of either direct contact with an environmental antigen or immunization with the antigen. Alternatively, antibodies may be produced by recombinant DNA methodology using one of the antibody expression systems well known in the art (see, e.g., Harlow & Lane, Antibodies: A Laboratory Manual, Cold Spring Harbor Laboratory (1988). Such antibodies may include recombinant IgGs, chimeric fusion proteins having immunoglobulin derived sequences or "humanized" antibodies that may all be used according to the present inventive aspects. In addition to intact, full-length molecules, the term antibody also refers to fragments thereof (e.g., scFv, Fv, Fd, Fab, Fab' and F(ab)'$_2$ fragments), or multimers or aggregates of intact molecules and/or fragments that bind to the inventive antigens (proteins/polypeptides/epitopes). These antibody fragments bind antigen and may be derivatized to exhibit structural features that facilitate clearance and uptake (e.g., by incorporation of galactose residues).

In particular embodiments antibodies are monoclonal antibodies, prepared essentially as described in Halenbeck et al. U.S. Pat. No. 5,491,065 (1997), incorporated herein by reference.

Additional embodiments comprise humanized monoclonal antibodies. The phrase "humanized antibody" refers to an antibody initially derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, for example, Jones et al., *Nature* 321:522-525, 1986; Morrison et al., *Proc. Natl. Acad. Sci., U.S.A.*, 81:6851-6855, 1984; Morrison and Oi, *Adv. Immunol.*, 44:65-92, 1988; Verhoeyer et al., *Science* 239:1534-1536, 1988; Padlan, *Molec. Immun.* 28:489-498, 1991; Padlan, *Molec. Immunol.* 31(3):169-217, 1994; and Kettleborough, C. A. et al., *Protein Eng.* 4(7):773-83, 1991, each of which is incorporated herein by reference.

The phrase "complementarity determining region" refers to amino acid sequences which together define the binding affinity and specificity of the natural Fv region of a native immunoglobulin binding site (see, e.g., Chothia et al., *J. Mol. Biol.* 196:901-917, 1987; Kabat et al., U.S. Dept. of Health and Human Services NIH Publication No. 91-3242, 1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance (e.g., via Ashwell receptors) (see, e.g., U.S. Pat. Nos. 5,530,101 and 5,585,089, both incorporated herein by reference).

Humanized antibodies to the inventive proteins can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735; disclosing monoclonal antibodies against a variety of antigenic molecules including IL-6, IL-8, TNFa, human CD4, L-selectin, gp39, and tetanus toxin. The monoclonal antibodies can be tested for the ability to inhibit or neutralize the biological activity or physiological effect of the corresponding protein or pathogenic agent (e.g., virus). WO 96/3373 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096. The antibodies of the present invention are said to be immuospecific, or specifically binding, if they bind to the Mig-7 antigen (protein/polypeptide/epitope) with a $K_a$ of greater than or equal to about $10^4 M^{-1}$, preferably of greater than or equal to about $10^5 M^{-1}$, more preferably of greater than or equal to about $10^6 M^{-1}$, and still more preferably of greater than or equal to about $10^7 M^{-1}$. Such affinities may be readily determined using conventional techniques, such as by equilibrium dialysis; by using the BIAcore 2000 instrument, using general procedures outlined by the manufacturer; by radioimmunoassay using $^{125}$I-labeled proteins; or by another method known to the skilled artisan. The affinity data may be analyzed, for example, by the method of Scatchard et al., *Ann N.Y. Acad. Sci.*, 51:660, 1949. Thus, it will be apparent that preferred antibodies will exhibit a high degree of specificity for the Mig-7 antigen of interest, and will bind with substantially lower affinity to other molecules.

Preferably the anti-pathogenic antibodies of the present invention are monoclonal antibodies. More preferably, the antibodies are humanized monoclonal antibodies.

Biologically Active Variants

Variants of Mig-7 polypeptides have substantial utility in various aspects of the present invention. Variants can be naturally or non-naturally occurring. Naturally occurring variants are found in humans or other species and comprise amino acid sequences which are substantially identical to the amino acid sequences shown herein, and include natural sequence polymorphisms. Species homologs of the protein can be obtained using subgenomic polynucleotides of the invention, as described below, to make suitable probes or primers for screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants, including the Mig-7 activities disclosed herein and the modulation of target signaling activity, are also included here. Preferably, naturally or non-naturally occurring variants have amino acid sequences which are at least 85%, 90%, or 95% identical to the amino acid sequence shown herein. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243: 3552-59 (1969) and adopted at 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Guidance in determining which amino acid residues can be substituted, inserted, or deleted without abolishing biological or immunological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

Such substitutions may be made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

Variants of the Mig-7 polypeptide disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins (Mark et al., U.S. Pat. No. 4,959,314).

Preferably, amino acid changes in the Mig-7 polypeptide variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of Mig-7 polypeptide protein or polypeptide variants are of the same type as a protein comprising the amino acid sequence encoded by the nucleotide sequences shown herein, although the properties and functions of variants can differ in degree.

Mig-7 polypeptide variants include glycosylated forms, aggregative conjugates with other molecules, and covalent conjugates with unrelated chemical moieties (e.g., pegylated molecules). Mig-7 polypeptide variants also include allelic variants (e.g., polymorphisms), species variants, and muteins. Truncations or deletions of regions which do not preclude functional activity of the proteins are also variants. Covalent variants can be prepared by linking functionalities to groups which are found in the amino acid chain or at the N- or C-terminal residue, as is known in the art.

It will be recognized in the art that some amino acid sequence of the Mig-7 polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors (Ostade et al., *Nature* 361:266-268, 1993). Thus, the Mig-7 polypeptides of the present invention may include one or more amino acid substitutions, deletions or additions, either from natural mutations or human manipulation.

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic (Pinckard et al., *Clin. Exp. Immunol.* 2:331-340, 1967; Robbins et al., *Diabetes* 36:838-845, 1987; Cleland et al., *Crit. Rev. Therapeutic Drug Carrier Systems* 10:307-377, 1993).

Amino acids in the Mig-7 polypeptides of the present invention that are essential for function can be identified by methods known in the art, such as site-directed mutagenesis or alanine-scanning mutagenesis (Cunningham and Wells, *Science* 244:1081-1085, 1989). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904, 1992 and de Vos et al. Science 255:306-312, 1992).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given Mig-7 polypeptide will not be more than 50, 40, 30, 25, 20, 15, 10, 5 or 3.

In addition, pegylation of Mig-7 polypeptides and/or muteins is expected to provide such improved properties as increased half-life, solubility, and protease resistance. Pegylation is well known in the art.

Fusion Proteins

Fusion proteins comprising proteins or polypeptide fragments of Mig-7 polypeptides can also be constructed. Fusion proteins are useful for generating antibodies against amino acid sequences and for use in various targeting and assay systems. For example, fusion proteins can be used to identify proteins which interact with a Mig-7 polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the amino acid sequence shown herein (e.g., contiguous amino acid residues corresponding to different reading frames of the Mig-7 coding sequence; frame-shift protein variants, etc) or can be prepared from biologically active variants thereof. The first protein segment can include a full-length Mig-7 polypeptide.

Other first protein segments can consist of amino acid sequence selected from the group consisting of SEQ ID NOS: 38, 39, 40, 41, 42, fragments of SEQ ID NOS:38 and 39 of about 17 to 85 contiguous residues in length, and fragments of SEQ ID NOS: 40, 41 and 42 of about 8 to 81 contiguous residues in length, and combinations thereof, wherein the polypeptide optionally comprises an amino terminal MAASRCSGL (SEQ ID NO:31) sequence.

The second protein segment can be a full-length protein or a polypeptide fragment. The second protein can be homologous or heterologous. Heterologous proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by the frame-shift process described herein for Mig-7 expression, or alternatively by covalently linking two protein segments or by standard procedures in the art of molecular biology. Recombinant DNA methods can be used to prepare fusion proteins, for example, by making a DNA construct which comprises a coding region for the Mig-7 protein sequence in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Cell Targeting

According to additional preferred aspects of the present invention, anti-Mig-7 antibodies can be used to target Mig-7 on cells (e.g., cancer cells, or fetal cytotrophoblast cells). Anti-Mig-7 antibody-based agents can be used to deliver a locally acting biological agent that will affect the targeted cell.

Mig-7 in the context of the inventive targeting, is expressed on the surface of cancer cells and is accessible. For example, where Mig-7 is present at higher levels on particular Mig-7-bearing cells (e.g., cancer cells, or fetal cytotrophoblast cells) as compared to other cells, they can be utilized as preferential targets for systemic anti-Mig-7 antibody-based agents and therapies. The differential expression of the target Mig-7 enables the specificity of anti-Mig-7 antibody-based agents. Anti-Mig-7 antibody-based agents (e.g., drugs, cytoxic agents, labeling agents, etc.) directed against the target Mig-7 preferentially affect the targeted cell over normal tissue. For example, an anti-Mig-7 antibody-drug conjugate that binds a Mig-7 present predominantly on particular cells (e.g., cancer cells, or fetal cytotrophoblast cells would be expected to selectively affect those cells within a treated individual. Preferably, the target Mig-7 is accessible to the anti-Mig-7 antibody-based agent, and is found in substantially greater concentrations on the targeted cells relative to other cells that don't express Mig-7 or that express Mig-7 or express at relatively low levels.

Therefore, the present invention includes anti-Mig-7 antibody-based agents specific to the Mig-7 target that will enable or facilitate therapeutic treatments relating to, for example, cancer cells, or fetal cytotrophoblast cells.

In particular aspects, Herstatin- and/or RBD Int8 polypeptides are conjugated or coupled to drugs, or to toxins.

In alternate embodiments, anti-Mig-7 antibodies, or antigen-binding fragments thereof are conjugated or coupled to radionuclides.

Additional embodiments provide for anti-Mig-7 antibody-coated liposomes that contain one or more biologically active compounds.

In preferred embodiments, anti-Mig-7 antibody-mediated targeting is used to deliver drugs or other agents to cancer cells, or fetal cytotrophoblast cells.

In alternate aspects, targeted binding of an anti-Mig-7 antibody-based agent to a cell is sufficient to modulate Mig-7-mediated signaling, inhibit or alter growth (e.g., cytostatic effects) or even kill the target cell (cytotoxic effects) if so desired. The mechanism of these activities may vary, but may involve Mig-7 polypeptide-dependent receptor activation, changes in receptor expression, cell-mediated cytotoxicity, activation of apoptosis, inhibition of ligand-receptor function, or provide a signal for complement fixation. In fact, anti-Mig-7 antibody-based agent may exhibit one or several such activities. In particular aspects, anti-Mig-7 antibody-based agent are cytostatic, but not cytotoxic. In particular embodiments, anti-Mig-7 antibody-based agent bind to Mig-7 targets, and modulate signaling and cellular metabolism, or are either cytoxic or cytostatic, etc.

In additional embodiments, anti-Mig-7 antibody-based agent are conjugated or coupled to a diverse array of compounds which include, but are not limited to proteins, drugs, toxins or cytotoxic agents, cytostatic agents, radionuclides, apoptotic factors (Wuest et al. 2002), anti-angiogenic compounds or other biologically active compounds which will affect cellular signaling or metabolism, inhibit the growth of or even kill the target cell or tissue. For example, cytotoxic or cytostatic agents include, but are not limited to, diphtheria toxin and *Pseudomonas* exotoxin (Kreitman 2001 a; Kreitman 2001 b), ricin (Kreitman 2001 a), gelonin, doxorubicin (Ajani et al. 2000) and its derivatives, iodine-131, yttrium-90 (Witzig 2001), indium-111 (Witzig 2001), RNase (Newton and Ryback 2001), calicheamicin (Bernstein 2000), apoptotic agents, and antiangiogenic agents (Frankel et al. 2000; Brinkmann et al. 2001; Garnett 2001). According to particular aspects of the present invention, anti-Mig-7 antibodies coupled to these compounds are used to adversely affect cells displaying Mig-7.

Toxins can also be targeted to specific cells by incorporation of the toxin into anti-Mig-7 antibody-coated liposomes. The anti-Mig-7 antibody-based agent directs the liposome to the target cell where the bioactive compound is released. For example, cytotoxins in anti-Mig-7 antibody-coated liposomes are used to treat cancer. In alternate embodiments, these targeted liposomes are loaded with DNA encoding bioactive polypeptides (e.g., inducible nitric oxide synthase; Khare et al. 2001).

Prodrugs or enzymes can also be delivered to targeted cells by specific anti-Mig-7 antibody-based agents. In this case the conjugate consists of a anti-Mig-7 antibody coupled to a drug that can be activated once the polypeptide agent binds the target cell. Examples of this strategy using antibodies have been reviewed (Denny 2001; Xu and McLeod 2001).

Therefore, in particular embodiments, anti-Mig-7 antibody-prodrug/enzyme conjugates that are targeted to one or more Mig-7 targets have utility for the treatment of, for example, cancer and other treatable conditions discussed herein.

The specificity and high affinity of the anti-Mig-7 antibody-based agents makes them ideal candidates for delivery of toxic agents to a specific subset of cellular targets. Preferably, one or more Mig-7 targets are exclusively present, or present at higher levels on the target cells (e.g., cancer, tumor cells) than on non-cancer cells.

As used herein, a composition refers to any mixture. It can be a solution, a suspension, liquid, powder, a paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof.

As used herein, a pharmaceutical effect refers to an effect observed upon administration of an agent intended for treatment of a disease or disorder or for amelioration of the symptoms thereof.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

In particular aspects, a therapeutic effect may also encompass prophylaxis of symptoms of a condition.

As used herein, the term "subject" refers to animals, including mammals, such as human beings. As used herein, a patient refers to a human subject.

As used herein, the phrase "associated with" or "characterized by" refers to certain biological aspects such as expression of a receptor or signaling by a receptor that occurs in the context of a disease or condition. Such biological aspects may or may not be causative or integral to the disease or condition but merely an aspect of the disease or condition.

As used herein, a biological activity refers to a function of a polypeptide including but not limited to complexation, dimerization, multimerization, receptor-associated kinase activity, receptor-associated protease activity, phosphorylation, dephosphorylation, autophosphorylation, ability to form complexes with other molecules, ligand binding, catalytic or enzymatic activity, activation including auto-activation and activation of other polypeptides, inhibition or modulation of another molecule's function, stimulation or inhibition of signal transduction and/or cellular responses such as cell proliferation, migration, differentiation, and growth, degradation, membrane localization, membrane binding, and oncogenesis. A biological activity can be assessed by assays described herein and by any suitable assays known to those of skill in the art, including, but not limited to in vitro assays, including cell-based assays, in vivo assays, including assays in animal models for particular diseases.

Pharmaceutical Compositions and Therapeutic Uses

Pharmaceutical compositions of particular aspects of the invention comprise one or more Mig-7 polypeptides, or anti-Mig-7 antibody-based agents of the claimed invention in a therapeutically effective amount. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the Mig-7 polypeptides, or anti-Mig-7 antibody-based agents in the individual to which it is administered. A non-limiting example of a pharmaceutical composition is a composition that either enhances or diminishes signaling mediated by the MIG-7 target. Where such signaling modulates a disease-related process, modulation of the signaling would be the goal of the therapy.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., New Jersey, 1991).

Delivery Methods

Once formulated, the compositions of the invention can be administered (as proteins/polypeptides, or in the context of expression vectors for gene therapy) directly to the subject or delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, myocardial, intratumoral, peritumoral, or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art and described in, for example, International Publication No. WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, direct microinjection of the DNA into nuclei, and viral-mediated, such as adenovirus (and adeno-associated virus) or alphavirus, all well known in the art.

In a preferred embodiment, certain disorders (e.g., of proliferation, such as cancer, etc), can be amenable to treatment by administration of a therapeutic agent based on the provided polynucleotide or corresponding polypeptide. The therapeutic agent can be administered in conjunction with one or more other agents including, but not limited to, receptor-specific antibodies and/or other agents (e.g., chemotherapeutic agents, etc). Administered "in conjunction" includes administration at the same time, or within 1 day, 12 hours, 6 hours, one hour, or less than one hour, as the other therapeutic agent(s). The compositions may be mixed for co-administration, or may be administered separately by the same or different routes.

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. The therapeutic polynucleotide composition can contain an expression construct comprising a promoter operably linked to a polynucleotide encoding a Mig-7 polypeptide. Various methods can be used to administer the therapeutic composition directly to a specific site in the body. For example, an abnormal tissue, or small metastatic lesion is located and the therapeutic composition injected several times in several different locations within the body of the tissue, or tumor. Alternatively, arteries which serve a tissue or tumor are identified, and the therapeutic composition injected into such an artery, in order to deliver the composition directly into the tumor. A tissue or tumor that has a necrotic center is aspirated and the composition injected directly into the now empty center of the tissue or tumor. X-ray imaging is used to assist in certain of the above delivery methods.

Mig-7 polypeptide, or anti-Mig-7 antibody-mediated targeted delivery of therapeutic agents to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (USA) (1990) 87:3655; Wu et al., *J. Biol. Chem.* (1991) 266:338.

For gene therapy, therapeutic compositions containing a polynucleotide are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the subgenomic polynucleotides. Where greater expression is desired over a larger area of tissue, larger amounts of subgenomic polynucleotides or the same amounts re-administered in a successive protocol of administrations, or several administrations to different adjacent or close tissue portions of, for example, a tumor site, may be required to affect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* 264:16985 (1989)); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell. Biol.* 14:2411 (1994), and in Woffendin, *Proc. Nat. Acad. Sci.* (1994) 91:11581-11585.

Further non-viral delivery suitable for use includes mechanical delivery systems such as the approach described in Woffendin et al., *Proc. Natl. Acad. Sci. USA* 91(24):11581 (1994). Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

The present invention will now be illustrated by reference to the following examples which set forth particularly advantageous embodiments. However, it should be noted that these embodiments are illustrative and are not to be construed as restricting the claimed invention in any way.

Example 1

Mig-7 was Shown to be a Specific Anti-cancer Therapeutic Target

Example overview. As shown in this Example, using Mig-7 as a target decreases chemoinvasion and enhances stimulation of Human peripheral blood monocytes (MC) to produce cells that lyse MCF-7 tumor cells, and to produce TNF-α in vitro. Enhanced killing indicates that Mig-7 is a tumor antigen target of stimulated human MC, and thus provides proof that Mig-7 possesses tumor specific epitopes recognized by human MC. In addition, these experiments show that Mig-7 peptides combined with MUC1 are superior in stimulating MC to kill MCF-7 cells. Furthermore, Mig-7 peptides, but not irrelevant peptides, enhance production of TNF-α, an MC cytokine known to cause tumor cell death (17).

These results additionally indicate that inhibition of Mig-7 expression by antisense or antibody treatment is suitable to inhibit carcinoma cell invasion in vivo.

In addition, peptides to Mig-7 may serve to enhance immunotherapies. Recently it has been shown that vaccine to human papilloma virus strains that prevent cervical cancer are virtually 100% efficacious (18). According to additional aspects of the present invention, Mig-7-specific peptides provide novel vaccine compositions, and inoculating with such Mig-7-specific peptide-based vaccines provides novel methods for pan-cancer inoculation and treatment. In addition, Mig-7 peptides may be used ex vivo to stimulate immune cells that can then be infused into a patient for carcinoma cell killing in vivo.

These data are shown, inter alia, to demonstrate the efficacy and importance of targeting Mig-7 in vivo.

Methods:

Cell cultures. HEC1A (1) and MCF7 (7) cells were cultured as previously described. Human isolated MC were cultured at $2 \times 10^6$ cells/ml in AIM-V® serum-free lymphocyte medium (Gibco BRL, Life Technologies, Inc. Grand Island, N.Y., USA) as previously described (7).

Modified Boyden chamber invasion assay. Chemoinvasion assays were preformed as previously described (8). Briefly, Costar transwell filters (8 μm, top and bottom sides) were blocked in 1% BSA-DMEM/F12 for 30 minutes (600 μL in bottom well, 100 μL in top well) and rinsed once with PBS. Matrigel (BD Biosciences) was diluted in ice cold PBS to 1000 μg/mL. The Bottom well side of pre-chilled transwell insert filters was coated with 30 μL of 1000 μg/mL Matrigel and incubated at 37° C. for one hour. Cells were detached using trypsin and neutralized with soybean trypsin inhibitor. Cells were centrifuged for 5 minutes at 1000 RPM (4° C.) then washed one time in DMEM/F12. Cell count and viability were determined using trypan blue and a hemacytometer. For antisense and sense treatment, cells had been transfected with FuGene6 coupled to oligonucleotides (3:1.5 optimized ratio) for 2 days prior to plating in the well. For antibody experiments, cells were preincubated with 10 μg/mL affinity purified Mig-7 polyclonal antibody (2) for 15 minutes in a 37° C. incubator. Media containing chemoattractant hepatocyte growth factor (HGF) was added to bottom wells first. Media without HGF and containing 50,000 cells was added to top wells. Cells were allowed to invade for indicated times at 37° C. in 5% $CO_2$, 95% humidified air incubator. After invasion for 72 hours, filters were rinsed with PBS then fixed in Hema-3 fixative for at least 30 minutes. Non-invaded cells in the upper chamber were removed with a cotton swab. Media from bottom wells was also analyzed for cells that potentially invaded through the Matrigel. Filters were dried and stained with Hema3 stains (Fisher Scientific, Inc). Filters were mounted shiny side up using DPX. Invaded cells were counted using a gridded coverslip (Electron Microscopy Science) at 400× magnification with a count of 10 squares (0.6× 0.6 mm each) per filter per treatment. All treatments were performed in triplicate and experiments were repeated three times.

Immunoblot. Cell lysates and immunoblots were performed as previously described (1) with the following modifications. Cells were lysed in 2% SDS, 60 mM Tris, 10% glycerol, 2× protease inhibitor) and quantified using a RC/DC Protein Assay (Bio-Rad). Lysates were boiled for 5 min in the presence of 100 mM DTT and equal amounts of protein were loaded onto a 12% polyacrylamide gel and run at constant 200 V for 30-40 min. Gels were semi-dry transferred (Boekel).

Membranes were blocked in TBS-tween (0.05%) containing 5% dry milk for one hour at RT. Endogenous Mig-7 protein was detected using affinity purified Mig-7 antibody (1:2, 000). A HRP-labeled secondary anti-rabbit IgG antibody was used to detect the Mig-7 antibody at a dilution of 1:40,000. Anti-β-tubulin (clone AA2, Upstate, Inc.) was used at 1:5000 dilution. Chemiluminescence Plus Reagent (Amersham) allowed detection of HRP-labeled antibodies when exposed to film.

RNA isolation and RT-PCR. Isolation of total RNA from MCF-7 endometrial carcinoma cells, DNAsing and RT-PCR was performed as previously described (1).

Peptides. Irrelevant and Mig-7 peptides (see Table 1 for sequences) were synthesized by Biosource, Inc. Peptides were evaluated by mass spectrometry and solubilized in media. Previously characterized MUC1 peptide GNNAP-PAHGVNNAPDNRPAP (7) was synthesized by American Peptide Co., Inc.

TABLE 1

Peptides used to stimulate MC

| Mig-7 (Accession DQ080207) (SEQ ID NO:1) | Irrelevant |
|---|---|
| RVHMRACSAGSAYLKQMK (SEQ ID NO:2); | MAASRCSGLYIVRNDTSG (SEQ ID NO:5); |
| GSAYLKQMKFCRMAASLD (SEQ ID NO:3); | YIVRNDTSGLSGSQWVDS (SEQ ID NO:6); |
| FCRMAASLDKVKKTDRGERG (SEQ ID NO:4). | LSGSQWVDSPLKSPCQVW (SEQ ID NO:7). |

Stimulation of human monocyte cells and MCF-7 killing assay. Human peripheral blood monocyte cell (MC) isolation, culture, and stimulation, were performed as previously described (7). Briefly, MC were isolated from breast adenocarcinoma patients under IRB approval (Texas Tech University). MC were cultured at $2 \times 10^6$ cells/ml in AIMV® serum-free lymphocyte medium (Gibco) in a 37° C. humidified 5% $CO_2$, 95% air atmosphere. IL-2 (Cetus) was added twice per week at 100 IU/ml on days 4, and 7. MC were stimulated with 1 μg/ml MUC1 alone or Mig-7 and MUC1 peptides on days 4 and 7. Cell lysis was evaluated on day 8 of peptide stimulation using a tetrazolium salt XTT assay (Roche, Inc) as previously described (9). MCF7 cells ($5 \times 10^3$ per well) were plated into 96-well tissue culture plates. Effector peptide-stimulated MC were added to each well in three effector cell to target cell ratios (E:T): 10:1, 5:1, and 2.5:1. Six wells were plated with MCF7 cells or no cells (background). Treatments were in replicates of 6 and each experiment was performed at least twice.

Maximal XTT™ was determined as the mean of six wells containing target MCF7 cells (i.e. no MC) and background was determined as the mean of the six wells containing only medium. The specific formation of formazan attributable to the presence of effector MC cells was determined from the wells containing effector cells alone. The percent specific lysis (% SL) was calculated as follows as previously described (7):

$$\% \ SL = \frac{OD_{(target-medium)} - OD_{(experimental \ wells-well \ with \ corresponding \ number \ of \ effector)}}{OD_{(target-medium)}} \times 100$$

Day 0 represents MCs that were not stimulated with peptides.

ELISA Cytokine Assay. The ELISA cytokine assay was a solid phase sandwich Enzyme Linked-Immuno-Sorbent Assay (ELISA) (BD Pharmingen Inc), used for the quantitative determination of human cytokines tumor necrosis factor-alpha (TNF-α), interferon-gamma (IFN-γ), and interleukin-10 (IL-10). Amounts of each cytokine present in supernatants were determined by measuring absorbance with a spectrophotometer, according to manufacturer's instructions.

Statistical analysis. Determinations of the statistical significance of the in vitro cytotoxicity assays and cytokine assays were performed by the Mann-Whitney Rank Sum test. Data from invasion assays were statistically analyzed by one way ANOVA and considered significant at 0.05.

Results:

Decrease of Mig-7 protein resulted in decreased carcinoma cell invasion. Because Mig-7 antisense inhibits cell scattering of cells plated for at least four days in a scratch assay of cell migration (1), these same oligonucleotides (ODN) were used to test if they decreased Mig-7 protein expression and if they inhibit cell invasion. In vitro invasion assays predict the invasive capability of cells in vivo. In addition, stably transfected HT29 cells expressing Mig-7 invade in 3D Matrigel cultures (submitted). Mig-7 antisense but not sense decreased Mig-7 protein levels by 60% as determine by immunoblot (FIG. 1B).

Using a modified Boyden chamber assay of cell invasion as described in Methods and Materials, Mig-7 anti-sense or sense treated HEC1A endometrial carcinoma cells were placed in the upper chamber of transwell (n=3 each treatment) on which the bottom side had been coated with Matrigel. Chemoinvasion of HEC1A cells toward HGF in the bottom wells were significantly inhibited by 3.5-fold (p<0.001) as compared to HGF alone or HGF with sense ODN (FIG. 1B).

FIGS. 1A and 1B show, according to exemplary aspects of the present invention, that antisense to Mig-7 inhibits chemoinvasion. A) Immunoblot demonstrating that Mig-7 antisense ODN decreases Mig-7 protein levels in lysates from HEC1A cells treated as described in Materials and Methods as compared to lysates from HEC1A cells treated with Mig-7 sense ODN, B) Mig-7 antisense (as), significantly inhibits HEC1A carcinoma cell SF(HGF) chemoinvasion of Matrigel as compared to SF (HGF) treatment alone or SF (HGF) with sense (se) Mig-7 ODN. Images below each treatment group show a representative invasion of cells for that group. Experiments were performed in triplicate for each treatment and repeated three times.

Antibody to Mig-7 resulted in decreased invasion in vitro. Antibodies have previously been shown to inhibit invasion of carcinoma cells expressing another membrane protein, chemokine receptor CXCR4, expressed on cancer cells however this expression is also found on normal cells (10). Therefore, the Applicant used affinity purified antibody to a peptide representing the first nine amino acids of Mig-7 (SEQ ID NO:31) which is the encoding region beginning at the consensus Kozak ATG site and ending at the first stop codon which is read through during translation). This antibody detects endogenous Mig-7 at the same size as anti-FLAG antibody detects FLAG-tagged Mig-7 in stably transfected cells. Using this Mig-7 antibody to treat HEC1A cells before plating in the upper well of the modified Boyden chamber as described in Methods section, a significantly decreased number of invaded cells was observed. When compared to irrelevant antibody, chemoinvasion toward HGF in the lower well was significantly inhibited (−80.4, p value 0.0046) by Mig-7 antibody (FIG. 2). Irrelevant IgG antibody did not significantly inhibit chemoinvasion whereas HGF significantly enhanced chemoinvasion over no HGF (FIG. 2).

FIG. 2 shows, according to exemplary aspects of the present invention, that antibody specific to Mig-7 inhibits HEC1A endometrial carcinoma chemoinvasion. Mig-7 affinity purified antibody but not IgG isotype antibody significantly decreased chemoinvasion of HEC1A cells into Matrigel. Experiments were performed in triplicate for each treatment and repeated three times.

Figure 3A:
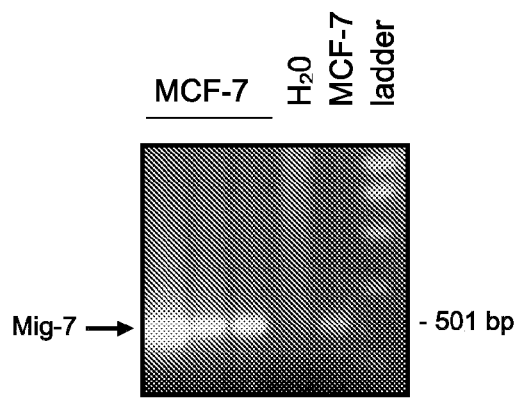
Figure 3B:
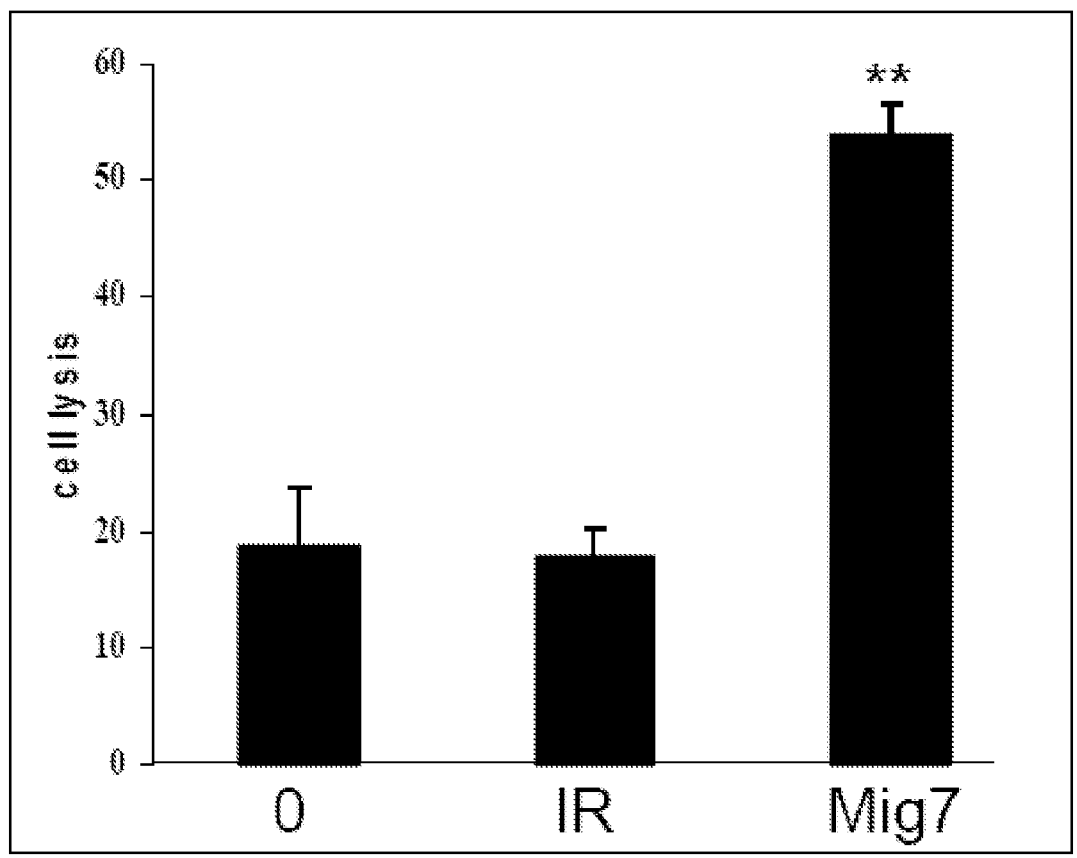
Figure 3C:
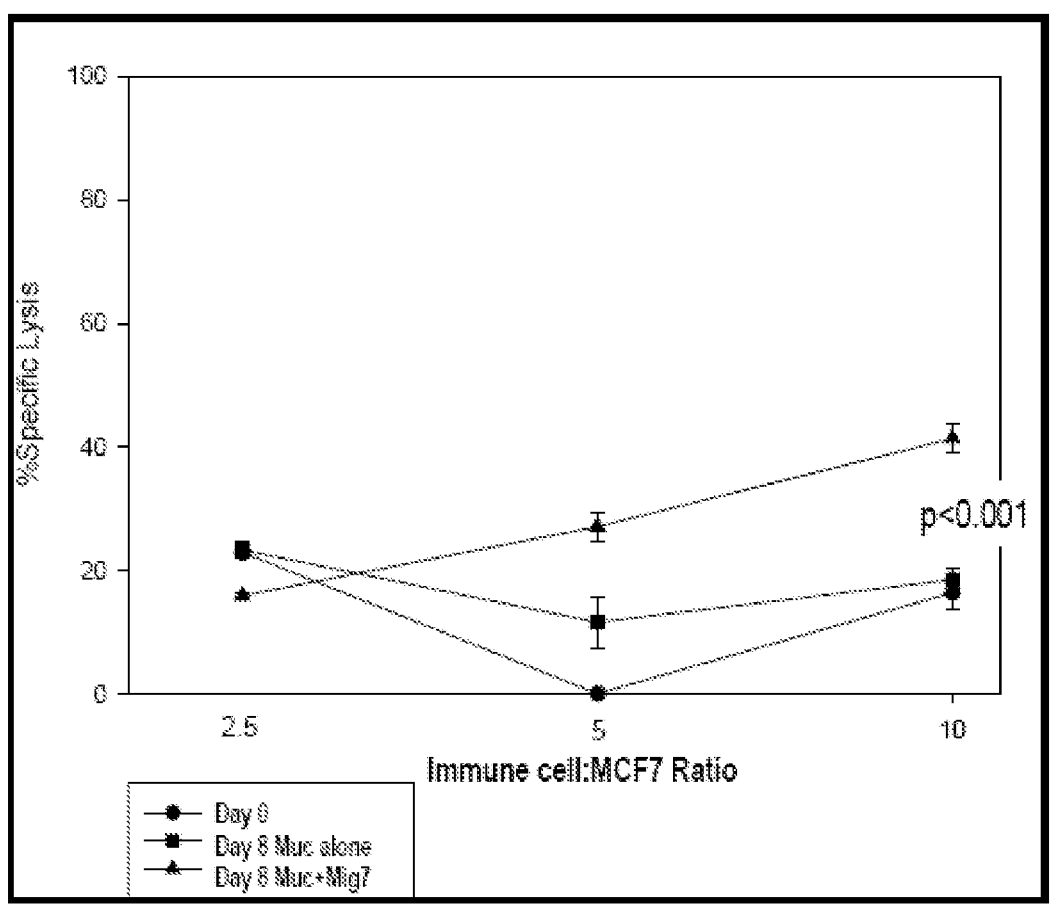

Stimulation of human peripheral blood monocytes (MC) with peptides specific to Mig-7 enhanced killing of MCF-7 breast carcinoma cells in vitro. Human MC were isolated under IRB approval as previously described (7). Mig-7 or irrelevant peptides (Table 1, herein above) were used first to determine which sequences contributed to enhanced MCF-7 killing in vitro. MCF-7 cells, as do most carcinoma cells, express Mig-7 (FIG. 3A). Peptides used are listed in Table 1. Stimulation with Mig-7 peptides significantly enhanced MC killing of MCF-7 cells by >2-fold over MUC1 peptide alone or irrelevant peptides. There was no significant difference between irrelevant peptides and MUC1 peptide alone (FIG. 3B At a ratio of 10 MC to 1 MCF-7 cell, unstimulated and MUC1 stimulated were indistinguishable in levels of MCF-7 killing. In contrast, Mig-7 peptides significantly increased MC killing of MCF-7 cells >2-fold over unstimulated and MUC1 stimulated as well as 1.9-fold over Muc1 with Mig-7 at the 5:1 ratio (FIG. 3C). Mig-7 peptide also significantly increased levels of MC produced tumor necrosis factor-α (TNF-α) over irrelevant peptide (FIG. 3D).

FIGS. 3A-D show, according to exemplary aspects of the present invention, that Mig-7 peptides enhance human monocyte killing of MCF-7 breast carcinoma cells. (A) Representative RT-PCR demonstrating expression of Mig-7 in MCF-7 cells. (B) Human MC cells stimulated with IL-2 and either no peptide (O), pooled irrelevant peptides (IR), or pooled Mig-7 peptides. (see Table 1). Note that Mig-7 peptides significantly (p value 0.001) enhanced MC killing of MCF7 carcinoma cells. Experiments have been repeated 3 times in replicates of 6 for each treatment group. MC were isolated from two different individuals. (C) Cytotoxic response of human isolated MC after peptide stimulation using indicated ratios of immune cells (MC) to MCF-7 cells. Bars are ±S.E. Experiments were repeated twice with replicates of six for each treatment group. (D) TNF-α production by human isolated MC after indicated peptide stimulation. TNF-α production was measured by ELISA assay as described in Methods and Materials after MC were cultured for 8 days with MUC1 peptide plus irrelevant peptides Mig-7 peptides. Bars are ±S.E. Assays were performed in triplicate.

References Relating to this Example 1

(1) Crouch S, Spidel C S, Lindsey J S. HGF and ligation of αvβ5 integrin induce a novel, cancer cell-specific gene expression required for cell scattering. Experimental Cell Research 2004; 292(2):274-87.

(2) Phillips T M, Lindsey J S. Carcinoma Cell-specific Mig-7: A new potential marker for circulating and migrating cancer cells. Oncology Reports 2005; 13:37-44.

(3) Hendrix M J C, Seftor E A, Kirschmann D A, Quaranta V, Seftor R E B. Remodeling of the Microenvironment by Aggressive Melanoma Tumor Cells. Ann NY Acad Sci 2003 May 1; 995(1):151-61.

(4) Brooks P C, Klemke R L, Schon S, Lewis J M, Schwartz M A, Cheresh D A. Insulin-like growth factor receptor cooperates with integrin alpha v beta 5 to promote tumor cell dissemination in vivo. Journal of Clinical Investigation 1997; 99(6):1390-8.

(5) Klemke R L, Yebra M, Bayna E M, Cheresh D A. Receptor tyrosine kinase signaling required for integrin alpha v beta 5-directed cell motility but not adhesion on vitronectin. Journal of Cell Biology 1994; 127(3):859-66.
(6) Folberg R, Hendrix M J C, Maniotis A J. Vasculogenic mimicry and tumor angiogenesis. Am J Pathol 2000; 156(2):361-81.
(7) Wright S E, Kilinski L, Talib S, Lowe K E, Burnside J S, Wu J Y, et al. Cytotoxic T Lymphocytes from humans with adenocarcinomas stimulated by native MUC1 Mucin and a Mucin peptide mutated at a glycosylation site. Journal of Immunotherapy 2000; 23(1):2-10.
(8) Hendrix M J C, Seftor E A, Seftor R E B. Comparison of tumor cell invasion assays: human amnion versus reconstituted basement membrane barriers. Invasion & Metastasis 1989; 9:278-97.
(9) Roehm N W, Rodgers G H, Hatfield S M, Glasebrook A L. An improved colorimetric assay for cell proliferation and viability utilizing the tetrazolium salt XTT. Journal of Immunological Methods 1991; 142(2):257-65.
(10) Müller A, Homey B, Soto H, Ge N, Catron D, Buchanan M E, et al. Involvement of chemokine receptors in breast cancer metastasis. Nature 2001; 410:50-6.
(11) Ahmad K A, Wang G, Slaton J, Unger G, Ahmed K. Targeting CK2 for cancer therapy. Anti-cancer Drugs 2006; 16(10):1037-43.
(12) Curcio L D, Bouffard D Y, Scanlon K J. Oligonucleotides as modulators of cancer gene expression. Pharmacology Therapeutics 1997; 74:317-32.
(13) Elez R, Piiper A, Kronenberger B, Kock M, Brendel M, Hermann E, et al. Tumor regression by combination antisense therapy against Plk1 and Bcl-2. Oncogene 2003; 22(1):69-80.
(14) Wang H, Hang J, Shi Z, Li M, Yu D, Kandimalla E R, et al. Antisense oligonucleotide targeted to Rlalpha subunit of cAMP-dependent protein kinase (GEM231) enhances therapeutic effectiveness of cancer chemotherapeutic agent irinotecan in nude mice bearing human cancer xenografts: in vivo synergistic activity, pharmacokinetics and host toxicity. International Journal of Oncology 2002; 21(1):73-80.
(15) Zelweger T, Miyake H, Cooper S, Chi K, Conklin B S, Monia B P, et al. Antitumor activity of antisense clusterin oligonucleotides is improved in vitro and in vivo by incorporation of 2'-O-(2-methoxy)ethyl chemistry. Journal of Pharmacology & Experimental Therapeutics 2001; 298(3):934-40.
(16) Tuma R S. Trastuzumab Faces Trials, Clinical and Otherwise. J Natl Cancer Inst 2006 Mar. 1; 98(5):296-8.
(17) Bonta I L, Ben Efraim S. Interactions between inflammatory mediators in expression of antitumor cytostatic activity of macrophages. Immunology Letters 1990; 25(4):295-301.
(18) Hildesheim A, de Gonzalez A B. Etiology and Prevention of Cervical Adenocarcinomas. J Natl Cancer Inst 2006 Mar. 1; 98(5):292-3.

Example 2

Translation of the Human Carcinoma- and Trophoblast-specific Mig-7 Requires Fidelity of the Purine-pyrimidine Repeat Region and Genetic Recoding Example overview. As stated above, Migration inducting gene-7 (Mig-7) is a new, human oncogene that is expressed strictly by solid tumor cells and by invasive fetal trophoblast cells but not by normal tissues. In 3D cultures, expression of Mig-7 in a noninvading carcinoma cell line is sufficient to cause sensing of the microenvironment, invasion and formation of vessel-like structures with a lumen. This expression also causes transfected cells to be significantly less adherent to tissue culture plastic and to laminins (submitted). Furthermore, antisense or antibody to Mig-7 inhibits migration and invasion in vitro. Receptor tyrosine kinases in concert with ligation of αvβ5 integrin induce Mig-7 mRNA but cloning and consistent endogenous protein expression as well as detection of Mig-7 protein requires tumor microenvironment factors.

Cloning of genes is now usually routine in molecular biology. Genetic sequences that allow cloning, expression and detection by standard molecular techniques are most commonly studied, leaving the function of the most difficult to clone and detect of these genetic codes a mystery.

For example, in this Example 2, Applicant demonstrates, surprisingly, that a cancer-specific, "noncoding" mRNA produces protein when using Applicant's combination of techniques. Migration inducting gene-7 (Mig-7) is unique in its induction, translation and detection making it highly cancer cell-specific. Research into this important oncogene has been hampered by the non-classical molecular and cell culture techniques required for cloning, maintenance of sequence fidelity, and translation. For example, genetically engineered E. coli are required to maintain the number of Mig-7 purine-pyrimidine repeats and reading frame when producing plasmids for expression. A Mig-7 sequence that produces protein in vivo contains stop codons. Nonetheless, the Applicant has confirmed herein that the Mig-7 sequence produces protein in vivo from the conserved Kozak consensus site ATG and not from other upstream start codons. Furthermore, mRNA tertiary structures reside in appropriate locations with respect to the first stop codon that likely allow recoding and frameshifting to produce Mig-7 protein in vivo.

In this Example 2, the Applicant details novel requirements for Mig-7 cloning and expression as well as relationship of these techniques to tumor progression. These techniques help elucidate the unique, tumor- and fetal trophoblast-specific expression for use as a novel biomarker (e.g., diagnostic, and/or prognostic marker) and as a therapeutic target for cancer therapies.

Methods for Cloning and Expressing an Atypical Gene with gt Repeats and Stop Codons, and Results:

I. Fidelity of Mig-7 Purine-Pyrimidine Repeat Region Requires Genetically Engineered E. coli that Lack Rearrangement Capability:

During initial isolation of Mig-7 cDNA the Applicant determined a guanine-thymine (gt) repeat region that encodes cysteine-valine dipeptide repeats (Crouch et al. 2004) that varied in number of gt repeats when grown in TOP10F' E. coli. It is known that Purine-pyrimidine repeats, resulting in a left handed zig-zag configured DNA (z-DNA), can be rearranged in sequences due to recombination events in E. coli (Santella et al. 1981; Fuchs et al. 1988). Therefore, to preclude unwanted rearrangements in E. coli, a genetically engineered strain from Stratagene, or TOP10F' E. coli was used for transformation with 3×FLAGCMV vector containing the Mig-7 cDNA as described (FIG. 1 legend).

FIGS. 5A and 5B show that genetically engineered E. coli (SURE™, Stratagene) are required (suitable) to maintain the integrity of the Mig-7 purine-pyrimidine repeat coding region. The Mig-7 sequence was amplified using primers corresponding to 805 to 1529 (SEQ ID NOS:29, 30, respectively) (Table 2) of the Mig-7 sequence (Accession number DQ080207) (SEQ ID NO:1). After amplification and checking size on a gel, fragments were cut with the indicated restriction enzymes, gel purified and ligated into p3×FLAG-CMV vector (SIGMA) that was also digested with HindIII and BamHI enzymes for directional insertion. TOP10F' *E. coli* or SURE cells were transformed using the chemical heat shock method and allowed to incubate in SOC media for one hour prior to plating on LB ampicillin (100 μg/ml) plates. At least 16 clones were isolated for each *E. coli* strain grown in LB broth with 2% glucose and plasmids purified using Qiagen Endo-free kit according to manufacturer's instructions. After purification, plasmids were sequenced at the Texas Tech sequencing facility and compiled using Vector NTI software program. FIG. 5A shows representative sequences of Mig-7 region containing gt repeats (underlined) ranging from 23 (SEQ ID NO: 22) to 29 (SEQ ID NO: 22) repeats in length (additional sequences are shown in FIG. 4). FIG. 5B shows Representative sequences of Mig-7 plasmids grown in SURE cells. Note the consistent number (18) of gt repeats.

Figure 6A:
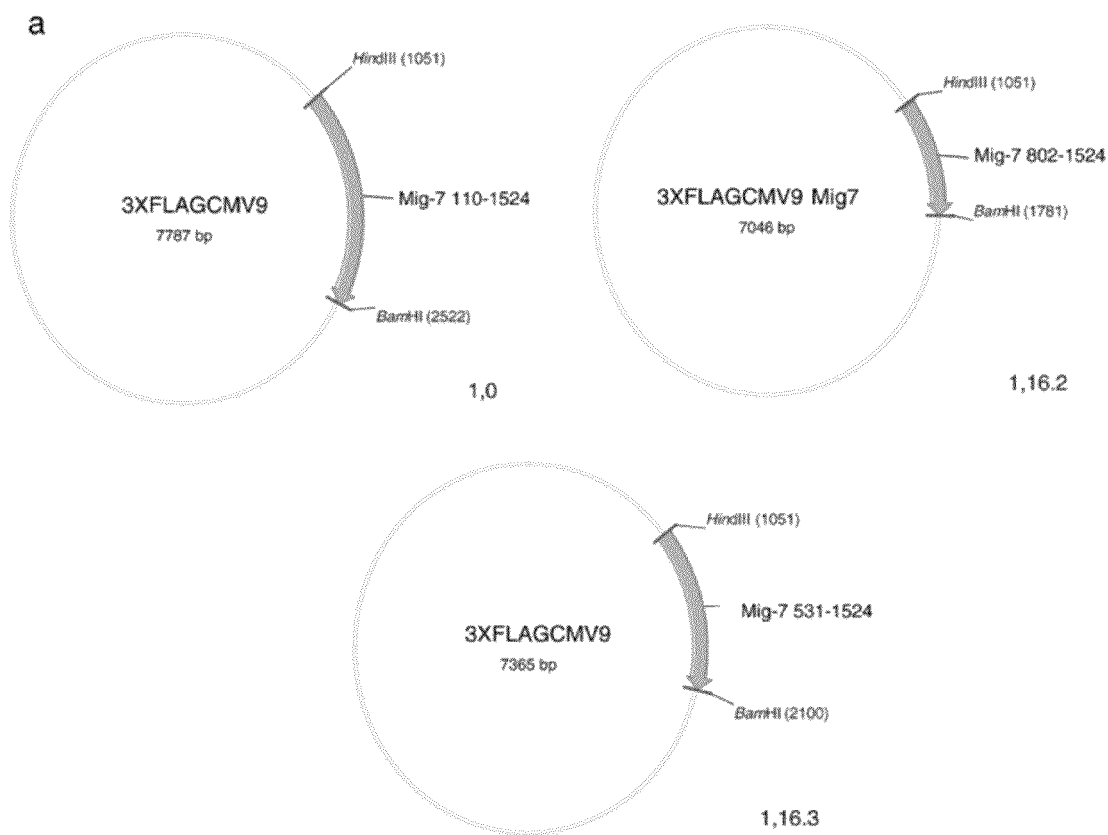
FIG. 6 shows, according to exemplary aspects of the present invention, shows that Mig-7 cloning into 3×FLAG-CMV produces protein from the Kozak consensus site ATG and not from other upstream ATG sites.
Figure 6B:
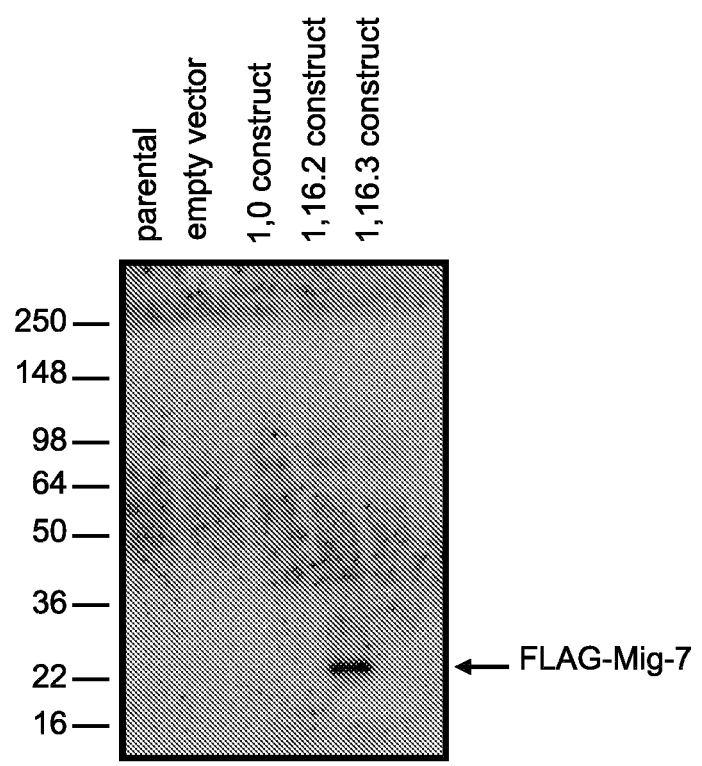

FIGS. 6A and 6B show that Mig-7 cloning into 3×FLAG-CMV produces protein from the Kozak consensus site ATG and not from other upstream ATG sites. FIG. 6A shows that all three constructs were cloned as described in FIG. 5 legend except using primer pairs in Table 2. Vectors were drawn in Vector NTI. Empty vector or Mig-7 containing vectors were transfected (3:1 optimized ratio FuGene6, Roche) into HT29 colon carcinoma cells (ATCC) cultured in McCoy's 5a medium with 10% FCS at 37° C. and 5% $CO_2$. Thirty-six hours after transfection, cells were selected in culture medium containing 800 μg/ml G418. After 21 days of selection, individual G418-resistant colonies were pooled for each well (n=3). FIG. 5B shows a representative immunoblot of protein lysates from HT29 cells that do not endogenously express Mig-7 due to a lack of αvβ5 integrin (Crouch et al. 2004) and that were individually stably transfected with the vector constructs described in FIG. 6A. Briefly, protein lysates (2% SDS, 60 mM Tris, 10% glycerol) were quantified

TABLE 2

Mig-7 specific targets used for cloning

| Region of DQ080207 | Construct ID | Primer pair |
|---|---|---|
| 110-1529 | 1, 0 | (F) 5' <u>GCGCAAGCTT</u>TATATGATGCCCCACC CAG3'<br>(R) 5' <u>GCGCGGATCC</u>GCCCGTGATGAATCATGTGA C 3') (SEQ ID NOS:25, 26, respectively) |
| 531-1529 | | (F) 5' <u>GCGCAAGCTT</u>CCCATGTCACAGTCCAGGCA3'<br>(R) 5' <u>GCGCGGATCC</u>GCCCGTGATGAATCATGTGA C 3') (SEQ ID NOS:27, 28, respectively) |
| 805-1529 | 1, 16.3 | (F) 5' <u>GCGCAAGCTT</u>CAGCCAACCATGGCAGC A 3')<br>(R) 5' <u>GCGCGGATCC</u>GCCCGTGATGAATCATGTGA C 3') (SEQ ID NOS:29, 30, respectively) |

F = forward, R = reverse

It was also found, at least in the context of 3×FLAGMig-7 or empty vector, the growth of cells required additional glucose (2%, Luria broth). FIG. 5 contains examples of Mig-7 sequences transformed in and grown in these two different *E. coli* strains and the altered length of Mig-7 gt repeats underlined (additional sequences are shown in FIG. 4). Guanine-thymine repeats varied from 23 to 29 in length in TOP10F' Mig-7 clones (FIG. 5A) in contrast to a consistent length of 18 repeats in Mig-7 sequences from SURE cell clones (FIG. 5B). In addition, translation from vectors with extended gt repeat regions did not express Mig-7 protein in vivo (data not shown) demonstrating the importance of maintaining this region for Mig-7 expression.

Whether cloning for genomic sequencing or for functional expression of cloned cDNA, using *E. coli* without rearrangement capabilities may lead to protein expression from sequences bearing purine-pyrimidine repeats. For example, the EST (N41315) that this region of Mig-7 is homologous to (Crouch et al. 2004) contains 19 instead of 18 repeats (Genbank) and thus would not produce protein. Furthermore, BLAST searches (Altschul et al. 1997) revealed over 850 hits on sequences containing gt repeats. Mig-7 cloning is just one example of a sequence with a region that can be rearranged and use of this genetically engineered *E. coli* should be used more often if functional studies of genes containing such repeats as well as other sequences that can be rearranged or deleted are to be reliable and consistent.

II. 3×FLAGMig7 produces protein in vivo from Kozak ATG:

Because of the unusual encoding and 5' regions of Mig-7 (accession DQ080207) (SEQ ID NO:1), several ATG sites were cloned as detailed herein for functional expression studies (FIG. 6).

using RC/DC Protein Assay (Bio-Rad). After heating samples for 5 min at 90° C. in the presence of 100 mM DTT, equal amounts of protein were loaded onto a 4-20% and electrophoresed at constant 200 V for 30-40 min. Gels were equilibrated in transfer buffer and semi-dry transferred (Boekel) for 1.5 h at 25 mAmp. Membranes were blocked in TBS-tween (0.05%) containing 5% dry milk for one hour at room temperature. FLAG-tagged (amino terminus) Mig-7 protein was detected using M2-peroxidase anti-FLAG antibody (1:100, Sigma). Chemiluminescence Plus Reagent (Amersham) allowed detection of HRP-labeled antibody. Representative immunoblot of lysates from stably transfected HT29 cells showing that 16.2 construct produced FLAG-Mig-7 protein of the predicted size (23 kD) and this band was absent in 1.0 and 1,16.3 construct protein lysates. Transfections, in triplicate for each construct, and immunoblots were performed at least twice with all three constructs and empty vector.

Thus, after successful growth, we harvested plasmids by Qiagen endo-free midi preparations and performed stable transfections using G418 at 800 μg/ml for selection that was previously determined by cell death curve analysis of HT29 colon carcinoma cells. This cell line was chosen because it does not endogenously express Mig-7 due to a lack of αvβ5 integrin expression (Crouch et al. 2004). HT29 cells transformed with the Mig-7 sequence from the Kozak consensus ATG (1,16.2) produced FLAG-Mig-7 protein in HT29 cells (FIG. 2*b*) whereas construct 1,16.3 and 1.0 did not express protein.

HT29 cells stably transfected with FLAG-Mig-7 (1,16.2, construct) are significantly less adherent to tissue culture plastic and to laminins (see Example 1 and 3 herein). Furthermore, in 2D cultures, there is no difference in morphology compared to empty vector transfected cells in stark contrast to 3D cultures where these cells form vessel-like structures with lumens similar to vasculogenic mimicry by tumor cells with aggressive behavior. Vasculogic mimicry by tumor cells is proposed to circumvent angiogenesis and may be why anti-antiangiogenic therapies show limited efficacy (Hess et al. 2005; Seftor et al. 2001; van der Schaft et al. 2005). Thus, polyadenylated mRNA with unusual reading frames that contain stop codons (see below) should be considered potentially functional to produce protein rather than relying on current algorithms to predict translation.

Figure 7A:
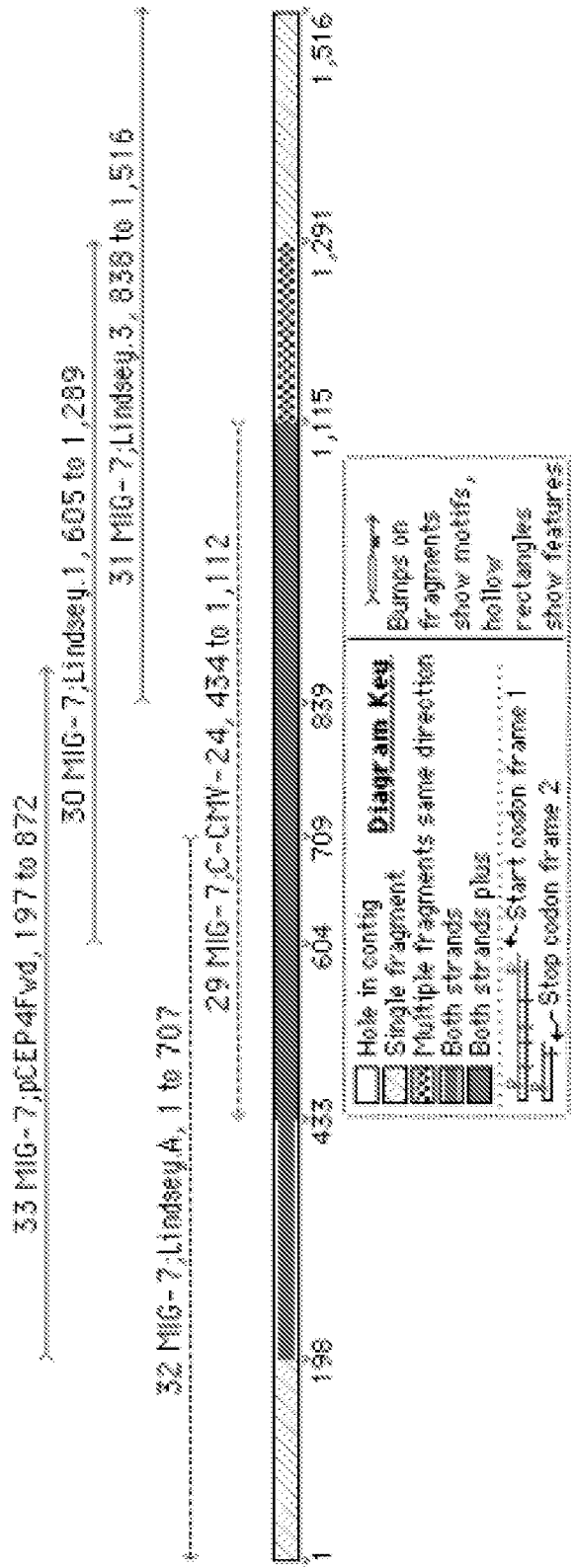

III. Mig-7 Protein Encoding Sequence Contains Stop Codons:

The first rounds of Mig-7 sequencing contained multiple stop codons and this finding was initially considered to be a sequencing mistake, particularly because this cloned region produced protein in HT29 cells (FIG. 6B, (Crouch et al. 2004) and submitted). However, after sequencing by two, independent facilities, with at least two different primer sets each (FIG. 7A shows a representative sequencing scheme), at least twice at each facility and compiling in Vector NTI, both consensus sequences were 100% homologous and contained stop codons (FIG. 7B). Amazingly, there are 15 stop codons in the "0" reading frame of the region that expresses ~22 kD protein in HT29 colon carcinoma cells (FIG. 7B). However, with frameshifting +1 and recoding (see below), stop codons would be eliminated and the size of Mig-7 protein observed by immunoblot analyses would be synthesized.

Specifically, FIGS. 7A and 7B show that the Mig-7 sequence that produced protein in vivo contains multiple stop codons in reading frame "0". Plasmids were produced and grown as previously described in FIG. 5, then sent to two different sequencing facilities, Texas Tech University Sequencing Core and Sequetech, Inc. Both facilities sequenced at least twice using two different overlapping primer sets in both directions each. (a) Representative sequencing scheme of overlapping and complementary strand sequencing. FIG. 7B shows that the consensus sequences from each facility are 100% homologous. Stop codons are indicated with asterisks in the predicted amino acid sequence from reading frame "0". Green highlights are UGA that can also encode for selenocysteine. Red highlights are UAG or UAA stop codons.

IV. Mig-7 mRNA contains predicted slippery and pseudoknot motifs that are known in other sequences to allow frameshifting and read through of stop codons:

In order to find an explanation for expression of protein from Mig-7 stop codon containing cDNA, the Applicant examined the sequence for possible 'recoding' structures. Pseudoknots are one type of tertiary mRNA structure 3' of stop codons with complementary binding of sequences outside a stem loop that bind to the loop (Giedroc et al. 2000). This type of structure can stimulate the ribosome to shift −1 or +1 in reading frame at slippery or "shifty" sites, although the exact molecular mechanisms are unclear. While this is a common mechanism of translation through a stop codon in viral transcripts, mammalian genes, Edr and Antizyme (AZ), are known to contain pseudoknots that stimulate frameshifting through a stop codon (Manktelow et al. 2005; Howard et al. 2001). Using the FSFinder software program (Moon et al. 2004), a predicted pseudoknot structure was determined in the Mig-7 sequence at a distance and structure consistent with known frameshifting (FIG. 8A SEQ ID NO:43). In addition, a predicted slippery site is located 5' of the first stop codon which would be after translation of the first nine amino acids (FIG. 8A. This pseudoknot is located 11 basepairs 3' of the first stop codon and is of the H-type (FIG. 8B SEQ ID NO:44) as determined by analysis of the highlighted sequence in the PsuedoViewer2 program (Han and Byun 2003). The predicted shift site and stop codon are underlined (FIG. 8B SEQ ID NO:44) indicating that the stop codon is in the context of a "shifty" site containing three uridine nucleotides typical of +1 frameshifting at the underlined heptanucleotide (Shah et al. 2002). Intriguingly, there is another stop codon immediately after the first stop in the +1 frame that we predict is read through.

Figure 8E:
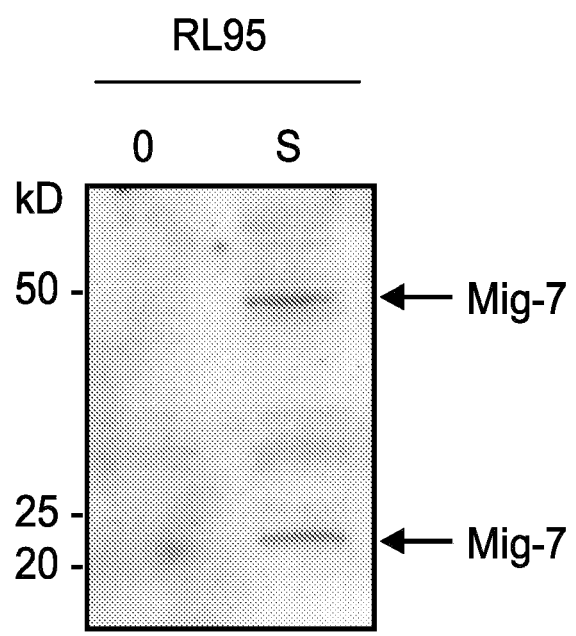

Specifically, FIGS. 8A-8E show that the Mig-7 sequence (SEC ID NOs:43, 44, 45, 46) contains a predicted shift-site and pseudoknot indicating potential frame-shifting, and that Mig-7 protein levels are increased with polyamine treatment consistent with recoding during translation. FIG. 8A shows a Mig-7 sequence (SEQ ID NO:43) from start codon (blue highlight, box) showing a highlighted putative shift site and pseudoknot in context (orange highlight, box). FIG. 8B (SEQ ID NO:44) shows a putative, Mig-7 mRNA pseudoknot structure with shift-site underlined and stimulatory uridine for readthrough after the stop codon with an asterisk highlighted in FIG. 8A (SEQ ID NO:43). FIG. 8C shows a sequence (SEQ ID NO:46) of Mig-7 protein after +1 frame-shift at the predicted shift site. This image also shows that only four additional stop codons are in this reading frame before the most likely terminal stop (the double-stop located between nucleotide positions 632 and 640 of SEQ ID NO:35). The Isoelectric point of the 203-207 amino acid frame-shift polypeptide is 8.23 and this sequence has 5 predicted PKC phosphorylation sites, 6 CK2 phosphorylation sites, and 2 myristoylation sites as determined by Prosearch.

Because Mig-7 is highly cysteine rich encoded by the gt repeat region (FIG. 5B (SEQ ID NOs: 35, 36, 37, 43, 45), it would not be surprising if the UGA codon is recoded as a selenocysteine. Furthermore, in viral stop codon readthrough, the subsequent hexanucleotides have been suggested to play a role, however, this sequence varies (Harrell et al. 2002). Recoding or readthrough of these subsequent stop codons is a possibility, and such products are encompassed herein. Nevertheless, we consistently observe .about.22 and .about.50 kD sized bands on immunoblots using antibody to the first nine amino acids (SEQ ID NO:31) which encodes for a peptide specific to Mig-7 (Crouch et al. 2004) and submitted) or using FLAG antibody to detect transfected FLAG-tagged Mig-7 (submitted). Observing a larger than predicted size for a given protein on immunoblots has precedence in another cysteine-rich protein, Ribonuclease U2 (Lucia-Ortega et al. 2005) and for laminin receptor which is predicted by mRNA to encode a 37 kD protein but is consistently detected at 67 kD. Laminin receptor plays an important role in tumor cell invasion (Givant-Horwitz et al. 2005). Intriguingly, Mig-7 expression causes significantly lower adhesion to laminins (submitted). While these data seem contradictive, there are laminin .gamma.-chain fragments produced by aggressive tumor cells that promote their invasion and vasculogenic mimicry (Seftor et al. 2001) processes in which Mig-7 plays a role (submitted). It is likely that Mig-7 forms multiple cysteine bonds with either itself or other proteins resulting in the .about.50 kD sized band on immunoblots.

It has been over a decade since it was proposed that all organisms have particular mRNAs that can be recoded (Gesteland et al. 1992). Mig-7 cDNA sequence structure is consistent with this recoding, and such recoded variants are encompassed herein. In addition, reinitiation of translation is more efficient when this takes place close to the initial start codon (Kozak 2001) consistent with the localization of the shift site and pseudoknot in Mig-7 sequence beginning only seven codons downstream of the ATG translation start site (FIG. 8A SEQ ID NO:43), and such reinitiation variants (e.g. SEQ ID NOS:46, 47) are encompassed herein.

Intriguingly, Mig-7 genomic sequence, on human chromosome 1 (Crouch et al. 2004), contains no introns, which is reminiscent of viral protein encoding DNA. In addition, most recoding due to frameshifting is through a single stop codon whereas, Mig-7 has four additional stop codons in the +1 frameshifted sequence including three UGA that can also encode for selenocysteine (Atkins and Gesteland 2002). Yet, Mig-7 produces protein in vivo ((Crouch et al. 2004; Phillips and Lindsey 2005), FIG. 6B, and submitted). The Applicant speculates that the predicted Mig-7 pseudoknot stimulates a +1 frameshift due to experiments that showed overlapping peptides specific to this frame stimulate human peripheral blood monocyte killing of MCF-7 breast carcinoma cells in vitro in a statistically significant manner (submitted; also see Example 1 herein). Mig-7 slippery sites 5' of the stop codon may involve the multiple uridine nucleotides, similar to those that have been shown in yeast, +1 frameshifted, actin filament binding ABP140 and telomerase subunit EST3 sequences (Shah et al. 2002). As with another +1 frameshifed protein, AZ, where the mammalian 5' slippery site is modular (Ivanov et al. 2000), the Mig-75' element will need to be determined empirically.

FIGS. 9A, 9B and 9C show, in view of the proposed shift −1 or +1 in reading frame at slippery or "shifty" sites (e.g., a shift of −1 or +1 in the reading frame after the ninth amino acid of Mig-7, SEQ ID NO:31), three potential reading frames (−1, 0, +1) for the corresponding Mig-7 encoding sequences (SEQ ID NO:35, 36 and 37). FIG. 9A shows the O-frame, FIG. 9B shows the +1-shifted frame, and FIG. 9C shows the −1-shifted frame. According to aspects of the present invention, after the first nine Mig-7 amino acids are encoded in the 0 frame, subsequent coding may be in the +1 shifted frame, the −1 shifted frame, or in the 0 frame (e.g., in the case of reinitiation of translation), depending on the event at the first stop codon of the 0 frame. Moreover, regardless of the frame used after the ninth amino acid, corresponding stop codons are subsequently encountered in all three reading frames, and according to additional aspects of the present invention, encoding through these subsequent stop codons may involve recoding (e.g., for the +1 frame, three out of four of the subsequent stop codons are TGA stop codons that may encode for selenocysteine), read-through, or potentially re-initiation at these subsequent stop codon position.

Therefore, according to particular aspects, protein/polypeptide embodiments of the invention not only encompass a polypeptide according to SEQ ID NO:32 and contiguous portions thereof, but additionally encompasses polypeptides comprising the first nine amino acids MAASRCSGL (SEQ ID NO:31), followed by one or more frameshifted amino acid sequence selected from SEQ ID NOS:39, 40, 41, 42.

In preferred aspects, after the ninth amino acid, the +1-reading frame (from MAASRCSGL, (SEQ ID NO:31, in the O-frame to SEMTLL . . . RSEMTLL or MTLL in the +1-frame) is used (SEQ ID NO:46), because this frameshift results in fewest downstream stops. This frame also contains peptides (SEQ ID NOs:2, 3, 4) that caused an increase breast carcinoma cell killing by peptide-stimulated monocytes from cancer patients in vitro, and overlapping peptides specific to this frame stimulate human peripheral blood monocyte killing of MCF-7 breast carcinoma cells in vitro in a statistically significant manner (see Example 1 herein). The TAG stop in line 542 can be read through or frame shifted through, with the double-stop located between nucleotide positions 632 and 640 of SEQ ID NO:35 being the likely 'true stop' given the detected 23 kD sized protein in immunoblots. However, because there are shift sites (slippery or "shifty" sites) at those stops as well, the protein may extend beyond the double-stop position shifting onto a different frame and end at a subsequent stop codon located between the double-stop and the polyA additional site beginning at nucleotide position 757 of SEQ ID NO:35. All such proteins are encompassed herein.

Therefore, particular aspects of the invention provide a Mig-7 polypeptide frame-shift or genetically recoded polypeptide encoded by SEQ ID NO:1 and comprising an amino-terminal MAASRCSGL (SEQ ID NO:31) sequence. In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS:32, 33, 34, 41, 42).

Preferably, the amino-terminal MAASRCSGL (SEQ ID NO:31) sequence is linked to at least one amino acid sequence selected from the group consisting of SEQ ID NOS: 39, 40, 41, 42 and contiguous portions thereof. In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS:32, 33, 34, 41, 42).

Preferably, the amino-terminal MAASRCSGL (SEQ ID NO:31) sequence is linked to at least one amino acid sequence selected from the group consisting of SEQ ID NOS:40, 41, and contiguous portions thereof as depicted in SEQ ID NOS: 46, 47. In particular aspects, the polypeptide is from about 203 to about 207 amino acid residues in length. In particular aspects, the polypeptide is from about 223 to about 240 amino acid residues in length (SEQ ID NOS:32, 33, 34, 41, 42).

Preferably, the amino-terminal MAASRCSGL (SEQ ID NO:31) sequence is linked to at least one amino acid sequence selected from the group consisting of SEQ ID NOS:40, 41 and contiguous portions thereof. In particular aspects, the polypeptide is from about 203 to about 207 amino acid residues in length (SEQ ID NOS:46, 47). In particular aspects, the polypeptide is from about 223 to about 240 amino acid residues in length (SEQ ID NOS:32, 33, 34, 41, 42).

V. The Polyamine, Spermine, Increased Translation of Mig-7

AZ frameshifting translation is enhanced by polyamines (Petros et al. 2005). In support of frameshifting and recoding events that lead to Mig-7 protein translation in vivo, the polyamine, spermine, enhanced synthesis of Mig-7 in HEC1A and in RL95 endometrial carcinoma cells (FIG. 8D). Interestingly, the lower band (~22 kD non FLAG tagged) for Mig-7 protein was more prevalent in lysates that were not reduced prior to PAGE. In addition, the larger band was not initially detected in untreated HT29 cells expressing 3×FLAG Mig-7 under the CMV promoter in the absence of Matrigel ((Crouch et al. 2004) and FIG. 6B). Whereas, a larger Mig-7 band (~50 kD) was detected in lysates from HT29 cells plated on the extracellular matrix Matrigel (submitted).

One explanation for this difference in Mig-7 protein size detected by immunoblot is that reduction and denaturing of highly cysteine-rich, >10% in the first 91 amino acids, Mig-7 was not complete causing the more compact non-reduced form to migrate further in the gel. This PAGE difference in size has also been determined for another cysteine-rich protein (Lucia-Ortega et al. 2005). Indeed, the Applicant has determined that the peptide to the cysteine-valine dipeptide repeat region would not solubilize in vitro using various conditions (data not shown). Another explanation may involve multiple cysteine bond formation with other cysteine-rich proteins as previously mentioned. As a result, reducing Mig-7 cysteine interactions and keeping them reduced may cause the different sizes detected by immunoblot.

Notably, spermine allows readthrough of UGA termination codons in another mammalian messenger RNA, rabbit beta-globin mRNA, when it is translated in a rabbit reticulocyte cell-free system. This readthrough is specific to UGA and not UAA (Hryniewicz and Vonder Haar 1983). Whereas, in *E. coli*, readthrough of the UAG stop codon, but not of UGA or UAA stop codons, is permitted with another polyamine, putrescine (Yoshida et al. 2002). Furthermore, tumor cells overexpress the rate limiting enzyme, onithine decarboxylase (ODC), in polyamine biosynthesis and ODC is considered an oncogene (Gerner and Meyskens 2004). However, so far the use of difluoromethylornithine which irreversibly inhibits ODC, has had modest success as an anticancer therapy due to effective dose toxicity (Meyskens, Jr. and Gerner 1999). Moreover, cancer specific targets in this pathway have not previously been identified. Mig-7 may be such as target.

Polyamines also play an indirect role in protein modification. Specifically, polyamines increase casein kinase 2 (CK2) levels and activity (Childs et al. 2003). Cancer cells overexpress CK2 due to their high levels of polyamines and has been suggested as a potential anti-cancer target (Ahmad et al. 2006). However, unlike Mig-7, it is ubiquitously expressed and not cancer cell specific. Interestingly, Mig-7 protein (SEQ ID NO:46), after the +1 frameshift, has six predicted CK2 phosphorylation sites (FIG. 8C). Thus, polyamines could be facilitating both translation of Mig-7, by enhancing frameshifting, and Mig-7 protein modification through phosphorylation by CK2.

FIG. 8D shows a immunoblots of lysates from HEC1A endometrial carcinoma cells cultured as previously described (Crouch et al. 2004) with the addition of 1.0 mM aminoguanidine and 0.1 mM spermine unless otherwise indicated. Aminoguanidine is required to prevent toxicity due to conversion of spermine to toxic byproducts by bovine calf serum oxidase (Sharmin et al. 2001). Immunoblots were performed as previously described except that affinity purified Mig-7 antibody (1:2,000) generated to the first 9 amino acids was used to detect endogenous Mig-7 produced by HEC1A and RL95 cells. Polyamine treatment induces ~22 and ~50 kD Mig-7 bands in HEC1A cells at 0.1 mM spermine. The results represent 2 independent experiments. FIG. 8E shows a representative immunoblot of lysates from RL95 cells treated with 1.0 mM aminoguanidine and 1.0 mM spermine (S) or no spermine (0). Both ~22 and ~50 kD Mig-7 bands were elevated in spermine treated cells. Equal amounts of protein (20 μg) were loaded in all experiments.

In summary, sequences that do not meet classical expression criteria are often not known or recognized in the art, as in the present case, and thus are additionally not included on commercially available microarrays. Therefore, cancer researchers have heretofore been missing important Mig-7 gene expression data and compositions that provide insights and cell-specific reagents, therapeutics and targets for cancer therapies, and markers of cancer, cancer progression/stage as well as recurrence. In this Example novel Mig-7 nucleic acid and polypeptides sequences are provided.

Mig-7 sequence is reminiscent of a viral sequence in that it does not contain introns, it possesses viral-like repeat sequences, and genetic recoding likely allows translation. Because tumor microenvironment growth factors and interactions regulate Mig-7 expression which is sufficient for tumor cell invasion and vessel-like structure formation in 3D cultures as well as its specificity to carcinoma cells and fetal trophoblasts ((Crouch et al. 2004; Phillips and Lindsey 2005), the described findings provide compositions and methods for broadly applicable diagnostic, prognostic and treatments of cancers.

References Relating to this Example 2

Ahmad K A, Wang G, Slaton J, Unger G and Ahmed K. (2006). *Anti-cancer Drugs*, 16, 1037-1043.

Altschul S F, Madden T L, Schäffer A A, Zhang J, Zhang Z, Miller W and Lipman D J. (1997). *Nucl Acids Res*, 25, 3389-3402.

Atkins J F and Gesteland R. (2002). *Science*, 296, 1409-1410.

Childs A C, Mehta D J and Gerner E W. (2003). *Cellular and Molecular Life Sciences*, 60, 1394-1406.

Clayerie J-M. (2005). *Science*, 309, 1529-1530.

Crouch S, Spidel C S and Lindsey J S. (2004). *Experimental Cell Research*, 292, 274-287.

Fuchs R P P, Freund A M and Bichara M. (1988). *Methods and Consequences of DNA damage processing*. Alan R. Liss, Inc.: New York.

Gerner E W and Meyskens F L. (2004). *Nat Rev Cancer*, 4, 781-792.

Gesteland R F, Weiss R B and Atkins J F. (1992). *Science*, 257, 1640-1641.

Giedroc D P, Theimer C A and Nixon P L. (2000). *Journal of Molecular Biology*, 298, 167-185.

Givant-Horwitz V, Davidson B and Reich R. (2005). *Cancer Letters*, 223, 1-10.

Han K and Byun Y. (2003). *Nucl Acids Res*, 31, 3432-3440.

Harrell L, Melcher U and Atkins J F. (2002). *Nucl Acids Res*, 30, 2011-2017.

Hess A R, Postovit L-M, Margaryan N V, Seftor E A, Schneider G B, Seftor R E B, Nickoloff B J and Hendrix M J C. (2005). *Cancer Res*, 65, 9851-9860.

Howard M T, Shirts B H, Zhou J, Carlson C L, Matsufuji S, Gesteland R F, Weeks R S and Atkins J F. (2001). *Genes to Cells*, 6, 931-941.

Hryniewicz M M and Vonder Haar R A. (1983). *Molecular and General Genetics*, 190, 336-343.

Ivanov I P, Gesteland R F and Atkins J F. (2000). *Nucl Acids Res*, 28, 3185-3196.

Kozak M. (2001). *Nucl Acids Res*, 29, 5226-5232.

Lucia-Ortega L, De los Rios V, Martinez-Ruiz A, Oñaderra M, Lacadena J and Gavilanes J G. (2005). *Electrophoresis*, 26, 3407-3413.

Manktelow E, Shigemoto K and Brierley I. (2005). *Nucl Acids Res*, 33, 1553-1563.

Meyskens F L, Jr. and Gerner E W. (1999). *Clin Cancer Res*, 5, 945-951.

Moon S, Byun Y, Kim H-J, Jeong S and Han K. (2004). *Nucl Acids Res*, 32, 4884-4892.

Petros L M, Howard M T, Gesteland R F and Atkins J F. (2005). *Biochemical and Biophysical Research Communications*, 338, 1478-1489.

Phillips T M and Lindsey J S. (2005). *Oncology Reports*, 13, 37-44.

Santella R M, Grunberger D, Weinstein I B and Rich A. (1981). *Proceedings of the National Academy of Sciences USA*, 78, 1451-1455.

Seftor R E B, Seftor E A, Koshikawa N, Meltzer P S, Gardner L M G, Bilban M, Stetler-Stevenson W G, Quanranta V and Hendrix M J C. (2001). *Cancer Res*, 61, 6322-6327.

Shah A A, Giddings M C, Parvaz J B, Gesteland R F, Atkins J F and Ivanov I P. (2002). *Bioinformatics*, 18, 1046-1053.

Sharmin S, Sakata K, Kashiwagi K, Ueda S, Iwasaki S, Shirahata A and Igarashi K. (2001). *Biochemical and Biophysical Research Communications*, 282, 228-235.

van der Schaft D W J, Hillen F, Pauwels P, Kirschmann D A, Castermans K, oude Egbrink M G A, Tran M G B, Sciot R, Hauben E, Hogendoorn P C W, Delattre O, Maxwell P H, Hendrix M J C and Griffioen A W. (2005). *Cancer Res*, 65, 11520-11528.

Yoshida M, Kashiwagi K, Kawai G, Ishihama A and Igarashi K. (2002). *J Biol Chem*, 277, 37139-37146.

Example 3

Expression of Mig-7 Allowed Cancer Cells to Sense a 3D Environment, to Invade and to Form Vessel Structures Example overview. Interactions between carcinoma cells and their environment are critical for disease progression. However, the molecular requirements are poorly understood. To address this problem, the Applicant utilized a novel human cancer-specific gene expression system, Mig-7 whose expression is restricted to cancer cells regardless of type.

Mig-7 is a cysteine-rich membrane protein whose mRNA and protein synthesis is not typical, as shown herein. Mig-7 expression is a result of receptor tyrosine kinase (RTK) c-Met activation as well as ligation of αvβ5 and Mig-7 antisense but not inverted antisense inhibits carcinoma cell scattering (1). Malignant tumors, blood from cancer patients and metastatic sites express Mig-7 regardless of tissue of origin. Notably, Mig-7 has not been detected in 25 different normal tissues (n=6 each tissue) or in blood from normal subjects (1;2).

Aggressive, invasive tumor cells can form vessel-like structures in 3D cultures. Laminin5-gamma2 promigratory fragments promote this vessel-like formation by aggressive melanoma cells in 3D cultures. In vivo, predominantly tumor rather than endothelial cells form vessels in the interior, more hypoxic region of tumors (3). Moreover, RTK-induced cancer cell migration, invasion and dissemination of aggressive carcinoma cells require αvβ5 signaling, the crosstalk that induces Mig-7 (1), in vivo and in vitro (4;5). Fetal cytotrophoblasts are similar to cancer cells because they invade the maternal tissues during placenta development under RTK and αvβ5 signaling, evade immune system detection, endovascularly invade and are the only other cell type known to undergo vasculogenic mimicry (6). Surprisingly, Mig-7 cDNA is homologous to ESTs isolated from early invasive stage placenta as well as all cancer types studied while, in contrast, is not found in noninvasive term placenta or in other normal tissues (1;2).

Because carcinoma and cytotrophoblast both engage in vasculogenic mimicry, in this Example the Applicant tested and confirmed the hypothesis that Mig-7 is also expressed by fetal/embryonic cytotrophoblasts and plays a role in their common cell behaviors of invasion as well as vessel formation/restructuring resulting in leakiness. Importantly, 3-D cultures revealed that Mig-7 expression causes invasion and vessel formation. Adhesion assays to various components of the extracellular matrix suggests that a mechanism for Mig-7 in vessel formation by tumor cells is due to less adhesion to laminin. This Example provides further support for the efficacy of targeting Mig-7 in cancer therapies.

In studies using a nude mouse model of metastasis, Mig-7 protein primarily localized to vessels in lymph nodes to which subcutaneously injected carcinoma cells had spread. Tumor microenvironment growth factors, HGF, IGF-1 and EGF, each individually induced Mig-7 in αvβ5 integrin-positive carcinoma cells. αvβ5 integrin is important for tumor cell dissemination in vivo. Cytotrophoblasts, which possess αvβ5, expressed Mig-7 at a time point prior to their invasion on Matrigel. In 3D cultures, expression of Mig-7 caused vessel structure formation. Lastly, Mig-7 expressing cells are >30% less adherent to a mix of laminins 1, 2, 3, 6, 8 & 10 in a statistically significant manner (p<0.001). Less adhesion to laminin is required for vasculogenic mimicry, a phenotype of aggressive cancer and fetal cytotrophoblast cells. The facts that Mig-7 is induced by growth factors that regulate PI3K, a signaling pathway required for vasculogenic mimicry, is localized to vessels in metastases, causes vessel-like formation and less adherence to laminin, collectively indicates that Mig-7 expression serves to allow cells to sense their environment, to invade and to cause vasculogenic mimicry. Therefore, according to particular aspects, Mig-7 provides a molecular target for therapies to modulate tumor progression.

Methods and Materials:

Xenograft mouse model. The nude mouse model was performed as described previously (2) under IACUC approval.

RNA isolation and Relative RT-PCR. RNA isolation and relative RT-PCR including optimization of cycle number to achieve mid-linear range were performed as described previously (1). PCR products were confirmed by Southern blot (Mig-7 specific cDNA probe) or by subcloning and sequencing.

Immunohistochemistry (IHC). Detection of Mig-7 protein was performed using Mig-7 specific affinity purified antibody produced in rabbits immunized with conjugated Mig-7 peptide (MAASRCSGL) (SEQ ID NO:31) representing the first nine amino acids of Mig-7 protein (1). Briefly, antigen retrieval by microwave (2 seconds) was performed with cryostat sections (20 μm) of fresh frozen lymph node (three slides each) from nine endometrial carcinoma-injected and five control (Matrigel alone injected) nude mice. Cryosections were fixed immediately with 100% methanol at −70° C. for 10 minutes. Slides were washed 3× in PBS then pre-blocked in PBS containing 1% BSA, 5% preimmune rabbit serum, and 5% anti-mouse Fab2 fragment (SIGMA). Slides were then incubated simultaneously with anti-β-actin (1:1000, SIGMA), that recognizes both human and mouse β-actin, and Mig-7 antisera (1:50) overnight at 4° C. Slides were washed 3× in PBS containing 1% BSA then incubated for 30 minutes with antimouse IgG and antirabbit IgG both at 1:1000. After washing in PBS/BSA, slides were coverslipped with Vectashield Hard-set (Vector Labs) and analyzed using an Olympus IX-70 laser confocal scanning microscope equipped with an Olympus 60×/1.4 N.A. objective lens.

Western blot analyses. Western blot analyses were performed as previously described with the following modifications. Cells grown in (3D) or on (2D) Matrigel cultures were homogenized in lysate buffer (2% SDS, 100 mM DTT, 0.01% bromophenol blue, 60 mM Tris, 10% glycerol, 2× protease inhibitor) and quantitated using RC/DC Protein Assay (Bio-Rad). Equal amounts of protein were loaded onto a 12% polyacrylamide gel and run at constant 200 V for 30-40 min. Gels were equilibrated in transfer buffer and semi-dry transferred (Boekel) for 1.5 h at 25 mAmp. Membranes were blocked in TBS-tween (0.05%) containing 5% dry milk for one hour at room temperature. Endogenous or FLAG-tagged Mig-7 protein was detected using affinity purified Mig-7 antibody (1:2,000) generated to the first 9 amino acids or the M2-peroxidase anti-FLAG antibody (1:100, Sigma), respectively. A HRP-labeled secondary anti-rabbit IgG antibody was used to detect the Mig-7 antibody at a dilution of 1:40,000. Chemiluminescence Plus Reagent (Amersham) allowed detection of HRP-labeled antibodies and exposed to film several times for different lengths of time.

Northern blot analyses. Were performed as previously described (1).

Quantitative Real time RT-PCR. Reverse transcription of total RNA was carried out using the TaqMan Gold RT-PCR kit as described by the manufacturer (Applied Biosystems). This was followed by quantitative real-time PCR, which was performed using the Applied Biosystems 9700HT sequence detection system. Each target was amplified in triplicate with a Mig-7 specific primer probe set or 18S Assay-on-Demand primer probe set (Applied Biosystems). In triplicate, 5 µL of cDNA target was added to a 20 µL mix consisting of 1×TaqMan universal PCR master containing Amperase UNG and 1 µL of primer/probe. Reactions were incubated at 50° C. for 2 minutes, then 95° C. for 10 minutes. This was followed by 40 cycles of 95° C. for 15 seconds and 60° C. for 1 minute. A five-fold titration of control template was included in every run to assess PCR efficiency, along with a minimum of three negative controls. Levels of template were then calculated using the comparative Ct method using 18S as the endogenous control and time 0 h as the calibrator (ABI User Bulletin #2). Data is presented as $2^{-\Delta\Delta Ct} \pm SD$.

Cell cultures and transfections. Human cytotrophoblasts were isolated from first or second trimester placentas under IRB approval and patient consent as previously described (7). Cytotrophoblasts were cultured on an extracellular matrix, Matrigel (BD Biosystems), at 37° C. in 5% $CO_2$, which at 12 hours initiates their differentiation along the invasive pathway (8). Cell cultures other than primary cytotrophoblasts were performed as previously described (1;2). HT29, HEC1A or RL95 cells were plated on Matrigel (1:6) dilution from confluent cultures for indicated times prior to collecting protein lysates. 3D cultures were performed using 50 µl domes of Matrigel (no dilution) allowed to polymerize for 1 hour at room temperature, then 30 minutes at 37° C. in a humidified, 5% carbon dioxide incubator. Cells were removed from their plates non-enzymatically (2 mM EGTA) and 2 µl injected as single cell suspensions ($7.5 \times 10^5$) into the dome of Matrigel.

Statistical Analyses. All experiments were performed two or three times as indicated in figure legends. The one-way analysis of variance (ANOVA), Tukey-Kramer Multiple comparisons test and Grubb's test for outliers were used for statistical analyses in the GraphPad Prism statistical analyses software. $P<0.05$ was considered significant.

Results:

Mig-7 protein localized to vessel structures of metastases in a nude mouse model. When testing the invasion capabilities of human endometrial carcinoma cell lines, RL952 (RL95) and HEC1A in a xenograft nude mouse model, n=4 each cell line. Mig-7 protein was localized in lymph nodes to which the cells had spread by fluorescent immunohistochemistry using a polyclonal antisera to the first 9 amino acids of Mig-7 protein and confocal analysis. Human specific Mig-7 predominantly localized to vessel structures as shown in FIG. 10 (arrows).

Figure 10:
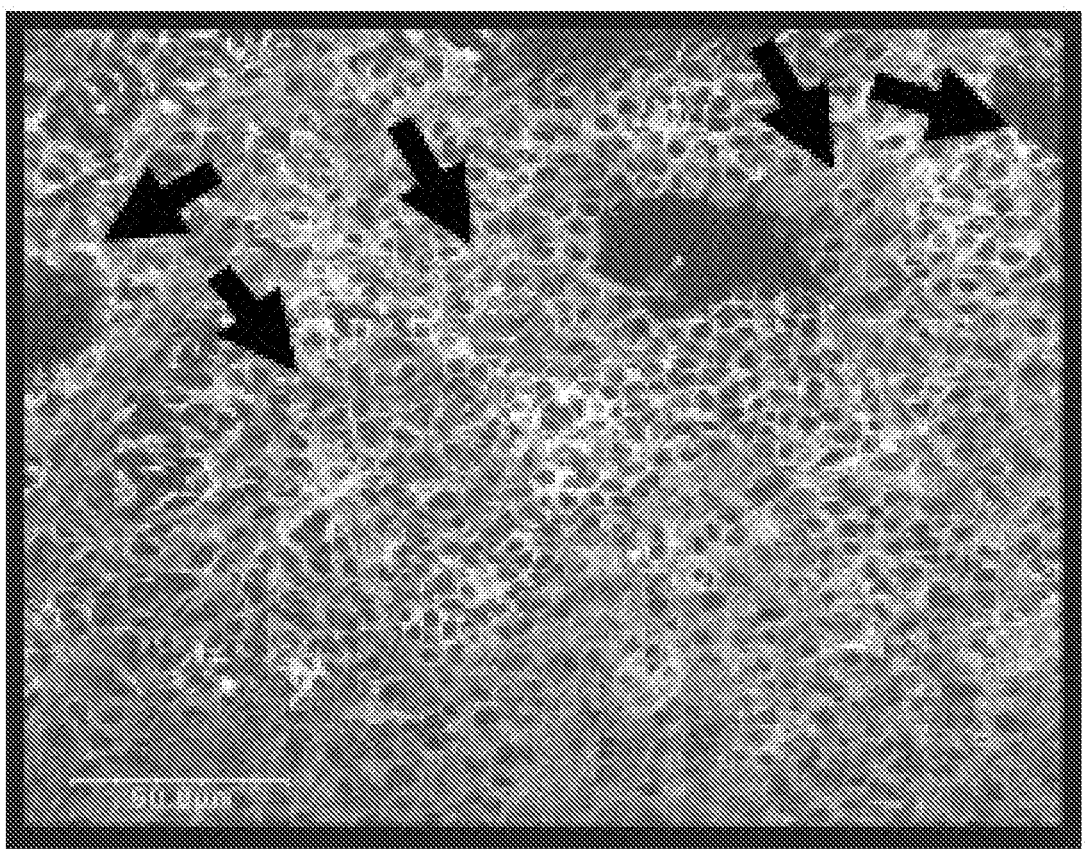
FIG. 10 shows, according to exemplary aspects of the present invention, that Mig-7 localizes primarily to vessels in xenograft nude mouse models of metastasis. Representative confocal analysis of Mig-7 protein immunohistochemical localization is shown. Rhodamine-conjugated anti-rabbit IgG (red) bound to Mig-7 antibody overlayed on the same area and sample scanned sequentially for Fluoroscein-conjugated anti-mouse IgG (green) binding to β-actin antibody. Arrows point to Mig-7 positive areas of vessels in lymph nodes to which subcutaneously injected HEC1A endometrial carcinoma cells in Matrigel had spread.

FIG. 10 shows that Mig-7 localizes primarily to vessels in xenograft nude mouse models of metastasis. Representative confocal analysis of Mig-7 protein immunohistochemical localization is shown. Rhodamine-conjugated anti-rabbit IgG (red) bound to Mig-7 antibody overlayed on the same area and sample scanned sequentially for Fluoroscein-conjugated anti-mouse IgG (green) binding to M-actin antibody. Arrows point to Mig-7 positive areas of vessels in lymph nodes to which subcutaneously injected HEC1A endometrial carcinoma cells in Matrigel had spread. Lymph nodes from animals injected with Matrigel alone (i.e. no cells) or incubated with antibody pretreated with Mig-7 peptide against which the antibody was generated were negative for Mig-7 (red) fluorescence. Detection of Mig-7 protein was performed using Mig-7 specific affinity purified antibody from antisera produced in rabbits immunized with conjugated Mig-7 peptide (MAASRCSGL SEQ ID NO:31) representing the first nine amino acids of Mig-7 protein{Crouch, Spidel, et al. 2004 249/id}. Methods for immunohistochemistry are previously described{Phillips & Lindsey 2005 276/id}. Experiments were repeated twice with 4-5 animals per treatment group.

Tumor microenvironment growth factors mediated expression of Mig-7 in $\alpha v \beta 5$ integrin positive cells. Mig-7 is detected in all types of cancers and it is known that other growth factors induce $\alpha v \beta 5$ activation. Tumor dissemination mediated by IGF1 in vivo (4) and in vitro, EGF-induced invasion of FG pancreatic carcinoma cells (5) requires this cross-talk signaling. Therefore, the Applicant tested whether other RTK ligands, IGF1 and EGF, can induce Mig-7 in $\alpha v \beta 5$ positive carcinoma cells. After obtaining FG cells (a gift from David Cheresh, Scripps Institute), the Applicant tested the expression of $\alpha v \beta 5$ in these cells in comparison with two other carcinoma cell types, HT29 colon carcinoma cells and the cells from which we originally isolated Mig-7, RL-95 endometrial carcinoma cells.

Figure 11A:
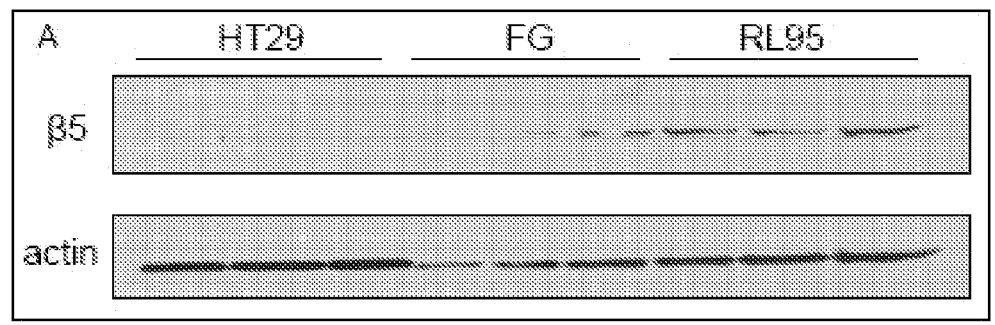
FIGS. 11A-11C show, according to exemplary aspects of the present invention, that RTK ligands, IGF-1 and EGF, known to be produced in the tumor microenvironment, induce Mig-7 in αvβ5 integrin-positive carcinoma cells but not in αvβ5 negative HT29 cells.

Using a $\beta 5$ antibody and Western blot analysis, HT29 cells lacked $\beta 5$ whereas FG cells and RL95 cells were positive for this integrin subunit (FIG. 11A).

Figure 11B:
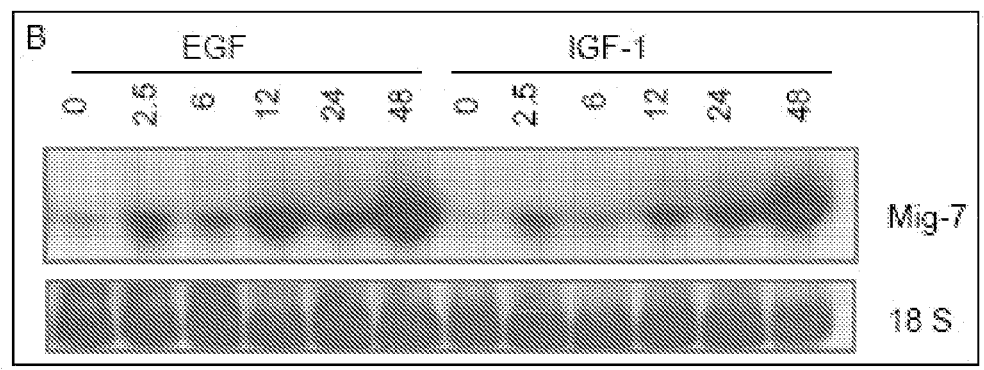

IGF-1 promotes tumor dissemination in vivo through cross-talk with $\alpha v \beta 5$ (4) In addition, the FG pancreatic carcinoma cell line requires signaling from $\alpha v \beta 5$ in conjunction with EGF receptor activation for migration on vitronectin (5). Another RTK ligand, HGF induces Mig-7 in RL95 cells in an $\alpha v \beta 5$-ligation dependent manner (1). The Applicannt used $\alpha v \beta 5$-positive FG cells to examine if EGF and IGF-1. A time course after a single application of EGF or IGF-1 showed that both RTK ligands induce Mig-7 mRNA in FG cells (FIG. 11B). In addition, the levels of Mig-7 increase overtime with a single application of either ligand at time point 0 (FIG. 11B). In contrast, with $\alpha v \beta 5$-negative HT29 cells (FIG. 11A), Mig-7 is not induced with either ligand even with 40 cycles of PCR after reverse transcription (FIG. 11C).

Figure 11C:
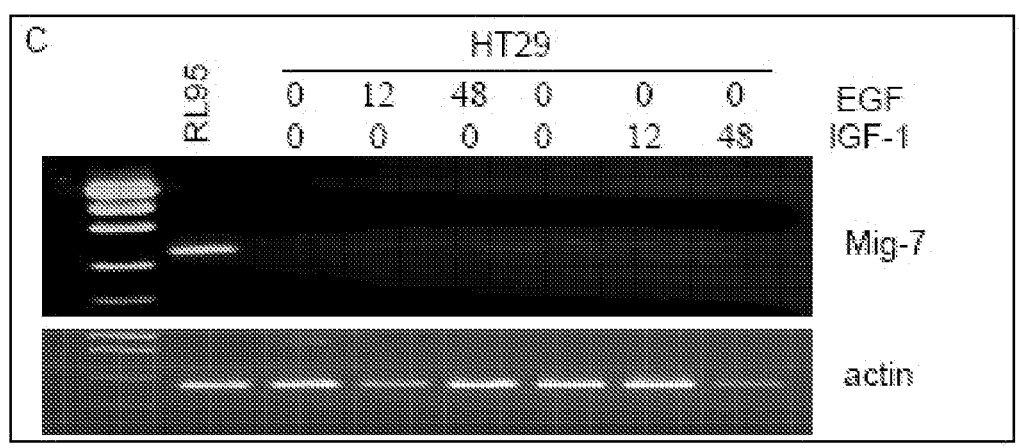

Specifically, FIGS. 11A-11C show, according to exemplary aspects of the present invention, that RTK ligands, IGF-1 and EGF, known to be produced in the tumor microenvironment, induce Mig-7 in $\alpha v \beta 5$ integrin-positive carcinoma cells but not in $\alpha v \beta 5$ negative HT29 cells. FIG. 11A shows a representative Western blot analysis of integrin $\beta 5$ expression by HT29, FG and RL95 cells. HT29 are negative while FG and RL95 are positive for $\beta 5$. FIG. 11B shows representative Northern blot analysis demonstrated that EGF and IGF-1 induce Mig-7 expression in $\beta 5+$ FG pancreatic carcinoma cells. RL95 cells express $\beta 5$ and Mig-7[1]. FIG. 11C shows that relative RT-PCR revealed that HT29 cells do not express Mig-7 mRNA. Each experiment was performed 3 times with similar results.

Cytotrophoblasts from invasive early placenta expressed Mig-7 prior to and during invasion. Mig-7 cDNA is homologous to ESTs from early placenta (1). However, non-invasive term placentas lack Mig-7 (1). Fetal cytotrophoblasts invade maternal deciduas and vasculature in early placental development prior to 22 weeks of gestation in humans behaving similar to cancer cells (7;9). Basal plate placental tissues, the invasive front of embryonic/fetal cytotrophoblasts into maternal tissue, were isolated from early, late and term placentas. Relative RT-PCR was performed as previously described (1;2). Mig-7 mRNA was found in early placenta basal plate at 7 weeks of gestation but absent from late and term placentas (FIG. 12A).

Isolated cytotrophoblasts migrate on Matrigel beginning at 12 hours after plating (8). Realtime PCR of Mig-7 mRNA expression revealed a 3-fold increase at 3 hours and at least a 7-fold statistically significant upregulation at 12 h after plating on Matrigel (FIG. 12B). Mig-7 protein levels also increased during a time course of primary fetal cytotrophoblasts plated on Matrigel. In $1^{st}$ trimester cytotrophoblasts, 12 hours Mig7 protein level increases over 0 and 3 hours on Matrigel and continues to increase at 36 hours (FIG. 12C). In $2^{nd}$ trimester cytotrophoblasts, levels of Mig-7 are again highly induced prior to invasion on Matrigel (FIG. 12D).

Figure 12A:
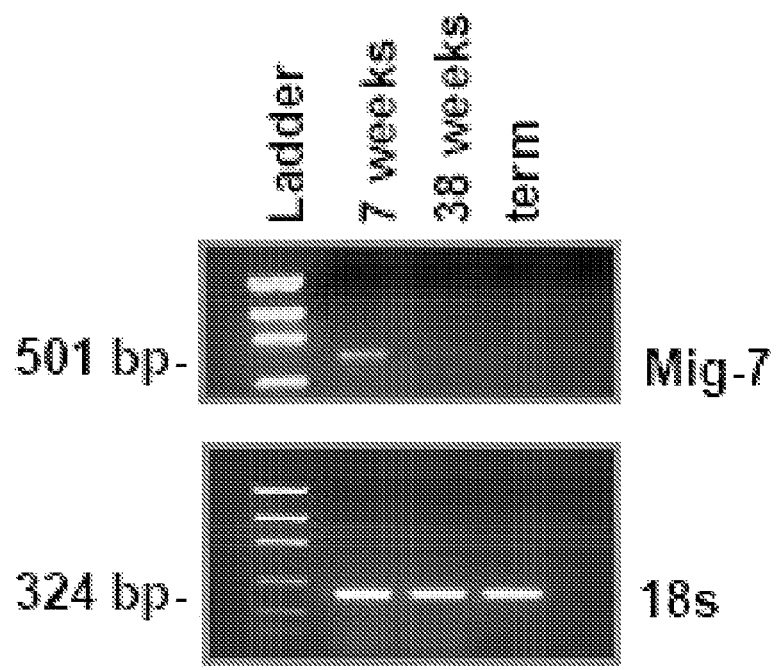
FIGS. 12A-D show, according to exemplary aspects of the present invention, that Mig-7 is expressed by invading, first and second trimester fetal cytotrophoblasts.
Figure 12B:
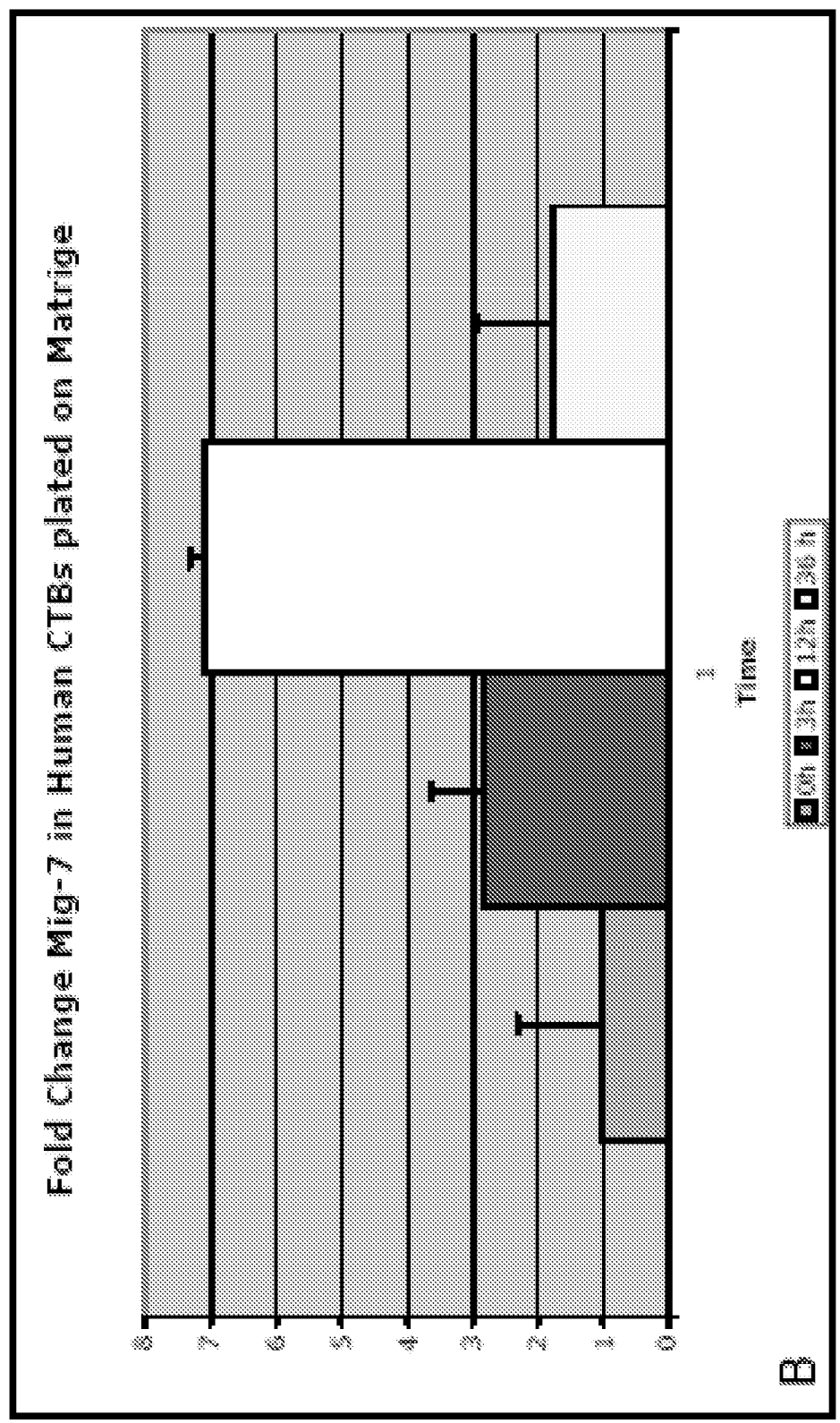
Figure 12C:
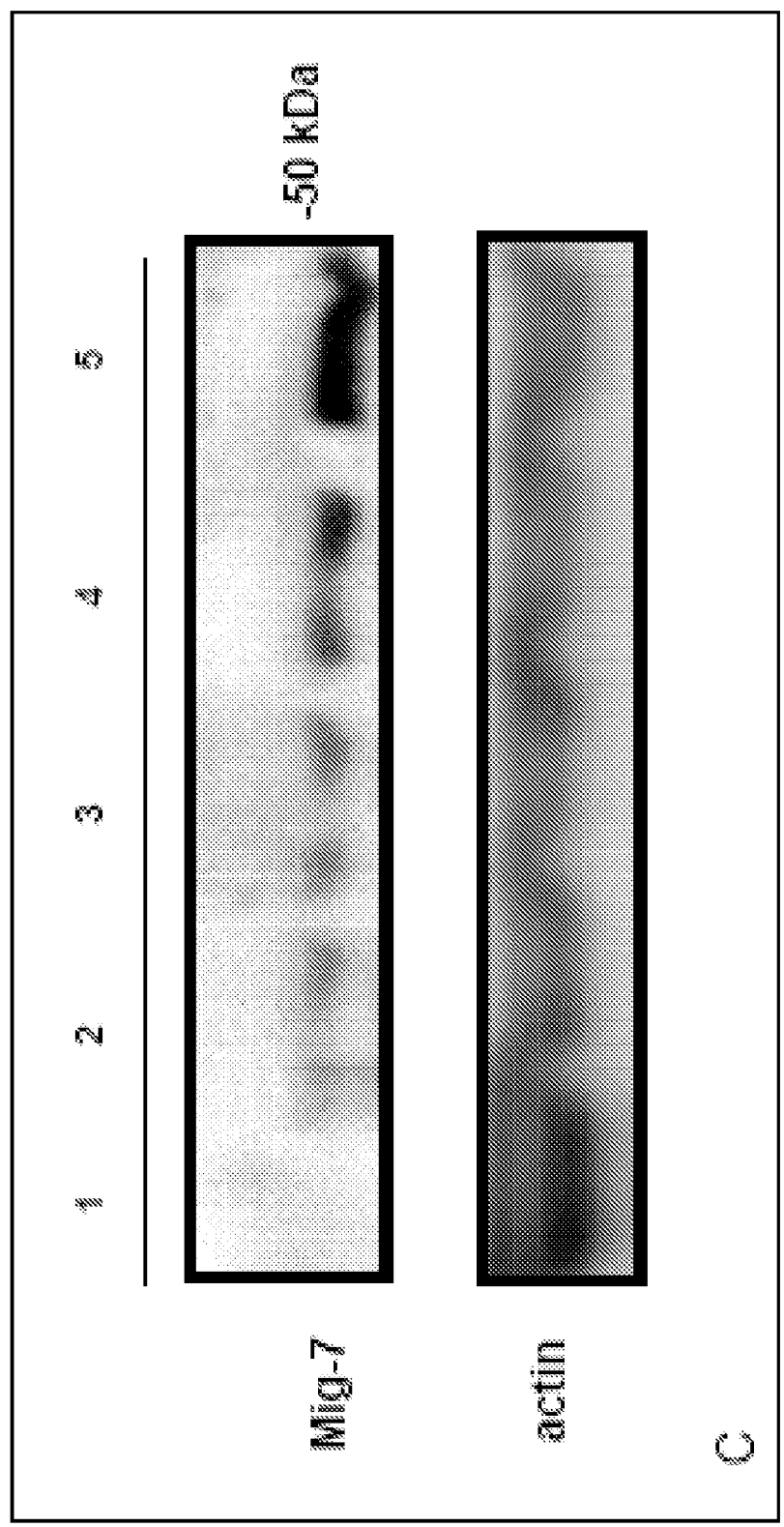
Figure 12D:
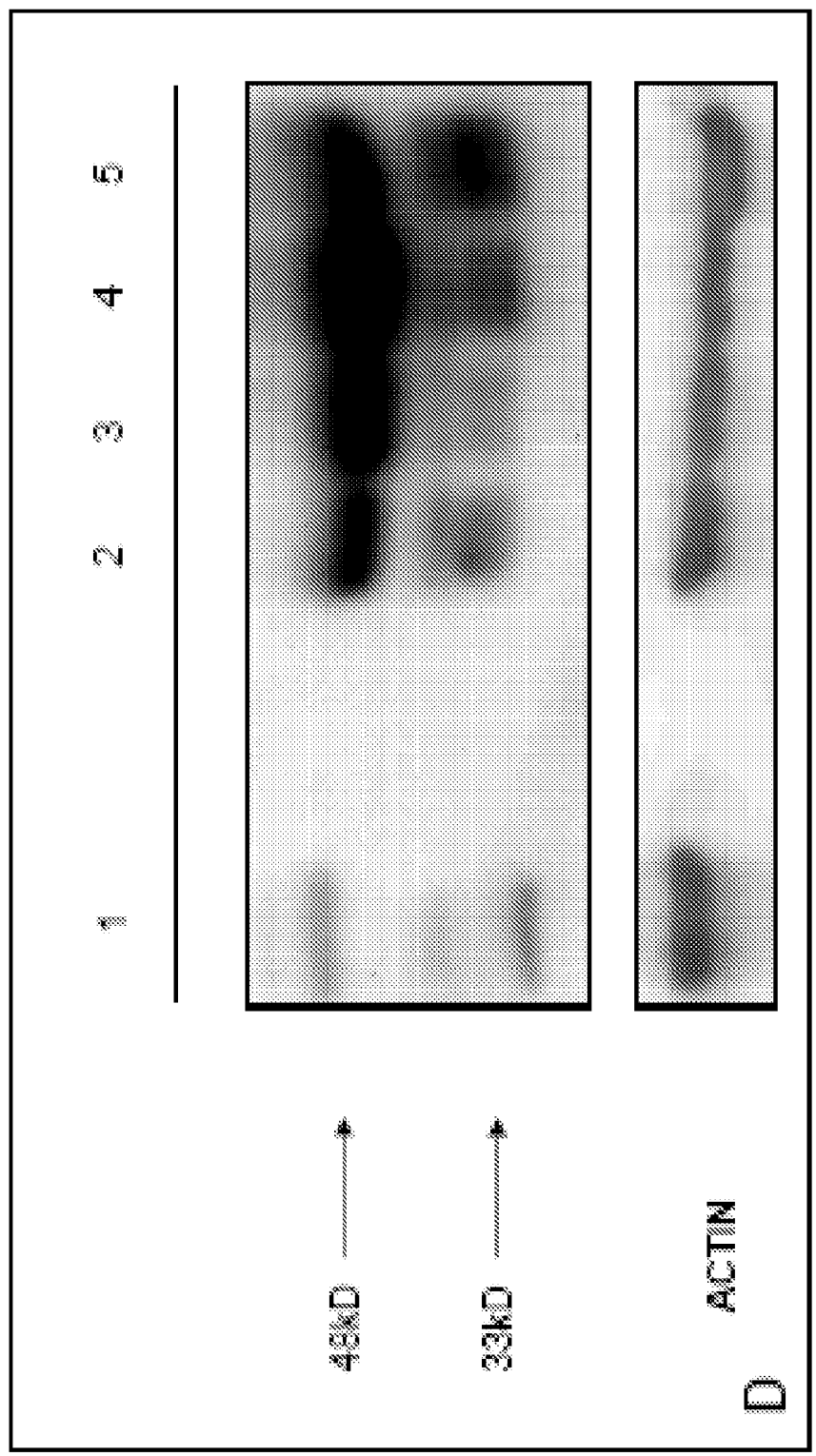

Specifically, FIGS. 12A-D show that Mig-7 is expressed by invading, first and second trimester fetal cytotrophoblasts. FIG. 12A shows a relative RT-PCR analysis of Mig-7 mRNA expression in early and late fetal-maternal interface placenta. Mig-7 mRNA is found in early invasive placenta but not in late or term placenta. FIG. 12B shows a real-time RT-PCR analysis of cytotrophoblasts plated on Matrigel. Realtime PCR of Mig-7 mRNA expression revealed a 3-fold increase at 3 hours and at least a 7-fold statistically significant upregulation at 12 h consistent with initiation of cytotrophoblast invasion at this time on Matrigel. FIG. 12C shows a representative Western blot analysis of Mig-7 in 1st trimester cytotrophoblasts plated on Matrigel. 1—platelet lysate; 2—1st trim EVTs 0 h; 3—1st trim EVTs 3 h; 4—1st trim EVTs 12 h; and 5—1st trim EVTs 36 h. D, Induction of Mig-7 protein expression in 2nd trimester cytotrophoblasts invading on Matrigel. 1—Platelet lysate; 2—2nd trim CTBs Oh; 3—2nd trim CTBs 3 h; 4—2nd trim CTBs 12 h; 5—2nd trim CTBs 36 h. CTB=cytotrophoblast.

Mig-7 expression caused decreased adhesion to laminin and was sufficient to cause vessel formation in Matrigel 3D cultures. Because HT29 cells lacked αvβ5 expression (FIG. 11A) and RTK ligands did not induce Mig-7 in this cell line (FIG. 11C), the Applicant stably transfected HT29 cells with a Mig-7 expression vector as previously described (1). FLAG-tagged Mig-7 produced by transfected HT29 cells was essentially the same size as endogenous Mig-7 expressed by either HEC1A or RL95 endometrial carcinoma cell lines (FIG. 13A).

After stable transfections, that Mig-7 expressing cells were observed to be less adherent to culture plastic. To determine if this less adherent phenotype translated to components of the extracellular matrix, adhesion assays were performed and quantified as described in Methods and Materials. Mig-7 expressing HT29 cells were significantly less adherent to laminin coated wells. Whereas, adhesion to other ECM components, fibronectin, vitronectin, collagen I or collagen IV were unaffected by Mig-7 expression (FIG. 13B).

Modification of laminins have been shown to be important for cancer cell invasion (10) and for vasculogenic mimicry (11). Mig-7 is important for cell migration in vitro and found in blood from metastatic cancer patients, primary tumors and metastatic site tumors (1;2). Applicant had not detected any phenotypic changes in HT29 Mig-7 expressing compared to nonexpressing cells in 2D cultures. Applicant used Matrigel 3D cultures which are similar to the tumor microenvironment more than 2D cultures. HT29 parental or empty vector transfected cells formed discrete colonies in 3D cultures in stark contrast to Mig-7 expressing HT29 cells that invaded and formed vessel structures (FIG. 13C).

Figure 13A:
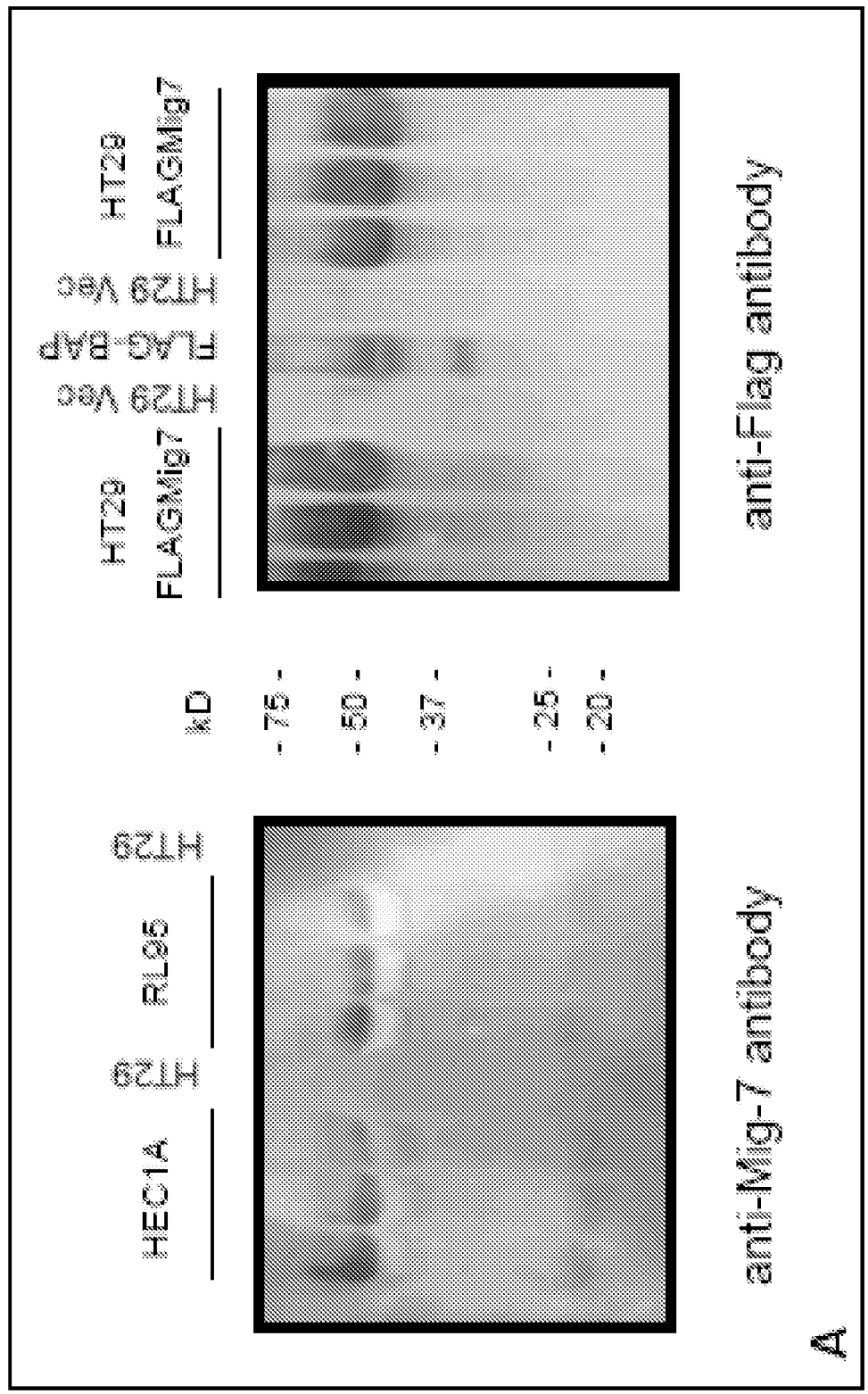
FIGS. 13A-C show, according to exemplary aspects of the present invention, that Mig-7 expression causes decreased adhesion to laminin and was sufficient to cause vessel formation in Matrigel 3D cultures.
Figure 13B:
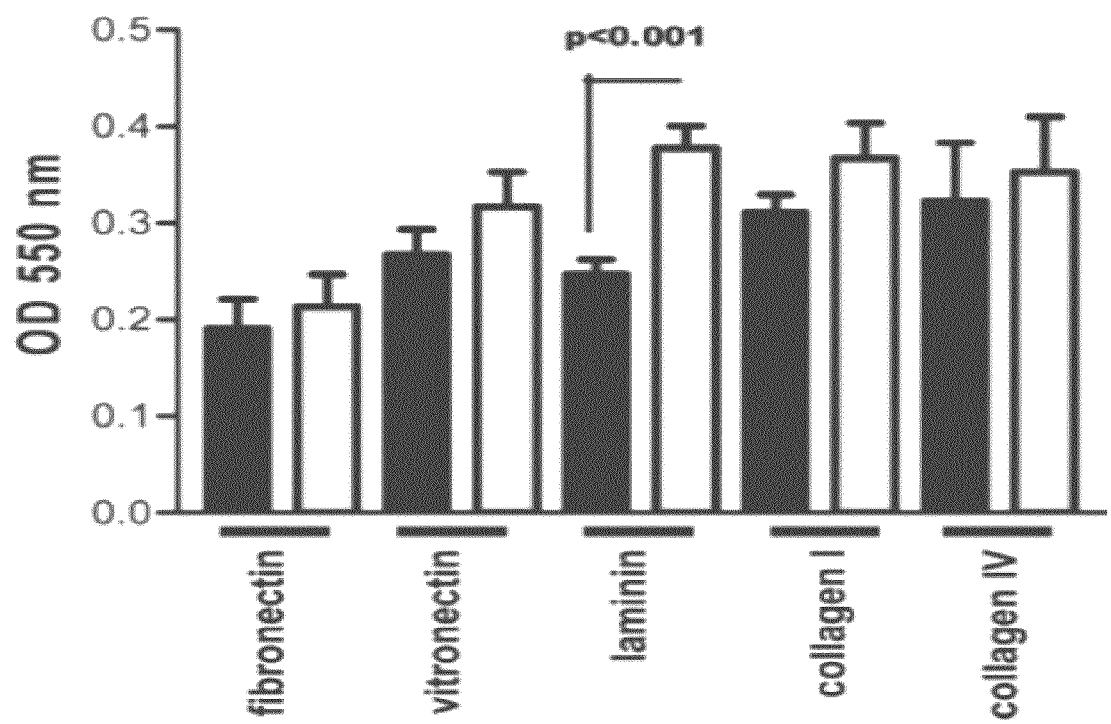
Figure 13C:
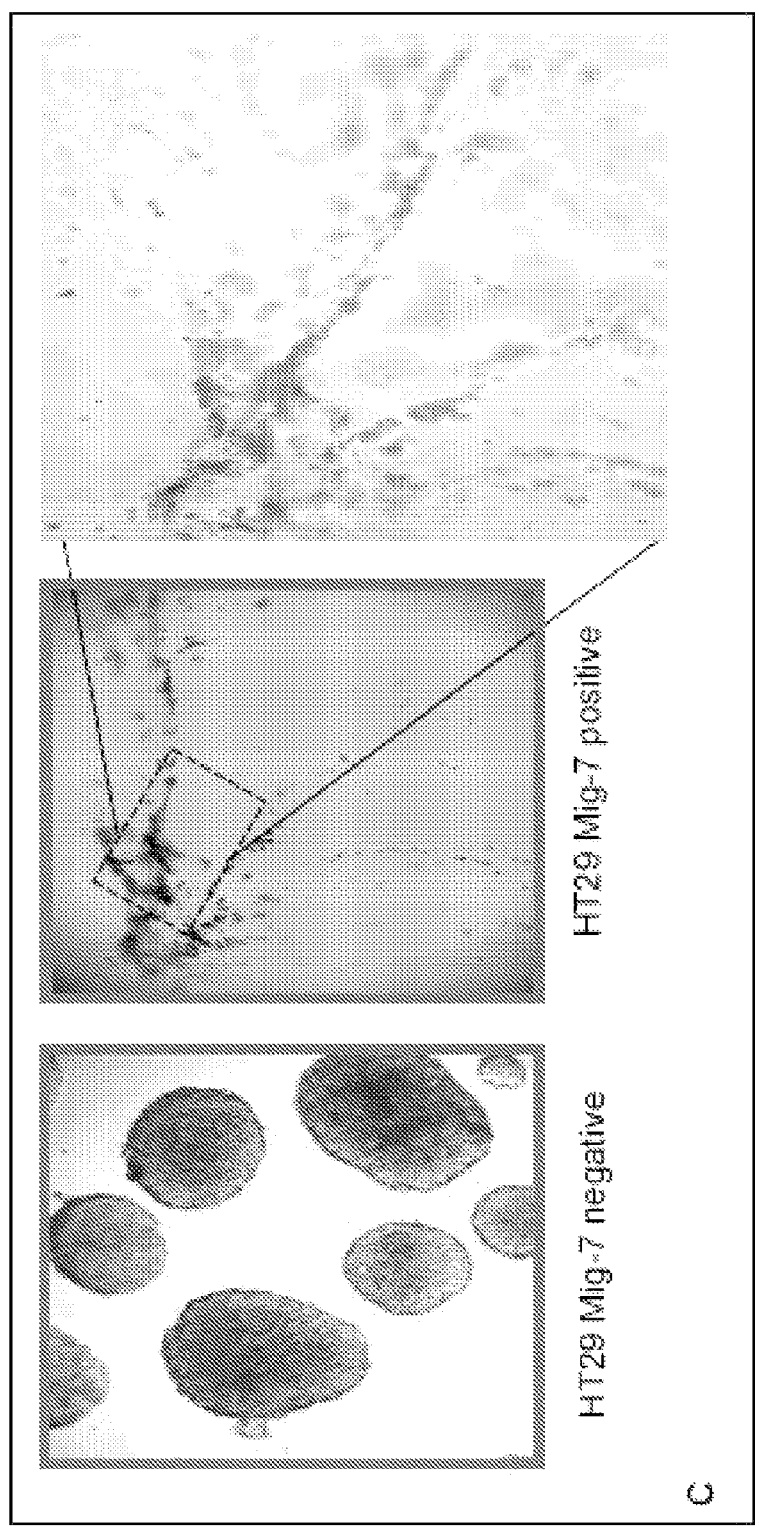

Specifically, FIGS. 13A-C show that Mig-7 expression causes decreased adhesion to laminin and was sufficient to cause vessel formation in Matrigel 3D cultures. FIG. 13 A shows that HT29 cells transfected with 3×CMVFLAG-Mig-7 expression vector express the same sized protein detected by anti-FLAG antibody as does the affinity purified Mig-7 antibody of endogenous Mig-7 in HEC1A cell lysates. Cells were plated on Matrigel for 17, 48 and 72 hours. Empty vector transfected HT29 cells are negative for FLAG Mig-7 as are parental HT29. FIG. 13B shows that HT29 Mig-7 expressing cells are >30% less adherent to a mix of laminins 1, 2, 3, 6, 8 & 10 in a statistically significant manner (p<0.001). FIG. 13C shows that HT29 cells with empty vector form discrete colonies in 3D Matrigel cultures (left panel). In contrast, HT29 cells expressing FLAG Mig-7 invade and form vessel structures (right panel and inset, supplemental data). All experiments were performed at least twice (3D cultures three times) in quadruplicate.

Tumor microenvironment growth factors, HGF, EGF or IGF-1 induce carcinoma-specific Mig-7 in αvβ5 integrin-positive cells. This redundancy suggests that the expression of Mig-7 is important for the invasive capabilities of tumor cells. αvβ5 integrin ligation is required for cytotrophoblast invasion (12) and for tumor dissemination in vivo (4;5). It is well known that these growth factors promote tumor progression and metastasis. Results suggest that multiple growth factors of the tumor microenvironment induce Mig-7 which accounts for its expression in virtually all cancer samples (n>240) irrespective of tissue of origin (1;2). When cancer cell lines are plated on Matrigel, which contains all of these growth factors, Mig-7 protein levels are elevated. Inclusion of Mig-7 sequences on microarrays will help further define its regulation at the mRNA level.

Early placenta, which is the invasive stage of placenta development, expresses Mig-7 mRNA consistent with previous data of ESTs from early placenta are homologous with Mig-7 cDNA (1). Fetal cytotrophoblasts from placenta prior to 22 weeks of gestation mimic behavior of invasive tumor cells (6). Fetal cytotrophoblasts express Mig-7 mRNA and protein when plated on Matrigel for 12 hours at seven fold higher levels than those initially plated. This is the time period in which cytotrophoblasts start invasion on Matrigel (13) suggesting Mig-7 may play a role in their invasion. Fetal cytotrophoblasts from second trimester express Mig-7 consistent with a potential role for Mig-7 in endovascular invasion by these cells during the second trimester (12). Aggressive tumor cells also endovascularly invade in order to metastasize. Interestingly, EGF acts as a chemoattractant for intravasation of blood vessels by tumor cells (14).

Mig-7 causes significantly lower adhesion to culture plastic and to laminins (FIG. 13B). Laminin is a major component of Matrigel and the basement membrane of epithelial structures and has been shown to play an important role in tumor cell behaviors (10). Therefore, because Mig-7 makes cells less adhesive to laminin this may facilitate tumor cell invasion. By bringing important mediators together at the cell membrane through one or more of its cysteine residues, Mig-7 may play also play a role in production of Laminin 5 gamma 2 promigratory fragments which would make cells less adherent to laminins.

Notably, Mig-7 expression in HT29 cells is sufficient and necessary for vessel formation in 3D cultures (FIG. 13C) suggesting that Mig-7 allows sensing of the microenvironment. Localization of Mig-7 protein to cells of vessel structures in lymph nodes to which human carcinoma cells spread in the nude mouse model of metastasis implies that either these cells are forming vessels due to their Mig-7 expression or that these cells are intravasating or extravasating. No difference in phenotype, other than a lack of adherence, is observed in 2D cultures on plastic or Matrigel (See Example 1 and 3 herein). Plasticity of tumor cells that form vessels has been termed vasculogenic mimicry and predicts poor patient outcome. The formation of laminin 5 gamma 2 promigratory fragments and the presence of EphA2 are important for the process of vasculogenic mimicry (3). Cysteine rich Laminin 5 gamma 2 fragments have also been shown to be important in other epithelial invasion as well as migration and is not restricted to aggressive cancer cells (10). EphA2, another cysteine-rich protein, is localized at the membrane and phosphorylated differentially between normal and malignant cells. Importantly, a different phenotype is also observed with transformed cells overexpressing EphA2 in 3D cultures as compared to 2D cultures. EphA2 is also found on chromosome 1 as is Mig-7 in a "hot spot" for cancer (15). Because EphA2 or Mig7 expression imparts dramatically different phenotypes in 3D cultures, it is tempting to speculate that they may be associated.

It has been proposed that finding a protein specific to vasculogenic mimicry would be an excellent anti-cancer target because this process does not occur in any normal tissue in children or adults. Additionally, invading cancer cells are resistant to cancer therapies targeting cell growth (14). Therefore, therapies directed specifically to invading cancer cells are needed. According to particular aspects, Mig-7 provides a carcinoma-, invasion-specific target to inhibit invasion and vessel formation in vivo preventing dissemination of tumor cells and death. The facts that Mig-7 is induced by growth factors that regulate PI3K, a signaling pathway required for vasculogenic mimicry (16), is localized to vessels in metastases, causes vessel-like formation as well as invasion, collectively indicates that Mig7, at least in part, controls invasion and vasculogenic mimicry in tumor cells.

References Relating to this Example 3

(1) Crouch S, Spidel C S, Lindsey J S. HGF and ligation of αvβ5 integrin induce a novel, cancer cell-specific gene expression required for cell scattering. Experimental Cell Research 2004; 292(2):274-87.

(2) Phillips T M, Lindsey J S. Carcinoma Cell-specific Mig-7: A new potential marker for circulating and migrating cancer cells. Oncology Reports 2005; 13:37-44.

(3) Hendrix M J C, Seftor E A, Kirschmann D A, Quaranta V, Seftor R E B. Remodeling of the Microenvironment by Aggressive Melanoma Tumor Cells. Ann NY Acad Sci 2003 May 1; 995(1):151-61.

(4) Brooks P C, Klemke R L, Schon S, Lewis J M, Schwartz M A, Cheresh D A. Insulin-like growth factor receptor cooperates with integrin alpha v beta 5 to promote tumor cell dissemination in vivo. Journal of Clinical Investigation 1997; 99(6):1390-8.

(5) Klemke R L, Yebra M, Bayna E M, Cheresh D A. Receptor tyrosine kinase signaling required for integrin alpha v beta 5-directed cell motility but not adhesion on vitronectin. Journal of Cell Biology 1994; 127(3):859-66.

(6) Folberg R, Hendrix M J C, Maniotis A J. Vasculogenic mimicry and tumor angiogenesis. American Journal of Pathology 2000; 156(2):361-81.

(7) Fisher S J, Cui T Y, Zhang L, Hartman L, Grahl K, Zhang G Y, et al. Adhesive and degradative properties of human placental cytotrophoblast cells in vitro. J Cell Biol 1989 Aug. 1; 109(2):891-902.

(8) Librach C L, Werb Z, Fitzgerald M L, Chiu K, Corwin N M, Esteves R A, et al. 92-kD type IV collagenase mediates invasion of human cytotrophoblasts. J Cell Biol 1991 Apr. 1; 113(2):437-49.

(9) Soundararajan R, Rao A J. Trophoblast 'pseudo-tumorigenesis': Significance and contributory factors. Reproductive Biology and Endocrinology 2004; 2(1):15.

(10) Givant-Horwitz V, Davidson B, Reich R. Laminin-induced signaling in tumor cells. Cancer Letters 2005; 223: 1-10.

(11) Seftor R E B, Seftor E A, Koshikawa N, Meltzer P S, Gardner L M G, Bilban M, et al. Cooperative interactions of Laminin 52 Chain, Matrix Metalloproteinase-2, and Membrane Type-1 Matrix/Metalloproteinase are required for mimicry of embryonic vasculogenesis by aggressive melanoma. Cancer Res 2001; 61:6322-7.

(12) Zhou Y, Fisher S J, Janatpour M, Genbacev 0, Dejana E, Wheelock M, et al. Human cytotrophoblasts adopt a vascular phenotype as they differentiate. Journal of Clinical Investigation 1997; 99(9):2139-51.

(13) Janatpour M J, McMaster M T, Genbacev 0, Zhou Y, Dong J, Cross J C, et al. Id-2 regulates critical aspects of human cytotrophoblast differentiation, invasion and migration. Development 2000 Feb. 1; 127(3):549-58.

(14) Condeelis J, Singer R H, Segall J E. THE GREAT ESCAPE: When Cancer Cells Hijack the Genes for Chemotaxis and Motility. Annual Review of Cell and Developmental Biology 2005; 21 (1):695-718.

(15) Walker-Daniels J, Hess A R, Hendrix M J C, Kinch M S. Differential regulation of EphA2 in normal and malignant cells. American Journal of Pathology 2003; 162(4):1037-42.

(16) Hess A R, Seftor E A, Seftor R E B, Hendrix M J C. Phosphoinositide 3-Kinase Regulates Membrane Type 1-Matrix Metalloproteinase (MMP) and MMP-2 Activity during Melanoma Cell Vasculogenic Mimicry. Cancer Res 2003 Aug. 15; 63(16):4757-62.

The invention claimed is:

1. A process for treating or protecting from cancer cell invasion or metastasis, comprising administering a therapeutically effective amount of an anti-cancer vaccine comprising an amino acid sequence consisting of SEQ ID NO: 2, 3, or 4, or a combination thereof with a pharmaceutically acceptable carrier to isolated peripheral blood monocyte cells or to other isolated immune cells which are then administered to a subject.

2. A process for treating cancer or protecting from cancer cell invasion or metastasis, comprising administering to a subject in need thereof, a therapeutically effective amount of an anti-cancer vaccine comprising an amino acid sequence consisting of SEQ ID NO: 2, 3, or 4, or a combination thereof with a pharmaceutically acceptable carrier, wherein cancer or metastasis is treated.

3. A process for protecting a subject from cancer cell invasion comprising administering to a subject in need thereof, an immunoprotective amount of an anti-cancer vaccine comprising an amino acid sequence consisting of SEQ ID NO: 2, 3, or 4, or a combination thereof, wherein said vaccine may include a conjugated or nonconjugated adjuvant or may be administered by non-viral delivery vehicle; wherein said vaccine includes a pharmaceutically acceptable carrier.

* * * * *

SEQUENCE LISTING

```
<160> NUMBER OF SEQ ID NOS: 47

<210> SEQ ID NO 1
<211> LENGTH: 1617
<212> TYPE: DNA
<213> ORGANISM: Homo sapiens

<400> SEQUENCE: 1
gtgcctctct atggagagca cctctgtggc ctctctgaga gcactcacag ccaaaagtac      60
acagctgccc ccaggctgag agtgcttgat acaccttga atccctctt atatgatgcc      120 ccagcccagg agagataaaa gcatcagcac catgagattc acctgcctct ggtcgttagg      180
gaacaatgga ggcctgcgat tggagttaaa ctctcagtga tctctgtgtt gacaacacca      240
aagctagagg aatccagtag gatgtgggca tggttttccc ggaaggctga ctgagcagtt      300
ctgcaaatgt ttgcaagtac agggcagaat ttcatccagc ctcagaacct tgagccaaga      360
```

```
ctcagcatca gcaaagccaa aagtttcatt tcttcgactg tgggagtgct agtcccaacc    420
tttagatggc cattcagttt taagttcaat aagcattttg attgagaaat actttgctga    480
ggagtgaaaa gtccttggct ttgaaagacg aatgatgagc agttcagtgg cccatgtcac    540
agtccaggca cctgccaaag gtgactccct gggaggagca tcttagtcac agagccagtg    600
cctgctgtag gtgtgcagaa gggtgcatgt gtgtgtgtgt gtgtgtgtgt gtatgtgtac    660
gtgtacatgt gtgttggggg aagggagcaa gggttgtggg agcatttctt atctgctctt    720
ctctgcaaga tttcctgtga tttaagtcac attaaagtac ccataagccc gtaatgcaaa    780
agaaccccaa aaccagccca gcagccaacc atggcagcaa gtagatgctc tggtctttag    840
atagtcagaa atgacacttc tgggctctca ggcagtcagt gggttgagct ccccattaaa    900 gtcccctgc caagtctgga atagtcctag tcccgtgtgt gtgtgtgtgt gtgtgtgtgt    960
gtgtgtgtgt acccgcgtgc atatgcgcgc atgcagtgca gggtctgcat acctaaagca   1020
gatgaaattc tgcagaatgg ctgcctcgct agacaaagtc aagaagacag accgaggaga   1080
gagaggttga tgtgtctcca ctaccaagag acaggcttct ctaagccagc gagacatccc   1140
atccaacaat atgaaactgg ccacatttcc ttgagatgtc aacgttgaaa gtgtagctgc   1200
atctttattc ttcactgtta tgaagttggg tgcaacacag cttgagtgga atacaaaaac   1260
accgcttgga aacacatgat ctggatttga atcgcagctg tatcattcac tgctataga    1320 ctctgagcaa gacctctctg aggttatttc ttcacagtag gtagagacaa gacttacttc   1380
aaaggttctt aaagttgaac ctgagtcaat gaatgcaaaa gtgttcacat ttaaactgta   1440
attttaaagc acaatacaag taaatagcat taatatcatt agagagatta acttagcact   1500
gtgcgtcaca tgattcatca cggccatctg tgagatatca aatagagagg tgaagcctgc   1560
agtaataaaa aatactgcca tagctataaa aaaaaaaaaa aaaaaaaaaa aaaaaaa     1617
```

<210> SEQ ID NO 2
<211> LENGTH: 18
<212> TYPE: PRT
<213> ORGANISM: Homo sapiens

<400> SEQUENCE: 2

Arg Val His Met Arg Ala Cys Ser Ala Gly Ser Ala Tyr Leu Lys Gln
 1               5                  10                  15

Met Lys

<210> SEQ ID NO 3
<211> LENGTH: 18
<212> TYPE: PRT
<213> ORGANISM: Homo sapiens

<400> SEQUENCE: 3

Gly Ser Ala Tyr Leu Lys Gln Met Lys Phe Cys Arg Met Ala Ala Ser
 1               5                  10                  15

Leu Asp

<210> SEQ ID NO 4
<211> LENGTH: 20
<212> TYPE: PRT
<213> ORGANISM: Homo sapiens

<400> SEQUENCE: 4

Phe Cys Arg Met Ala Ala Ser Leu Asp Lys Val Lys Lys Thr Asp Arg
 1               5                  10                  15

Gly Glu Arg Gly
            20

<210> SEQ ID NO 5
<211> LENGTH: 18
<212> TYPE: PRT
<213> ORGANISM: Homo sapiens

<400> SEQUENCE: 5

Met Ala Ala Ser Arg Cys Ser Gly Leu Tyr Ile Val Arg Asn Asp Thr
1               5                   10                  15

Ser Gly

<210> SEQ ID NO 6
<211> LENGTH: 18
<212> TYPE: PRT
<213> ORGANISM: Homo sapiens

<400> SEQUENCE: 6

Tyr Ile Val Arg Asn Asp Thr Ser Gly Leu Ser Gly Ser Gln Trp Val
1               5                   10                  15

Asp Ser

<210> SEQ ID NO 7
<211> LENGTH: 18
<212> TYPE: PRT
<213> ORGANISM: Homo sapiens

<400> SEQUENCE: 7

Leu Ser Gly Ser Gln Trp Val Asp Ser Pro Leu Lys Ser Pro Cys Gln
1               5                   10                  15

Val Trp

<210> SEQ ID NO 8
<211> LENGTH: 9
<212> TYPE: DNA
<213> ORGANISM: Homo sapiens

<400> SEQUENCE: 8 gtgcctctc                                                                9

<210> SEQ ID NO 9
<211> LENGTH: 535
<212> TYPE: DNA
<213> ORGANISM: Homo sapiens
<220> FEATURE:
<221> NAME/KEY: misc_feature
<222> LOCATION: 1, 8, 451, 462, 467, 481, 483, 487, 508, 515, 519, 527,
      535
<223> OTHER INFORMATION: n = a,t,c or g

<400> SEQUENCE: 9
nggaattngt ttacgactca ctacagggcg aattgggcct ctagatgctg ctcgagcggc    60
cgccagtgtg atggatatct gcagaattcg gcttgaacac tgcgtttgct ggctttgatg   120
aaattaagcc acattaaagt acccataagc ccataatgca aaagaacccc aaaaccagcc   180
cagcagccaa ccatggcagc aagtagatgc tctggtcttt agatagtcag aaatgacact   240
tctgggctct caggcagtca gtgggttgag ctccccatta agtccccct gccaagtctg    300 gaatagtcct agtcccgtgt gtgtgtgtgt gtgtgtgtgt gtgtgtgtgt gtgtgtgtgt   360
gtgtgtgtgt acccgcgtgc atatgcgcgc atgcagtgca gggtctgcat acctaaagca   420

```
gatgaaattc tgcagaatgg ctgcctccta nacaaagtca anaaganaga acgaggagcc    480
nantccncac actggcgggc gttactantg gatcnaacnc ggtacanctg aagcn         535

<210> SEQ ID NO 10
<211> LENGTH: 543
<212> TYPE: DNA
<213> ORGANISM: Homo sapiens
<220> FEATURE:
<221> NAME/KEY: misc_feature
<222> LOCATION: 3, 7, 14, 16, 23, 453, 470, 479, 481, 484, 486, 510, 543
<223> OTHER INFORMATION: n = a,t,c or g

<400> SEQUENCE: 10
tancgcnaat gctnanttag gtnacactat agaatactca agctatgcat caagcttggt    60
accgagctcg gatccactag taacggccgc cagtgtgctg gaattcggct tgaacactgc   120
gtttgctggc tttgatgaaa ttaagtcaca ttaaagtacc cataagccca taatgcaaaa   180 gaacccaaa accagcccag cagccaacca tggcagcaag tagatgctct ggtctttaga    240
tagtcagaaa tgacacttct gggctctcag gcagtcagtg ggttgagctc cccattaaag   300 tcccctgcc aagtctggaa tagtcctagt cccgtgtgtg tgtgtgtgtg tgtgtgtgtg    360
tgtgtgtgtg tgtgtgtgtg tgtgtgtgta ccgcgtgcat atgcgcgcat gcagtgcagg   420
gtctgcatac ctaaagcaga tgaaattctg canaatggct gcctcactan acaaagtcna   480
naananagaa cgaggaaccg aattctgcan atatccacac actgggggc gctcgaacag    540 ctn                                                                 543

<210> SEQ ID NO 11
<211> LENGTH: 546
<212> TYPE: DNA
<213> ORGANISM: Homo sapiens
<220> FEATURE:
<221> NAME/KEY: misc_feature
<222> LOCATION: 1, 3, 4, 9, 15, 18, 47, 53, 501
<223> OTHER INFORMATION: n = a,t,c or g

<400> SEQUENCE: 11
ngnnaattng ttttnacnga ctcactgata gggcgaattg ggcctcntag tangcatgct    60
cgagcggccg ccagtgtgat ggatatctgc agaattcggc ttcctcggtc tgtcttcttg   120
actttgtcta gtgaggcagc cattctgcag aatttcatct gctttaggta tgcagaccct   180
gcactgcatg cgcgcatatg cacgcgggta cacacacaca cacacacaca cacacacaca   240
cacacacaca cacacacaca cacacgggac taggactatt ccagacttgg caggggact    300 ttaatgggga gctcaaccca ctgactgcct gagagcccag aagtgtcatt tctgactatc   360
taaagaccag agcatctact tgctgccatg gttggctgct gggctggttt tggggttctt   420
ttgcattatg ggcttatggg tactttaatg tgacttaatt tcatcaaagc cagcaaacgc   480
agtgttcaag ccgaattcca ncacactggc gggcgttact aatggatcga actcggtaca   540
agctta                                                              546

<210> SEQ ID NO 12
<211> LENGTH: 540
<212> TYPE: DNA
<213> ORGANISM: Homo sapiens
<220> FEATURE:
<221> NAME/KEY: misc_feature
<222> LOCATION: 7, 10, 27, 60, 64, 67, 509, 540
<223> OTHER INFORMATION: n = a,t,c or g
```

<400> SEQUENCE: 12

```
ggggttnctn atttagtgtc cacactnata gaatactcaa gctatgcatc aagcttggtn    60
accnganctc ggatccacta gtaacggccg ccagtgtgct ggaattcggc tcctcggtct   120
gtcttcttga ctttgtctag tgaggcagcc attctgcaga atttcatctg ctttaggtat   180
gcagaccctg cactgcatgc gcgcatatgc acgcgggtac acacacacac acacacacac   240
acacacacac acacacacac acacacacac acgggactag gactattcca gacttggcag   300
ggggacttta atggggagct caacccactg actgcctgag agcccagaag tgtcatttct   360
gactatctaa agaccagagc atctacttgc tgccatggtt ggctgctggg ctggttttgg   420
ggttcttttg cattatgggc ttatgggtac tttaatgtgg cttaatttca tcaaagccac   480
aaacgcagtg ttcaagccga attctgcana tatccatcac actggcgggc gctcaaactn   540
```

<210> SEQ ID NO 13
<211> LENGTH: 542
<212> TYPE: DNA
<213> ORGANISM: Homo sapiens
<220> FEATURE:
<221> NAME/KEY: misc_feature
<222> LOCATION: 6, 12, 14, 21, 26, 31, 501, 536, 542
<223> OTHER INFORMATION: n = a,t,c or g

<400> SEQUENCE: 13

```
ttcgcnatgc tnanttaggt nacctnatag naatactcaa gctatgcatc aagcttggta    60
ccgagctcgg atccactagt aacggccgcc agtgtgctgg aattcggctt cctcggtctg   120
tcttcttgac tttgtctagt gaggcagcca ttctgcagaa tttcatctgc tttaggtatg   180
cagaccctgc actgcatgcg cgcatatgca cgcgggtaca cacacacaca cacacacaca   240
cacacacaca cacacacaca cacacacaca cacgcgggac taggactatt ccagacttgg   300
caggggact ttaatgggga gctcaaccca ctgactgcct gagagcccag aagtgtcatt   360
tctgactatc taaagaccag agcatctact tgctgccatg gttggctgct gggctggttt   420
tggggttctt ttgcattatg ggcttatggg tactttaatg tgacttaatt tcatcaaagc   480
cacaaaccag tgttcaagcc naattctgca aatatccaca cactggcggg cgctcnaaca   540
tn                                                                  542
```

<210> SEQ ID NO 14
<211> LENGTH: 547
<212> TYPE: DNA
<213> ORGANISM: Homo sapiens
<220> FEATURE:
<221> NAME/KEY: misc_feature
<222> LOCATION: 3, 4, 5, 6, 7, 8, 9, 10, 50, 395, 412, 435, 437, 459,
    463, 466, 467, 468, 476, 481, 492, 499, 501, 504, 510, 516, 519,
    530, 538, 547
<223> OTHER INFORMATION: n = a,t,c or g

<400> SEQUENCE: 14

```
tannnnnnnn ggaatttgtc ctacgactca ctcgagggcg aattgggcan tctatatgct    60
gctcgagcgg ccgccagtgt gatggatatc tgcagaattc ggcttgaaca ctgcgtttgc   120
tggctttgat gaaattaagt cacattaaag taccctaaag cccataatgc aaaagaaccc   180
caaaaccagc ccagcagcca accatggcag caagtagatg ctctggtctt tagatagtca   240
gaaatgacac ttctgggctc tcaggcagtc agtgggttga gctccccatt aaagtccccc   300
tgccaagtct ggaatagtcc tagtcccgtg tgtgtgtgtg tgtgtgtgtg tgtgtgtgtg   360
tgtgtgtgtg tgtgtgtgtg tacccgcgtg catangcgcg catgcagtgc tnggtctgca   420
```

-continued

```
tacctaaaac aaatnanatc tgcagaatgg gctgcctcnc tanacnnntc aaaaanacga        480
ngaaggaaac cnaattccnc nccnggcggn cgttantant ggatccagcn cggtaccngc        540 tgaagcn                                                                 547
```

<210> SEQ ID NO 15
<211> LENGTH: 546
<212> TYPE: DNA
<213> ORGANISM: Homo sapiens
<220> FEATURE:
<221> NAME/KEY: misc_feature
<222> LOCATION: 3, 14, 16, 21, 31, 443, 474, 485, 488, 529, 538, 546
<223> OTHER INFORMATION: n = a,t,c or g

<400> SEQUENCE: 15

```
tancgcaatt gctnanttag ngtccacact natagaatac tcaagctatg catcaagctt        60
ggtaccgagc tcggatccac tagtaacggc cgccagtgtg ctggaattcg cttgaacac        120 tgcgtttgct ggctttgatg aaattaagtc acattaaagt acccataagc ccataatgca       180
aaagaacccc aaaaccagcc cagcagccaa ccatggcagc aagtagatgc tctggtcttt       240
agatagtcag aaatgacact tctgggctct caggcagtca gtgggttgag ctccccatta       300 aagtcccccct gccaagtctg gaatagtcct agtcccgtgt gtgtgtgtgt gtgtgtgtgt      360
gtgtgtgtgt gtgtgtgtgt gtgtgtgtgt gtacccgcgt gcatatgcgc gcatgcagtg      420
cagggtctgc atacctaaag canatgaaat tctgcagaat ggctgcctca ctanacaaag       480
tcaanaanac agaacgagga agcgaattcc gcaaatatcc accactgggng ggcgctcnag      540 catgcn                                                                  546
```

<210> SEQ ID NO 16
<211> LENGTH: 536
<212> TYPE: DNA
<213> ORGANISM: Homo sapiens
<220> FEATURE:
<221> NAME/KEY: misc_feature
<222> LOCATION: 6, 85, 405, 442, 455, 459, 469, 471, 472, 494, 512, 531
<223> OTHER INFORMATION: n = a,t,c or g

<400> SEQUENCE: 16

```
ggaatngttt tacgactcac tgcgagggcg aattgggcac tctagatgct gctcgagcgg        60
ccgccagtgt gatggatatc tgcanaattc ggcttgaaca ctgcgtttgc tggctttgat       120
gaaattaagt cacattaaag tacccataag cccataatgc aaaagaaccc caaaaccagc       180
ccagcagcca accatggcag caagtagatg ctctggtctt tagatagtca gaaatgacac       240
ttctgggctc tcaggcagtc agtgggttga gctccccatt aaagtccccc tgccaagtct       300
ggaatagtcc tagtcccgtg tgtgtgtgtg tgtgtgtgtg tgtgtgtgtg tgtgtgtgtg       360
tgtgtgtgtg tgtgtacccg cgtgcatatg cgcgcatgca gtgcnggtc tgcataccta       420 aagcagatga atctgcaga anggctgctc actanacana gtcaagaana nngacgagga       480
agccgaattc cccnnctggg gggcgttact antggatcga gctcggtaca ncttga          536
```

<210> SEQ ID NO 17
<211> LENGTH: 538
<212> TYPE: DNA
<213> ORGANISM: Homo sapiens
<220> FEATURE:
<221> NAME/KEY: misc_feature
<222> LOCATION: 3, 5, 8, 15, 19, 25, 32, 65, 395, 402, 404, 417, 418,
      422, 437, 442, 444, 461, 465, 467, 470, 472, 489, 497, 513, 516,
      518, 521, 530, 534, 535, 538

<223> OTHER INFORMATION: n = a,t,c or g

<400> SEQUENCE: 17

```
ttncngcnat tgctnattna gggtncacac tnatagaata ctcaagctat gcatcaagct    60
tgggnaccga gctcggatcc actagtaacg gccgccagtg tgctggaatt cggcttgaac   120
actgcgtttg ctggctttga tgaaattaag tcacattaaa gtacccataa gcccataatg   180
caaaagaacc ccaaaaccag cccagcagcc aaccatggca gcaagtagat gctctggtct   240
ttagatagtc agaaatgaca cttctgggct ctcaggcagt cagtgggttg agctccccat   300
taaagtcccc ctgccaagtc tggaatagtc ctagtcccgt gtgtgtgtgt gtgtgtgtgt   360
gtgtgtgtgt gtgtgtgtgt gtgtgtgtgt gtacncgcgt gnanatgcgc gcatggnntg   420
cngggtctgc atacaanagc ananaaaatc tgcagaatgg ntgcncnctn anaagtctaa   480
aaacaaacna ggagccnaaa tctgcaaaat ccnccncngg nggcgccaan atannctn    538
```

<210> SEQ ID NO 18
<211> LENGTH: 548
<212> TYPE: DNA
<213> ORGANISM: Homo sapiens
<220> FEATURE:
<221> NAME/KEY: misc_feature
<222> LOCATION: 1, 2, 3, 4, 11, 15, 268, 283, 284, 290, 298, 310, 323,
      331, 334, 337, 341, 366, 368, 370, 383, 403, 416, 433, 434, 445,
      453, 458, 461, 463, 466, 469, 472, 485, 500, 512, 517, 524,
      537, 546, 548
<223> OTHER INFORMATION: n = a,t,c or g

<400> SEQUENCE: 18

```
nnnnggaatt ngttntacga ctcacttata gggcgaattg ggcctctaga tgcatgctcg    60
agcggccgcc agtgtgatgg atatctgcag aattcggctt cctcggtctg tcttcttgac   120
tttgtctagt gaggcagcca ttctgcagaa tttcatctgc tttaggtatg cagaccctgc   180
actgcatgcg cgcatatgca cgcgggtaca cacacacaca cacacacaca cacacacaca   240
cacacacaca cacacacaca cggggacnac gacaattcca canntggacn ggggacntt    300
aatggggagn tcaacccact gantgcctga nagnccncaa ntgtcttttc tgactatcta   360
aagacnanan catctacttg ctnccatggt tggctgctgg gcngggtttt ggggtnctct   420
tgcattatgg gcnnatgggt atttnatgtg acntaatntc ncnaanccnc tnacgcagtg   480
ttcancccga attccagcan actggggcg tnaatantgg atcnaactcg gtacaancгt   540
gatcantn                                                           548
```

<210> SEQ ID NO 19
<211> LENGTH: 548
<212> TYPE: DNA
<213> ORGANISM: Homo sapiens
<220> FEATURE:
<221> NAME/KEY: misc_feature
<222> LOCATION: 2, 3, 5, 8, 15, 18, 22, 32, 64, 507, 541, 548
<223> OTHER INFORMATION: n = a,t,c or g

<400> SEQUENCE: 19

```
tnncngcnat tgctnatnta gngtggacac tnatagaata ctcaagctat gcatcaagct    60
tggntaccga gctcggatcc actagtaacg gccgccagtg tgctggaatt cggcttcctc   120
ggtctgtctt cttgactttg tctagtgagg cagccattct gcagaatttc atctgcttta   180
ggtatgcaga ccctgcactg catgcgcgca tatgcacgcg gtacacacac acacacaca    240
cacacacaca cacacacaca cacacacaca cacacacaca cgggactagg actattccag   300
```

-continued

| acttggcagg gggactttaa tggggagctc aacccactga ctgcctgaga gcccagaagt | 360 |
| gtcatttctg actatctaaa gaccagagca tctacttgct gccatggttg gctgctgggc | 420 |
| tggttttggg gttcttttgc attatgggct tatgggtact ttaatgtgac ttaatttcat | 480 |
| caaagccaca acgcagtgtt caagccnaat ctgcaaatat ccatcacact ggcggcgctc | 540 |
| naacatcn | 548 |

<210> SEQ ID NO 20
<211> LENGTH: 546
<212> TYPE: DNA
<213> ORGANISM: Homo sapiens
<220> FEATURE:
<221> NAME/KEY: misc_feature
<222> LOCATION: 531, 535
<223> OTHER INFORMATION: n = a,t,c or g

<400> SEQUENCE: 20

| gggggggtt ttacgactca ctgccgaggg cgaattgggc actctatatg catgctcgag | 60 |
| cggccgccag tgtgatggat atctgcagaa ttcggcttcc tcggtctgtc ttcttgactt | 120 |
| tgtctagtga ggcagccatt ctgcagaatt tcatctgctt taggtatgca gaccctgcac | 180 |
| tgcatgcgcg catatgcacg cgggtacaca cacacacaca cacacacaca cacacacaca | 240 |
| cacacacaca cacacacaca cgggactagg actattccag acttggcagg gggactttaa | 300 |
| tggggagctc aacccactga ctgcctgaga gcccagaagt gtcatttctg actatctaaa | 360 |
| gaccagagca tctacttgct gccatggttg gctgctgggc tggttttggg gttcttttgc | 420 |
| attatgggct tatgggtact ttaatgtgac ttaatttcat caaagccagc aaacgcagtg | 480 |
| ttcaagccga attccagcac actggcgggc gttactaatg gatcgaactc ngtancaagc | 540 |
| ttgatc | 546 |

<210> SEQ ID NO 21
<211> LENGTH: 536
<212> TYPE: DNA
<213> ORGANISM: Homo sapiens
<220> FEATURE:
<221> NAME/KEY: misc_feature
<222> LOCATION: 1, 2, 4, 5, 10, 12, 13, 274, 335, 360, 365, 420, 468,
       484, 507, 523, 533
<223> OTHER INFORMATION: n = a,t,c or g

<400> SEQUENCE: 21

| nncnntgctn anntaggtca cactatagaa tactcaagct atgcatcaag cttggtaccg | 60 |
| agctcggatc cactagtaac ggccgccagt gtgctgaat tcggcttcct cggtctgtct | 120 |
| tcttgacttt gtctagtgag gcagccattc tgcagaattt catctgcttt aggtatgcag | 180 |
| accctgcact gcatgcgcgc atatgcacgc gggtacaca acacacacac acacacacac | 240 |
| acacacacac acacacacac gggactagga ctantccaga cttggcaggg ggactttaat | 300 |
| ggggagctca acccactgac tgcctgagag cccanaagtg tcatttctga ctatctaaan | 360 |
| accanagcat ctacttgctg ccatggttgg ctgctgggct ggttttgggg ttcttttgcn | 420 |
| ttatgggctt atgggtactt taatgtgact taatttcatc aaagccanca aaccagtgtt | 480 |
| caanccgaat tctgcagata tccacanact ggcggcgctc cancatgctc tanagg | 536 |

<210> SEQ ID NO 22
<211> LENGTH: 537
<212> TYPE: DNA
<213> ORGANISM: Homo sapiens
<220> FEATURE:

```
<221> NAME/KEY: misc_feature
<222> LOCATION: 2, 7, 391, 412, 444, 447, 448, 455, 458, 468, 482, 483,
      496, 515, 526, 533, 537
<223> OTHER INFORMATION: n = a,t,c or g

<400> SEQUENCE: 22
gnaattngtt tacgactcac tacagggcga attgggcctc tagatgctgc tcgagcggcc    60
gccagtgtga tggatatctg cagaattcgg cttgaacact gcgtttgctg gctttgatga   120
aattaagtca cattaaagta cccataagcc cataatgcaa agaaccccca aaccagccc    180 agcagccaac catggcagca agtagatgct ctggtcttta gatagtcaga atgacactt    240 ctgggctctc aggcagtcag tgggttgagc tccccattaa agtcccctg ccaagtctgg    300 aatagtccta gtcccgtgtg tgtgtgtgtg tgtgtgtgtg tgtgtgtgtg tgtgtgtgtg    360
tacccgcgtg catatgcgcg catgcagtgc ngggtctgca tacctaaagc anatgaaatt   420
ctgcagaaat ggctgcctca ctanacnncg tcaanaanac agaccganga agccgaattc   480
cnncccactg ggcggncgtt actagtggat ccaancccgg tacaancttg aangcan      537

<210> SEQ ID NO 23
<211> LENGTH: 535
<212> TYPE: DNA
<213> ORGANISM: Homo sapiens
<220> FEATURE:
<221> NAME/KEY: misc_feature
<222> LOCATION: 3, 4, 5, 8, 14, 16, 28, 73, 153, 271, 277, 280, 288,
      291, 298, 299, 335, 340, 349, 355, 358, 379, 416, 418, 445, 456,
      465, 483, 489, 508, 526, 532
<223> OTHER INFORMATION: n = a,t,c or g

<400> SEQUENCE: 23
tannngcnat gctnanttag gtgaactnat agaatactca agctatgcat caagcttggt    60
accgagctcg ganccactag taacggccgc cagtgtgctg gaattcggct tcctcggtct   120
gtcttcttga ctttgtctag tgaggcagcc atnctgcaga atttcatctg ctttaggtat   180
gcagaccctg cactgcatgc gcgcatatgc acgcgggtac acacacacac acacacacac   240
acacacacac acacacacac acacacacac ncagganaan gactattnca nacttggnng   300
ggggacttta atggggagct caacccactg actgnctgan agcacatang tgtcnttnct   360
gactatctaa agaccaganc atctacttgc tgccatggtt ggctgctggg ctggtntngg   420
ggttcttttg cattatgggc ttatnggtac tttaangtga cttantttca tcaaagccaa   480
canacgctnt gtcaaaccga atctacanat atccatcaca ctggcnggcg cncaa        535

<210> SEQ ID NO 24
<211> LENGTH: 546
<212> TYPE: DNA
<213> ORGANISM: Homo sapiens
<220> FEATURE:
<221> NAME/KEY: misc_feature
<222> LOCATION: 1, 2, 3, 316, 408, 429, 432, 443, 460, 482, 483, 487,
      490, 497, 517, 533, 536, 542, 545, 546
<223> OTHER INFORMATION: n = a,t,c or g

<400> SEQUENCE: 24
nnnggaattt gttttacgac tcactgcgag ggcgaattgg gcctctagat gcatgctcga    60
gcggccgcca gtgtgatgga tatctgcaga attcggcttg aacactgcgt tgctggcttt   120
gatgaaatta agtcacatta agtacccat aagcccataa tgcaaagaa ccccaaaacc    180 agcccagcag ccaaccatgg cagcaagtag atgctctggt ctttagatag tcagaaatga   240
cacttctggg ctctcaggca gtcagtgggt tgagctcccc attaaagtcc cctgccaag   300
```

```
tctggaatag tcctantccc gtgtgtgtgt gtgtgtgtgt gtgtgtgtgt gtgtgtgtgt      360
gtgtgtgtgt gtgtgtgtac ccgcgtgcat atgcgcgcat gcagtgcngg gtctgcatac      420
ctaaagcana tnaaattctg canaatggct gcctcactan acaaagtcaa aaaaaaagac      480
gnngaanccn aattccnccc ctggcgggcg ttactantgg atccaactcg gtncancttg      540 angcnn                                                                 546

<210> SEQ ID NO 25
<211> LENGTH: 29
<212> TYPE: DNA
<213> ORGANISM: Artificial Sequence
<220> FEATURE:
<223> OTHER INFORMATION: synthesized oligonucleotide

<400> SEQUENCE: 25
gcgcaagctt tatatgatgc cccacccag                                        29

<210> SEQ ID NO 26
<211> LENGTH: 31
<212> TYPE: DNA
<213> ORGANISM: Artificial Sequence
<220> FEATURE:
<223> OTHER INFORMATION: synthesized oligonucleotide

<400> SEQUENCE: 26
gcgcggatcc gcccgtgatg aatcatgtga c                                     31

<210> SEQ ID NO 27
<211> LENGTH: 30
<212> TYPE: DNA
<213> ORGANISM: Artificial Sequence
<220> FEATURE:
<223> OTHER INFORMATION: synthesized oligonucleotide

<400> SEQUENCE: 27
gcgcaagctt cccatgtcac agtccaggca                                       30

<210> SEQ ID NO 28
<211> LENGTH: 31
<212> TYPE: DNA
<213> ORGANISM: Artificial Sequence
<220> FEATURE:
<223> OTHER INFORMATION: synthesized oligonucleotide

<400> SEQUENCE: 28
gcgcggatcc gcccgtgatg aatcatgtga c                                     31

<210> SEQ ID NO 29
<211> LENGTH: 28
<212> TYPE: DNA
<213> ORGANISM: Artificial Sequence
<220> FEATURE:
<223> OTHER INFORMATION: synthesized primer

<400> SEQUENCE: 29
gcgcaagctt cagccaacca tggcagca                                         28

<210> SEQ ID NO 30
<211> LENGTH: 31
<212> TYPE: DNA
<213> ORGANISM: Artificial Sequence
<220> FEATURE:
<223> OTHER INFORMATION: synthesized oligonucleotide
```

<400> SEQUENCE: 30
gcgcggatcc gcccgtgatg aatcatgtga c                                  31

<210> SEQ ID NO 31
<211> LENGTH: 9
<212> TYPE: PRT
<213> ORGANISM: Homo sapiens

<400> SEQUENCE: 31

Met Ala Ala Ser Arg Cys Ser Gly Leu
1               5

<210> SEQ ID NO 32
<211> LENGTH: 259
<212> TYPE: PRT
<213> ORGANISM: Homo sapiens
<220> FEATURE:
<221> NAME/KEY: VARIANT
<222> LOCATION: 10, 38, 40, 126, 145, 160, 172, 177, 194, 196, 198, 208,
      219, 221, 224, 227, 241, 245
<223> OTHER INFORMATION: Xaa = Any Amino Acid or Absent

<400> SEQUENCE: 32

Met Ala Ala Ser Arg Cys Ser Gly Leu Xaa Ile Val Arg Asn Asp Thr
1               5                   10                  15

Ser Gly Leu Ser Gly Ser Gln Trp Val Glu Leu Pro Ile Lys Val Pro
            20                  25                  30

Leu Pro Ser Leu Glu Xaa Ser Xaa Ser Arg Val Cys Val Cys Val Cys
        35                  40                  45

Val Cys Val Cys Val Tyr Pro Arg Ala Tyr Ala Arg Met Gln Cys Arg
    50                  55                  60

Val Cys Ile Pro Lys Ala Asp Glu Ile Leu Gln Asn Gly Cys Leu Ala
65                  70                  75                  80

Arg Gln Ser Gln Glu Asp Arg Pro Arg Arg Glu Arg Leu Met Cys Leu
                85                  90                  95

His Tyr Gln Glu Thr Gly Phe Ser Lys Pro Ala Arg His Pro Ile Gln
            100                 105                 110

Gln Tyr Glu Thr Gly His Ile Ser Leu Arg Cys Gln Arg Xaa Lys Cys
        115                 120                 125

Ser Cys Ile Phe Ile Leu His Cys Tyr Glu Val Gly Cys Asn Thr Ala
    130                 135                 140

Xaa Val Glu Tyr Lys Asn Thr Ala Trp Lys His Met Ile Trp Ile Xaa
145                 150                 155                 160

Ile Ala Ala Val Ser Phe Thr Cys Tyr Arg Leu Xaa Ala Arg Pro Leu
                165                 170                 175

Xaa Gly Tyr Phe Phe Thr Val Gly Arg Asp Lys Thr Tyr Phe Lys Gly
            180                 185                 190

Ser Xaa Ser Xaa Thr Xaa Val Asn Glu Cys Lys Ser Val His Ile Xaa
        195                 200                 205

Thr Val Ile Leu Lys His Asn Thr Ser Lys Xaa His Xaa Tyr His Xaa
    210                 215                 220

Arg Asp Xaa Leu Ser Thr Val Arg His Met Ile His Gly His Leu
225                 230                 235                 240

Xaa Asp Ile Lys Xaa Arg Gly Glu Ala Cys Ser Asn Lys Lys Tyr Cys
                245                 250                 255

His Ser Tyr

```
<210> SEQ ID NO 33
<211> LENGTH: 259
<212> TYPE: PRT
<213> ORGANISM: Homo sapiens
<220> FEATURE:
<221> NAME/KEY: VARIANT
<222> LOCATION: 12, 94, 122, 157, 184, 211, 213, 235
<223> OTHER INFORMATION: Xaa = Any Amino Acid or Absent

<400> SEQUENCE: 33

Pro Trp Gln Gln Val Asp Ala Leu Val Phe Arg Xaa Ser Glu Met Thr
  1               5                  10                  15

Leu Leu Gly Ser Gln Ala Val Ser Gly Leu Ser Ser Pro Leu Lys Ser
             20                  25                  30

Pro Cys Gln Val Trp Asn Ser Pro Ser Pro Val Cys Val Cys Val Cys
         35                  40                  45

Val Cys Val Cys Val Cys Thr Arg Val His Met Arg Ala Cys Ser Ala
 50                  55                  60

Gly Ser Ala Tyr Leu Lys Gln Met Lys Phe Cys Arg Met Ala Ala Ser
 65                  70                  75                  80

Leu Asp Lys Val Lys Lys Thr Asp Arg Gly Glu Arg Gly Xaa Cys Val
             85                  90                  95

Ser Thr Thr Lys Arg Gln Ala Ser Leu Ser Gln Arg Asp Ile Pro Ser
            100                 105                 110

Asn Asn Met Lys Leu Ala Thr Phe Pro Xaa Asp Val Asn Val Glu Ser
            115                 120                 125

Val Ala Ala Ser Leu Phe Phe Thr Val Met Lys Leu Gly Ala Thr Gln
            130                 135                 140

Leu Glu Trp Asn Thr Lys Thr Pro Leu Gly Asn Thr Xaa Ser Gly Phe
145                 150                 155                 160

Glu Ser Gln Leu Tyr His Ser Pro Ala Ile Asp Ser Glu Gln Asp Leu
            165                 170                 175

Ser Glu Val Ile Ser Ser Gln Xaa Val Glu Thr Arg Leu Thr Ser Lys
            180                 185                 190

Val Leu Lys Val Glu Pro Glu Ser Met Asn Ala Lys Val Phe Thr Phe
            195                 200                 205

Lys Leu Xaa Phe Xaa Ser Thr Ile Gln Val Asn Ser Ile Asn Ile Ile
            210                 215                 220

Arg Glu Ile Asn Leu Ala Leu Cys Val Thr Xaa Phe Ile Thr Ala Ile
225                 230                 235                 240

Cys Glu Ile Ser Asn Arg Glu Val Lys Pro Ala Val Ile Lys Asn Thr
            245                 250                 255

Ala Ile Ala

<210> SEQ ID NO 34
<211> LENGTH: 259
<212> TYPE: PRT
<213> ORGANISM: Homo sapiens
<220> FEATURE:
<221> NAME/KEY: VARIANT
<222> LOCATION: 5, 15, 26, 30, 69, 72, 81, 105, 115, 129, 138, 170, 185,
      201, 218, 229, 248, 252, 253, 258
<223> OTHER INFORMATION: Xaa = Any Amino Acid or Absent

<400> SEQUENCE: 34

His Gly Ser Lys Xaa Met Leu Trp Ser Leu Asp Ser Gln Lys Xaa His
  1               5                  10                  15

Phe Trp Ala Leu Arg Gln Ser Val Gly Xaa Ala Pro His Xaa Ser Pro
             20                  25                  30
```

Pro Ala Lys Ser Gly Ile Val Leu Val Pro Cys Val Cys Val
    35                  40                  45

Cys Val Cys Val Cys Val Pro Ala Cys Ile Cys Ala His Ala Val Gln
 50                  55                  60

Gly Leu His Thr Xaa Ser Arg Xaa Asn Ser Ala Glu Trp Leu Pro Arg
 65                  70                  75                  80

Xaa Thr Lys Ser Arg Arg Gln Thr Glu Glu Arg Glu Val Asp Val Ser
                 85                  90                  95

Pro Leu Pro Arg Asp Arg Leu Leu Xaa Ala Ser Glu Thr Ser His Pro
            100                 105                 110

Thr Ile Xaa Asn Trp Pro His Phe Leu Glu Met Ser Thr Leu Lys Val
        115                 120                 125

Xaa Leu His Leu Tyr Ser Ser Leu Leu Xaa Ser Trp Val Gln His Ser
    130                 135                 140

Leu Ser Gly Ile Gln Lys His Arg Leu Glu Thr His Asp Leu Asp Leu
145                 150                 155                 160

Asn Arg Ser Cys Ile Ile His Leu Leu Xaa Thr Leu Ser Lys Thr Ser
                165                 170                 175

Leu Arg Leu Phe Leu His Ser Arg Xaa Arg Gln Asp Leu Leu Gln Arg
            180                 185                 190

Phe Leu Lys Leu Asn Leu Ser Gln Xaa Met Gln Lys Cys Ser His Leu
    195                 200                 205

Asn Cys Asn Phe Lys Ala Gln Tyr Lys Xaa Ile Ala Leu Ile Ser Leu
    210                 215                 220

Glu Arg Leu Thr Xaa His Cys Ala Ser His Asp Ser Ser Arg Pro Ser
225                 230                 235                 240

Val Arg Tyr Gln Ile Glu Arg Xaa Ser Leu Gln Xaa Xaa Lys Ile Leu
                245                 250                 255

Pro Xaa Leu

<210> SEQ ID NO 35
<211> LENGTH: 780
<212> TYPE: DNA
<213> ORGANISM: Homo sapiens

<400> SEQUENCE: 35
accatggcag caagtagatg ctctggtctt tagatagtca gaaatgacac ttctgggctc      60
ccaggcagtc agtgggttga gctccccatt aaagtccccc tgccaagtct ggaatagtcc     120
tagtcccgtg tgtgtgtgtg tgtgtgtgtg tgtgtgtgtg tgtacccgcg tgcatatgcg     180
cgcatgcagt gcagggtctg catacctaaa gcagatgaaa ttctgcagaa tggctgcctc     240
gctagacaaa gtcaagaaga cagaccgagg agagagaggt tgatgtgtct ccactaccaa     300
gagacaggct tctctaagcc agcgagacat cccatccaac aatatgaaac tggccacatt     360
tccttgagat gtcaacgttg aaagtgtagc tgcatcttta ttcttcactg ttatgaagtt     420
gggtgcaaca cagcttgagt ggaatacaaa acaccgctt ggaaacacat gatctggatt     480
tgaatcgcag ctgtatcatt cacctgctat agactctgag caagacctct ctgaggttat     540
ttcttcacag taggtagaga caagacttac ttcaaaggtt cttaaagttg aacctgagtc     600
aatgaatgca aaagtgttca catttaaact gtaattttaa agcacaatac aagtaaatag     660
cattaatatc attagagaga ttaacttagc actgtgcgtc acatgattca tcacggccat     720
ctgtgagata tcaaatagag aggtgaagcc tgcagtaata aaaaatactg ccatagctat     780

<210> SEQ ID NO 36
<211> LENGTH: 779
<212> TYPE: DNA
<213> ORGANISM: Homo sapiens

<400> SEQUENCE: 36

```
ccatggcagc aagtagatgc tctggtcttt agatagtcag aaatgacact tctgggctct      60
caggcagtca gtgggttgag ctccccatta aagtccccct gccaagtctg aatagtcct     120
agtcccgtgt gtgtgtgtgt gtgtgtgtgt gtgtgtgtgt gtacccgcgt gcatatgcgc    180
gcatgcagtg cagggtctgc atacctaaag cagatgaaat tctgcagaat ggctgcctcg    240
ctagacaaag tcaagaagac agaccgagga gagagaggtt gatgtgtctc cactaccaag    300
agacaggctt ctctaagcca gcgagacatc ccatccaaca atatgaaact ggccacattt    360
ccttgagatg tcaacgttga agtgtagct gcatctttat tcttcactgt tatgaagttg     420
ggtgcaacac agcttgagtg aatacaaaa acaccgcttg gaaacacatg atctggattt     480
gaatcgcagc tgtatcattc acctgctata gactctgagc aagacctctc tgaggttatt    540
tcttcacagt aggtagagac aagacttact tcaaaggttc ttaaagttga acctgagtca    600
atgaatgcaa aagtgttcac atttaaactg taattttaaa gcacaataca gtaaatagc    660
attaatatca ttagagagat taacttagca ctgtgcgtca catgattcat cacggccatc    720
tgtgagatat caaatagaga ggtgaagcct gcagtaataa aaaatactgc catagctat    779
```

<210> SEQ ID NO 37
<211> LENGTH: 778
<212> TYPE: DNA
<213> ORGANISM: Homo sapiens

<400> SEQUENCE: 37

```
catggcagca agtagatgct ctggtctta gatagtcaga aatgacactt ctgggctctc      60
aggcagtcag tgggttgagc tccccattaa agtcccctg ccaagtctgg aatagtccta    120
gtcccgtgtg tgtgtgtgtg tgtgtgtgtg tgtgtgtgtg tacccgcgtg catatgcgcg    180
catgcagtgc agggtctgca tacctaaagc agatgaaatt ctgcagaatg gctgcctcgc    240
tagacaaagt caagaagaca gaccgaggag agagaggttg atgtgtctcc actaccaaga    300
gacaggcttc tctaagccag cgagacatcc catccaacaa tatgaaactg ccacatttc    360
cttgagatgt caacgttgaa agtgtagctg catctttatt cttcactgtt atgaagttgg    420
gtgcaacaca gcttgagtgg aatacaaaaa caccgcttgg aaacacatga tctggatttg    480
aatcgcagct gtatcattca cctgctatag actctgagca agacctctct gaggttattt    540
cttcacagta ggtagagaca agacttactt caaaggttct taaagttgaa cctgagtcaa    600
tgaatgcaaa agtgttcaca tttaaactgt aattttaaag cacaatacaa gtaaatagca    660
ttaatatcat tagagagatt aacttagcac tgtgcgtcac atgattcatc acggccatct    720
gtgagatatc aaatagagag gtgaagcctg cagtaataaa aaatactgcc atagctat    778
```

<210> SEQ ID NO 38
<211> LENGTH: 183
<212> TYPE: PRT
<213> ORGANISM: Homo sapiens
<220> FEATURE:
<221> NAME/KEY: VARIANT
<222> LOCATION: 28, 30, 116, 135, 150, 162, 167
<223> OTHER INFORMATION: Xaa = Any Amino Acid or Absent

<400> SEQUENCE: 38

```
Ile Val Arg Asn Asp Thr Ser Gly Leu Ser Gly Ser Gln Trp Val Glu
1               5                   10                  15

Leu Pro Ile Lys Val Pro Leu Pro Ser Leu Glu Xaa Ser Xaa Ser Arg
            20                  25                  30

Val Cys Val Cys Val Cys Val Cys Val Tyr Pro Arg Ala Tyr
            35                  40                  45

Ala Arg Met Gln Cys Arg Val Cys Ile Pro Lys Ala Asp Glu Ile Leu
    50                  55                  60

Gln Asn Gly Cys Leu Ala Arg Gln Ser Gln Glu Asp Arg Pro Arg Arg
65                  70                  75                  80

Glu Arg Leu Met Cys Leu His Tyr Gln Glu Thr Gly Phe Ser Lys Pro
                85                  90                  95

Ala Arg His Pro Ile Gln Gln Tyr Glu Thr Gly His Ile Ser Leu Arg
                100                 105                 110

Cys Gln Arg Xaa Lys Cys Ser Cys Ile Phe Ile Leu His Cys Tyr Glu
            115                 120                 125

Val Gly Cys Asn Thr Ala Xaa Val Glu Tyr Lys Asn Thr Ala Trp Lys
            130                 135                 140

His Met Ile Trp Ile Xaa Ile Ala Ala Val Ser Phe Thr Cys Tyr Arg
145                 150                 155                 160

Leu Xaa Ala Arg Pro Leu Xaa Gly Tyr Phe Phe Thr Val Gly Arg Asp
                165                 170                 175

Lys Thr Tyr Phe Lys Gly Ser
                180

<210> SEQ ID NO 39
<211> LENGTH: 241
<212> TYPE: PRT
<213> ORGANISM: Homo sapiens
<220> FEATURE:
<221> NAME/KEY: VARIANT
<222> LOCATION: 28, 30, 116, 135, 150, 162, 167, 184, 186, 188, 198,
      209, 211, 214, 217, 231, 235
<223> OTHER INFORMATION: Xaa = Any Amino Acid or Absent

<400> SEQUENCE: 39

Ile  Val Arg Asn Asp Thr Ser Gly Leu Ser Gly Ser Gln Trp Val Glu
1                5                   10                  15

Leu Pro Ile Lys Val Pro Leu Pro Ser Leu Glu Xaa Ser Xaa Ser Arg
            20                  25                  30

Val Cys Val Cys Val Cys Val Cys Val Tyr Pro Arg Ala Tyr
            35                  40                  45

Ala Arg Met Gln Cys Arg Val Cys Ile Pro Lys Ala Asp Glu Ile Leu
    50                  55                  60

Gln Asn Gly Cys Leu Ala Arg Gln Ser Gln Glu Asp Arg Pro Arg Arg
65                  70                  75                  80

Glu Arg Leu Met Cys Leu His Tyr Gln Glu Thr Gly Phe Ser Lys Pro
                85                  90                  95

Ala Arg His Pro Ile Gln Gln Tyr Glu Thr Gly His Ile Ser Leu Arg
                100                 105                 110

Cys Gln Arg Xaa Lys Cys Ser Cys Ile Phe Ile Leu His Cys Tyr Glu
            115                 120                 125

Val Gly Cys Asn Thr Ala Xaa Val Glu Tyr Lys Asn Thr Ala Trp Lys
            130                 135                 140

His Met Ile Trp Ile Xaa Ile Ala Ala Val Ser Phe Thr Cys Tyr Arg
145                 150                 155                 160
```

```
Leu Xaa Ala Arg Pro Leu Xaa Gly Tyr Phe Thr Val Gly Arg Asp
        165                 170                 175

Lys Thr Tyr Phe Lys Gly Ser Xaa Ser Xaa Thr Xaa Val Asn Glu Cys
            180                 185                 190

Lys Ser Val His Ile Xaa Thr Val Ile Leu Lys His Asn Thr Ser Lys
                195                 200                 205

Xaa His Xaa Tyr His Xaa Arg Asp Xaa Leu Ser Thr Val Arg His Met
    210                 215                 220

Ile His His Gly His Leu Xaa Asp Ile Lys Xaa Arg Gly Glu Ala Cys
225                 230                 235                 240

Ser

<210> SEQ ID NO 40
<211> LENGTH: 198
<212> TYPE: PRT
<213> ORGANISM: Homo sapiens
<220> FEATURE:
<221> NAME/KEY: VARIANT
<222> LOCATION: 82, 110, 145, 172
<223> OTHER INFORMATION: Xaa = Any Amino Acid or Absent

<400> SEQUENCE: 40

Ser Glu Met Thr Leu Leu Gly Ser Gln Ala Val Ser Gly Leu Ser Ser
1               5                   10                  15

Pro Leu Lys Ser Pro Cys Gln Val Trp Asn Ser Pro Ser Pro Val Cys
            20                  25                  30

Val Cys Val Cys Val Cys Val Cys Thr Arg Val His Met Arg
        35                  40                  45

Ala Cys Ser Ala Gly Ser Ala Tyr Leu Lys Gln Met Lys Phe Cys Arg
    50                  55                  60

Met Ala Ala Ser Leu Asp Lys Val Lys Lys Thr Asp Arg Gly Glu Arg
65              70                  75                  80

Gly Xaa Cys Val Ser Thr Thr Lys Arg Gln Ala Ser Leu Ser Gln Arg
                85                  90                  95

Asp Ile Pro Ser Asn Asn Met Lys Leu Ala Thr Phe Pro Xaa Asp Val
            100                 105                 110

Asn Val Glu Ser Val Ala Ala Ser Leu Phe Phe Thr Val Met Lys Leu
        115                 120                 125

Gly Ala Thr Gln Leu Glu Trp Asn Thr Lys Thr Pro Leu Gly Asn Thr
    130                 135                 140

Xaa Ser Gly Phe Glu Ser Gln Leu Tyr His Ser Pro Ala Ile Asp Ser
145                 150                 155                 160

Glu Gln Asp Leu Ser Glu Val Ile Ser Ser Gln Xaa Val Glu Thr Arg
                165                 170                 175

Leu Thr Ser Lys Val Leu Lys Val Glu Pro Glu Ser Met Asn Ala Lys
            180                 185                 190

Val Phe Thr Phe Lys Leu
        195

<210> SEQ ID NO 41
<211> LENGTH: 239
<212> TYPE: PRT
<213> ORGANISM: Homo sapiens
<220> FEATURE:
<221> NAME/KEY: VARIANT
<222> LOCATION: 82, 110, 145, 172, 199, 201, 223
<223> OTHER INFORMATION: Xaa = Any Amino Acid or Absent
```

<400> SEQUENCE: 41

```
Ser Glu Met Thr Leu Leu Gly Ser Gln Ala Val Ser Gly Leu Ser Ser
 1               5                  10                  15

Pro Leu Lys Ser Pro Cys Gln Val Trp Asn Ser Pro Ser Pro Val Cys
             20                  25                  30

Val Cys Val Cys Val Cys Val Cys Thr Arg Val His Met Arg
         35                  40                  45

Ala Cys Ser Ala Gly Ser Ala Tyr Leu Lys Gln Met Lys Phe Cys Arg
 50                  55                  60

Met Ala Ala Ser Leu Asp Lys Val Lys Lys Thr Asp Arg Gly Glu Arg
 65                  70                  75                  80

Gly Xaa Cys Val Ser Thr Thr Lys Arg Gln Ala Ser Leu Ser Gln Arg
                 85                  90                  95

Asp Ile Pro Ser Asn Asn Met Lys Leu Ala Thr Phe Pro Xaa Asp Val
             100                 105                 110

Asn Val Glu Ser Val Ala Ala Ser Leu Phe Phe Thr Val Met Lys Leu
             115                 120                 125

Gly Ala Thr Gln Leu Glu Trp Asn Thr Lys Thr Pro Leu Gly Asn Thr
130                 135                 140

Xaa Ser Gly Phe Glu Ser Gln Leu Tyr His Ser Pro Ala Ile Asp Ser
145                 150                 155                 160

Glu Gln Asp Leu Ser Glu Val Ile Ser Ser Gln Xaa Val Glu Thr Arg
                 165                 170                 175

Leu Thr Ser Lys Val Leu Lys Val Glu Pro Glu Ser Met Asn Ala Lys
             180                 185                 190

Val Phe Thr Phe Lys Leu Xaa Phe Xaa Ser Thr Ile Gln Val Asn Ser
             195                 200                 205

Ile Asn Ile Ile Arg Glu Ile Asn Leu Ala Leu Cys Val Thr Xaa Phe
             210                 215                 220

Ile Thr Ala Ile Cys Glu Ile Ser Asn Arg Glu Val Lys Pro Ala
225                 230                 235
```

<210> SEQ ID NO 42
<211> LENGTH: 240
<212> TYPE: PRT
<213> ORGANISM: Homo sapiens
<220> FEATURE:
<221> NAME/KEY: VARIANT
<222> LOCATION: 4, 15, 19, 58, 61, 70, 94, 104, 118, 127, 159, 174, 190,
   207, 218, 237
<223> OTHER INFORMATION: Xaa = Any Amino Acid or Absent

<400> SEQUENCE: 42

```
Ser Gln Lys Xaa His Phe Trp Ala Leu Arg Gln Ser Val Gly Xaa Ala
 1               5                  10                  15

Pro His Xaa Ser Pro Ala Lys Ser Gly Ile Val Leu Val Pro Cys
             20                  25                  30

Val Cys Val Cys Val Cys Val Cys Val Pro Ala Cys Ile Cys
         35                  40                  45

Ala His Ala Val Gln Gly Leu His Thr Xaa Ser Arg Xaa Asn Ser Ala
 50                  55                  60

Glu Trp Leu Pro Arg Xaa Thr Lys Ser Arg Arg Gln Thr Glu Glu Arg
 65                  70                  75                  80

Glu Val Asp Val Ser Pro Leu Pro Arg Asp Arg Leu Leu Xaa Ala Ser
                 85                  90                  95

Glu Thr Ser His Pro Thr Ile Xaa Asn Trp Pro His Phe Leu Glu Met
```

```
            100                 105                 110
Ser Thr Leu Lys Val Xaa Leu His Leu Tyr Ser Ser Leu Leu Xaa Ser
            115                 120                 125

Trp Val Gln His Ser Leu Ser Gly Ile Gln Lys His Arg Leu Glu Thr
            130                 135                 140

His Asp Leu Asp Leu Asn Arg Ser Cys Ile Ile His Leu Leu Xaa Thr
145                 150                 155                 160

Leu Ser Lys Thr Ser Leu Arg Leu Phe Leu His Ser Arg Xaa Arg Gln
                165                 170                 175

Asp Leu Leu Gln Arg Phe Leu Lys Leu Asn Leu Ser Gln Xaa Met Gln
                180                 185                 190

Lys Cys Ser His Leu Asn Cys Asn Phe Lys Ala Gln Tyr Lys Xaa Ile
                195                 200                 205

Ala Leu Ile Ser Leu Glu Arg Leu Thr Xaa His Cys Ala Ser His Asp
            210                 215                 220

Ser Ser Arg Pro Ser Val Arg Tyr Gln Ile Glu Arg Xaa Ser Leu Gln
225                 230                 235                 240

<210> SEQ ID NO 43
<211> LENGTH: 726
<212> TYPE: DNA
<213> ORGANISM: Homo sapiens

<400> SEQUENCE: 43
atggcagcaa gtagatgctc tggtctttag atagtcagaa atgacacttc tgggctctca     60
ggcagtcagt gggttgagct ccccattaaa gtcccctgc caagtctgga atagtcctag    120
tcccgtgtgt gtgtgtgtgt gtgtgtgtgt gtgtgtgtgt acccgcgtgc atatgcgcgc    180
atgcagtgca gggtctgcat acctaaagca gatgaaattc tgcagaatgg ctgcctcgct    240
agacaaagtc aagaagacag accgaggaga gagaggttga tgtgtctcca ctaccaagag    300
acaggcttct ctaagccagc gagacatccc atccaacaat atgaaactgg ccacatttcc    360
ttgagatgtc aacgttgaaa gtgtagctgc atctttattc ttcactgtta tgaagttggg    420
tgcaacacag cttgagtgga atacaaaaac accgcttgga acacatgat ctggatttga     480 atcgcagctg tatcattcac ctgctataga ctctgagcaa gacctctctg aggttatttc    540
ttcacagtag gtagagacaa gacttacttc aaaggttctt aaagttgaac ctgagtcaat    600
gaatgcaaaa gtgttcacat ttaaactgta attttaaagc acaatacaag taaatagcat    660
taatatcatt agagagatta acttagcact gtgcgtcaca tgattcatca cggcggatcc    720
cgggtg                                                              726

<210> SEQ ID NO 44
<211> LENGTH: 62
<212> TYPE: RNA
<213> ORGANISM: Homo sapiens

<400> SEQUENCE: 44
cuuuagauag ucagaaauga cacuucuggg cucucaggca gucagugggu ugagcucccc     60
au                                                                   62

<210> SEQ ID NO 45
<211> LENGTH: 649
<212> TYPE: DNA
<213> ORGANISM: Homo sapiens

<400> SEQUENCE: 45
```

```
cagccaacca tggcagcaag tagatgctct ggtctttaga tagtcagaaa tgacacttct      60
gggctctcag gcagtcagtg ggttgagctc cccattaaag tcccctgcc aagtctggaa      120 tagtcctagt cccgtgtgtg tgtgtgtgtg tgtgtgtgta cccgcgtgca                180
tatgcgcgca tgcagtgcag ggtctgcata cctaaagcag atgaaattct gcagaatggc    240
tgcctcgcta gacaaagtca agaagacaga ccgaggagag agaggttgat gtgtctccac    300
taccaagaga caggcttctc taagccagcg agacatccca tccaacaata tgaaactggc    360
cacatttcct tgagatgtca acgttgaaag tgtagctgca tctttattct tcactgttat    420
gaagttgggt gcaacacagc ttgagtggaa tacaaaaaca ccgcttggaa acacatgatc    480
tggatttgaa tcgcagctgt atcattcacc tgctatagac tctgagcaag acctctctga    540
ggttatttct tcacagtagg tagagacaag acttacttca aaggttctta aagttgaacc    600
tgagtcaatg aatgcaaaag tgttcacatt taaactgtaa ttttaaagc                 649
```

<210> SEQ ID NO 46
<211> LENGTH: 208
<212> TYPE: PRT
<213> ORGANISM: Homo sapiens
<220> FEATURE:
<221> NAME/KEY: VARIANT
<222> LOCATION: 10, 92, 120, 155, 182
<223> OTHER INFORMATION: Xaa = Any Amino Acid or Absent

<400> SEQUENCE: 46

```
Met Ala Ala Ser Arg Cys Ser Gly Leu Xaa Ser Glu Met Thr Leu Leu
 1               5                   10                  15

Gly Ser Gln Ala Val Ser Gly Leu Ser Ser Pro Leu Lys Ser Pro Cys
            20                  25                  30

Gln Val Trp Asn Ser Pro Ser Pro Val Cys Val Cys Val Cys Val Cys
        35                  40                  45

Val Cys Val Cys Thr Arg Val His Met Arg Ala Cys Ser Ala Gly Ser
    50                  55                  60

Ala Tyr Leu Lys Gln Met Lys Phe Cys Arg Met Ala Ala Ser Leu Asp
65                  70                  75                  80

Lys Val Lys Lys Thr Asp Arg Gly Glu Arg Gly Xaa Cys Val Ser Thr
                85                  90                  95

Thr Lys Arg Gln Ala Ser Leu Ser Gln Arg Asp Ile Pro Ser Asn Asn
            100                 105                 110

Met Lys Leu Ala Thr Phe Pro Xaa Asp Val Asn Val Glu Ser Val Ala
        115                 120                 125

Ala Ser Leu Phe Phe Thr Val Met Lys Leu Gly Ala Thr Gln Leu Glu
    130                 135                 140

Trp Asn Thr Lys Thr Pro Leu Gly Asn Thr Xaa Ser Gly Phe Glu Ser
145                 150                 155                 160

Gln Leu Tyr His Ser Pro Ala Ile Asp Ser Glu Gln Asp Leu Ser Glu
                165                 170                 175

Val Ile Ser Ser Gln Xaa Val Glu Thr Arg Leu Thr Ser Lys Val Leu
            180                 185                 190

Lys Val Glu Pro Glu Ser Met Asn Ala Lys Val Phe Thr Phe Lys Leu
        195                 200                 205
```

<210> SEQ ID NO 47
<211> LENGTH: 210
<212> TYPE: PRT
<213> ORGANISM: Homo sapiens

```
<220> FEATURE:
<221> NAME/KEY: VARIANT
<222> LOCATION: 10, 11, 12, 13, 14, 94, 122, 157, 184
<223> OTHER INFORMATION: Xaa = Any Amino Acid or Absent

<400> SEQUENCE: 47

Met Ala Ala Ser Arg Cys Ser Gly Leu Xaa Xaa Xaa Xaa Xaa Met Thr
 1               5                  10                  15

Leu Leu Gly Ser Gln Ala Val Ser Gly Leu Ser Ser Pro Leu Lys Ser
            20                  25                  30

Pro Cys Gln Val Trp Asn Ser Pro Ser Pro Val Cys Val Cys Val Cys
        35                  40                  45

Val Cys Val Cys Val Cys Thr Arg Val His Met Arg Ala Cys Ser Ala
    50                  55                  60

Gly Ser Ala Tyr Leu Lys Gln Met Lys Phe Cys Arg Met Ala Ala Ser
 65                 70                  75                  80

Leu Asp Lys Val Lys Lys Thr Asp Arg Gly Glu Arg Gly Xaa Cys Val
                85                  90                  95

Ser Thr Thr Lys Arg Gln Ala Ser Leu Ser Gln Arg Asp Ile Pro Ser
            100                 105                 110

Asn Asn Met Lys Leu Ala Thr Phe Pro Xaa Asp Val Asn Val Glu Ser
            115                 120                 125

Val Ala Ala Ser Leu Phe Phe Thr Val Met Lys Leu Gly Ala Thr Gln
    130                 135                 140

Leu Glu Trp Asn Thr Lys Thr Pro Leu Gly Asn Thr Xaa Ser Gly Phe
145                 150                 155                 160

Glu Ser Gln Leu Tyr His Ser Pro Ala Ile Asp Ser Glu Gln Asp Leu
                165                 170                 175

Ser Glu Val Ile Ser Ser Gln Xaa Val Glu Thr Arg Leu Thr Ser Lys
            180                 185                 190

Val Leu Lys Val Glu Pro Glu Ser Met Asn Ala Lys Val Phe Thr Phe
            195                 200                 205

Lys Leu
    210
```